US010626099B2

(12) United States Patent
Farney et al.

(10) Patent No.: US 10,626,099 B2
(45) Date of Patent: Apr. 21, 2020

(54) PROCESS FOR PREPARING PLEUROMUTILIN

(71) Applicant: California Institute of Technology, Pasadena, CA (US)

(72) Inventors: Elliot P. Farney, Vernon Hills, IL (US); Sean S. Feng, Alhambra, CA (US); Sarah Reisman, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/157,926

(22) Filed: Oct. 11, 2018

(65) Prior Publication Data

US 2019/0106400 A1 Apr. 11, 2019

Related U.S. Application Data

(60) Provisional application No. 62/571,117, filed on Oct. 11, 2017, provisional application No. 62/599,886, filed on Dec. 18, 2017.

(51) Int. Cl.

| | |
|---|---|
| *C07D 319/06* | (2006.01) |
| *C07C 69/757* | (2006.01) |
| *C07C 49/172* | (2006.01) |
| *C07C 45/64* | (2006.01) |
| *C07F 7/18* | (2006.01) |
| *C07C 49/753* | (2006.01) |
| *C07C 29/40* | (2006.01) |
| *C07C 45/65* | (2006.01) |
| *C07C 45/29* | (2006.01) |
| *C07C 45/68* | (2006.01) |
| *C07C 49/693* | (2006.01) |
| *C07C 35/32* | (2006.01) |
| *C07C 45/30* | (2006.01) |
| *C07C 49/757* | (2006.01) |
| *C07C 67/29* | (2006.01) |
| *C07B 51/00* | (2006.01) |
| *A61P 31/04* | (2006.01) |
| *C07C 67/14* | (2006.01) |

(52) U.S. Cl.
CPC ............ *C07D 319/06* (2013.01); *C07C 29/40* (2013.01); *C07C 35/32* (2013.01); *C07C 45/29* (2013.01); *C07C 45/30* (2013.01); *C07C 45/305* (2013.01); *C07C 45/64* (2013.01); *C07C 45/65* (2013.01); *C07C 45/68* (2013.01); *C07C 49/172* (2013.01); *C07C 49/693* (2013.01); *C07C 49/753* (2013.01); *C07C 49/757* (2013.01); *C07C 67/29* (2013.01); *C07C 69/757* (2013.01); *C07F 7/1804* (2013.01); *A61P 31/04* (2018.01); *C07B 51/00* (2013.01); *C07B 2200/07* (2013.01); *C07C 67/14* (2013.01); *C07C 2602/24* (2017.05); *C07C 2603/82* (2017.05)

(58) Field of Classification Search
CPC ............................................. C07C 2603/76
See application file for complete search history.

(56) References Cited

PUBLICATIONS

Helm, M.D., et al. "Total Synthesis of (+)-Pleuromutilin." Chem. Eur. J. (2013), vol. 19, pp. 6718-6723. (Year: 2013).*
Murphy S.K. et al., "A modular and enanioselective synthesis of the pleuromutilian antibiotics", Science, Jun. 2, 2017, vol. 356, pp. 956-959.
Helm, M.D. et al., "SmI2-mediated dialdehyde cyclization cascades", Tetrahedron Letters, 2009, vol. 50, pp. 3224-3226.
Helm, M.D. et al., "A Dialdehyde Cyclization Cascade: An Approach to Pleuromutilin", Angewandte Chemie International Edition, 2009, vol. 48, pp. 9315-9317.
Findey T.J. K. et al., "A Stereoselective, Sm(II)-mediated approach to decorated cis-hydrindanes: synthetic studies on faurinone and pleuromutilin", Organic & Biomolecular Chemistry, 2011, vol. 9, pp. 2433-2451.
White, et al., (R)-(+)-3,4-Dimethylcyclohex-2-En-1-One; Org. Synth. 2005, 82, 108-114.
Steves, et al., Copper(I)/ABNO-Catalyzed Aerobic Alcohol Oxidation: Alleviating Steric and Electronic Constraints of Cu/TEMPO Catalyst Systems; J. Am. Chem. Soc., 2013, 135, 15742-15745.
Singh, et al., Amalgamation of Synthetic Biology and Chemistry for High-Throughput Nonconventional Synthesis of the Antimalarial Drug Artemisinin; Organic Process Research & Development; 2017, 21, 551-558.
Poulsen, et al., The pleuromutilin drugs tiamulin and valnemulin bind to the RNA at the peptidyl transferase centre on the ribosome; Molecular Microbiology; 2001, 41, 1091-1099.
Parsons, et al., Use of intensity quotients and differences in absolute structure refinement; Acta Crystallographica; 2013, B69, 249-259.
Mulzer, et al., Total Synthesis of the Boron-Containing Ion Carrier Antibiotic Macrodiolide Tartrolon B; J. Org. Chem.; 2004, 69, 891-898.
Macrae, et al., Mercury: visualization and analysis of crystal structures; Applied Crystallography; 2006, 39, 453-457.
Krasovskiy, et al., Soluble Lanthanide Salts (LnCl3-2 LiCl) for the Improved Addition of Organomagnesium Reagents to Carbonyl Compounds; Angewandte Chemie Int. Ed.; 2006, 45, 497-500.
Iwasaki, et al., Simple, Chemoselective Hydrogenation with Thermodynamic Stereocontrol; J. Am. Chem. Soc.; 2014, 136, 1300-1303.
Fazakerley, et al., Total Synthesis of (+)-Pleuromutilin, Chemistry: A European Journal; 2013, 19, 6718-6723.
Farney, et al., A Total Synthesis of (+)-Pleuromutilin; J. Am. Chem. Soc.; 2018, 140(4): 1267-1270.
Dauben et al., Direct Oxidation of Tertiary Allylic Alcohols. A Simple and Effective Method for Alkylative Carbonyl Transposition; J. Org. Chem.; 1977, 42, 682-685.
Bervec : 3-[4-ethenyl-6-hydroxy-3-(methoxymethoxy)-4,7,8-trimethyl-2-methylidene-11-oxobicyclo[5.3.1]undecan-1-yl]propanoic acid; Deposition No. 1589655; 3 pages.
Bervay : 6-ethenyl-8-hydroxy-5-(methoxymethoxy)-6,9,10-trimethyl-4-methylideneoctahydro-3a,9-propanocyclopenta[8]annulen-1(4H)-one; Deposition No. 1589654; 3 pages.
Bertuq : 7-ethenyl-6-(methoxymethoxy)-1,7,12-trimethyl-5-methylidene-3,4,5,6,7,8-hexahydro-1,4a-propanobenzo[7]annulen-2(1H)-one; Deposition No. 1589653; 3 pages.
Alam, et al., Synthesis of Adjacent Quaternary Stereocenters by Catalytic Asymmetric Allylboration; J. Am. Chem. Soc.; 2015, 137, 11262-11265.

* cited by examiner

*Primary Examiner* — Noble E Jarrell
*Assistant Examiner* — John S Kenyon
(74) *Attorney, Agent, or Firm* — BakerHostetler

(57) ABSTRACT

The present disclosure provides processes for preparing (+)-pleuromutilin and synthetic (+)-pleuromutilin produced therefrom. Also provided are intermediates prepared thereby and processes for preparing these intermediates.

25 Claims, No Drawings

PROCESS FOR PREPARING PLEUROMUTILIN

CROSS REFERENCE TO RELATED APPLICATIONS

This application claims the benefit of U.S. Provisional Patent Application No. 62/571,117, filed Oct. 11, 2017 and U.S. Provisional Patent Application No. 62/599,886, filed Dec. 18, 2017, the disclosures of which are hereby incorporated by reference in their entireties.

GOVERNMENT RIGHTS

This invention was made with government support under Contract No. GM117764 awarded by the National Institutes of Health. The government has certain rights in the invention.

TECHNICAL FIELD

The present disclosure relates to processes for preparing pleuromutilin.

BACKGROUND (+)-Pleuromutilin (1) is a diterpene natural product first isolated from the fungus *Clitopilus passeckerianus* in 1951. (+)-Pleuromutilin binds to the peptidyl transferase center of bacterial ribosomes, preventing protein synthesis, and thus is active against many clinical isolates such as methicillin-resistant *Staphylococcus Aureus* (MRSA), *Mycoplasma hominis, Mycobacterium tuberculosis*, and *Streptopcoccus pyogenes*. Semi-synthetic derivatives of pleuromutilin in which the C14 ester is modified have been identified as potent antibiotics.

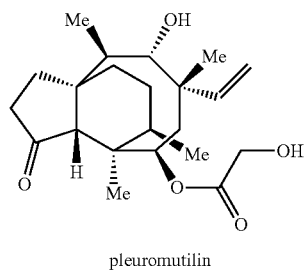

pleuromutilin

Given its promising antibacterial properties, four total syntheses of (+)-pleuromutilin have been reported, to date.

However, pleuromutilin's complex molecule structure presents challenges to its chemical synthesis. New synthetic routes to pleuromutilin are needed.

SUMMARY

The present disclosure provides processes comprising contacting a compound of Formula I with samarium(II) iodide in an organic solvent for a time and under conditions effective to produce a compound of Formula II

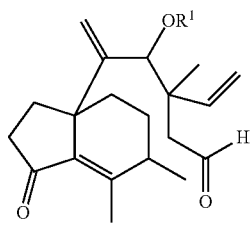

(I)

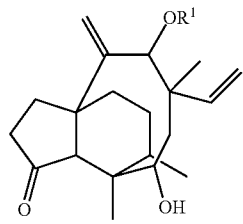

(II)

wherein $R^1$ is H or an oxygen protecting group.

The present disclosure also provides (+)-pleuromutilin produced using a process described herein.

The present disclosure further provides novel intermediates, such as those for the preparation of pleuromutilin, for example, a compound that is:

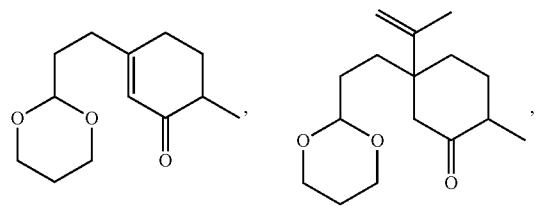

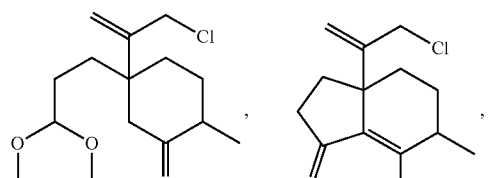

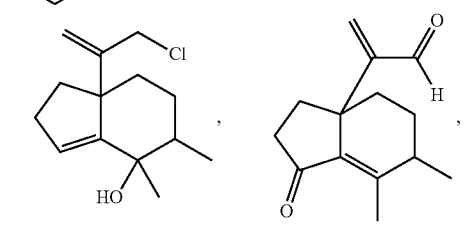

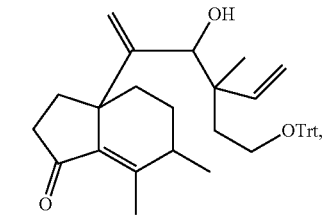

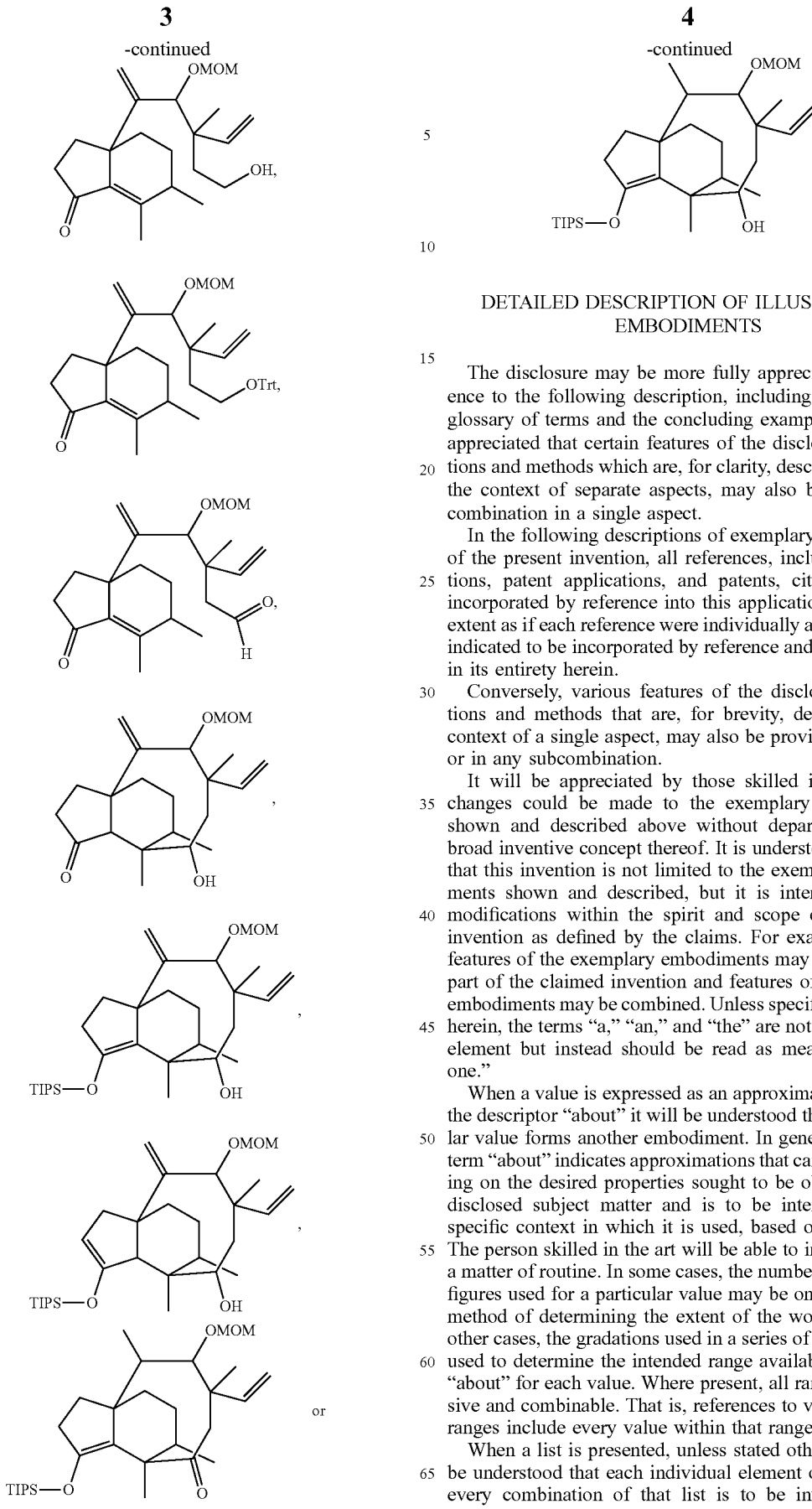

DETAILED DESCRIPTION OF ILLUSTRATIVE EMBODIMENTS

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect.

In the following descriptions of exemplary embodiments of the present invention, all references, including publications, patent applications, and patents, cited herein are incorporated by reference into this application to the same extent as if each reference were individually and specifically indicated to be incorporated by reference and were set forth in its entirety herein.

Conversely, various features of the disclosed compositions and methods that are, for brevity, described in the context of a single aspect, may also be provided separately or in any subcombination.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a," "an," and "the" are not limited to one element but instead should be read as meaning "at least one."

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about". In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

When a range of carbon atoms is used herein, for example, $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

The term "alkyl" refers to a straight-chain or branched-chain or cyclic alkyl group having from 1 to 12 carbon atoms. Alkyl moieties preferably have from 1 to 10 carbon atoms ("$C_{1-10}$"), preferably 1 to 6 carbon atoms ("$C_{1-6}$"), in the chain. Examples of alkyl groups include methyl (Me, $C_1$alkyl) ethyl (Et, $C_2$alkyl), n-propyl ($^n$Pr, $C_3$alkyl), isopropyl ($^i$Pr, $C_3$alkyl), butyl (Bu, $C_4$alkyl), isobutyl ($^i$Bu, $C_4$alkyl), sec-butyl ($^s$Bu, $C_4$alkyl), tert-butyl (Bu, $C_4$alkyl), pentyl ($C_5$alkyl), isopentyl ($C_5$alkyl), tert-pentyl ($C_5$alkyl), hexyl ($C_6$alkyl), isohexyl ($C_6$alkyl), isopinocampheyl ($C_{10}$alkyl), and groups that in light of the ordinary skill in the art and the teachings provided herein would be considered equivalent to any one of the foregoing examples. The alkyl group may be optionally substituted by one or more halogen, $C_{3-8}$cycloalkyl, or aryl. In some aspects, an alkyl group may be substituted by one or more phenyl groups, for example 3 phenyl groups (e.g., —$C(C_6H_5)_3$).

"Aryl" refers to an aromatic radical with six to ten ring atoms which has at least one ring having a conjugated pi electron system which is carbocyclic (e.g., phenyl, fluorenyl, and naphthyl). The term includes monocyclic or fused ring polycyclic (i.e., rings which share adjacent pairs of ring atoms) groups.

"Heteroaryl" refers to a 5- to 18-membered aromatic radical (e.g., ($C_{5-18}$)heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may contain 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. An N-containing "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl).

"Equivalent," as used herein, is the amount of one substance that reacts with one mole of another substance.

"Isomers" are different compounds that have the same molecular formula. "Stereoisomers" are isomers that differ only in the way the atoms are arranged in space, i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror images of each other. The absolute stereochemistry is specified according to the Cahn-Ingold-Prelog "R-S" system. Certain of the compounds described herein contain one or more asymmetric centers and can thus give rise to enantiomers, diastereomers, and other stereoisomeric forms that can be defined, in terms of absolute stereochemistry, as (R) or (S). Unless otherwise noted, pharmaceutical compositions, and methods are meant to include all such possible isomers, including single stereoisomers, racemic mixtures, diastereomeric mixtures, and intermediate mixtures. Optically active (R)- and (S)-isomers can be prepared using chiral synthons or chiral reagents, or resolved using conventional techniques. Methods of determining relative and absolute stereochemistry of compounds described herein are known in the art.

The term "pleuromutilin" as used herein refers to a compound having the general structure:

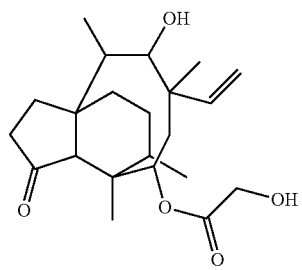 [SMILES: C=CC1(C)CC(OC(=O)CO)C2(C)C(C)CCC3(CCC(=O)C32)C(C)C1O]

A preferred pleuromutilin is

Another preferred pleuromutilin is (+)-Pleuromutilin has the following structure:

Another preferred pleuromutilin of the disclosure is

The numbering described herein may be based on the following:

The disclosure is also directed to derivatives, salts, prodrugs, solvates, and hydrates of pleuromutilin that may be prepared using the one or of the steps described herein, in combination with the knowledge of those skilled in the art. Thus, the disclosure includes the following derivatives, which may be prepared by modifying the 2-hydroxyacetate at the 14-position using methods known in the art:

(+)-mutilin tiamulin

Valnemulin lefamulin

The term "12-epi-pleuromutilin" refers to isomeric mixtures and all purified isomers of a pleuromutilin, wherein the stereochemistry at C12 differs from that occurring in (+)-pleuromutilin. One embodiment of 12-epi-pleuromutilin has the following structure:

Derivatives, salts, prodrugs, solvates, and hydrates of 12-epi-pleuromutilin are also within the scope of the disclosure and may be prepared using the one or more of the steps described herein, along with the knowledge of those skilled in the art. Such compounds include, for example:

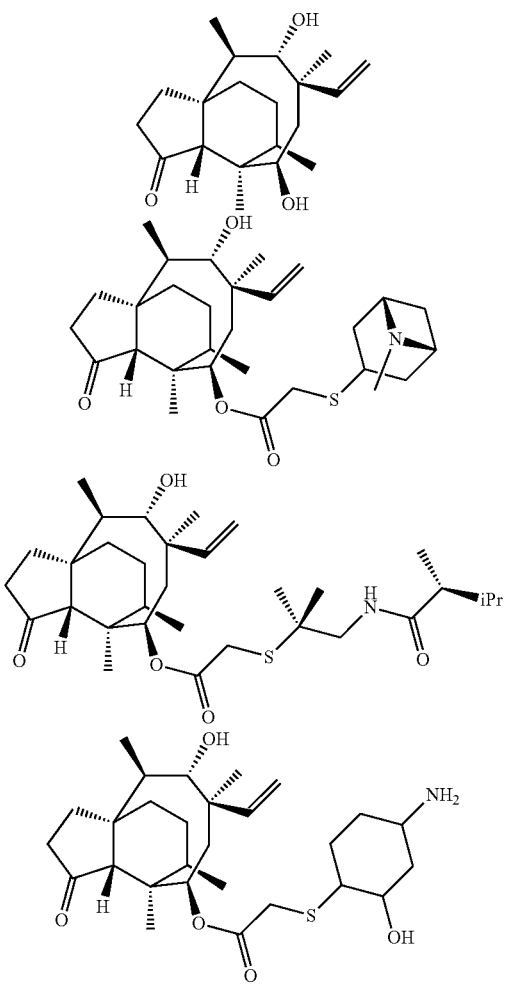

Synthetic Methods

Processes for preparing compounds of Formula II from compounds of Formula I are provided, wherein R¹ is H or an oxygen protecting group. The processes comprise a step of forming the 8-membered ring of compounds of Formula II. This step includes contacting a compound of Formula I with samarium(II) iodide in an organic solvent for a time and under conditions effective to produce a compound of Formula II.

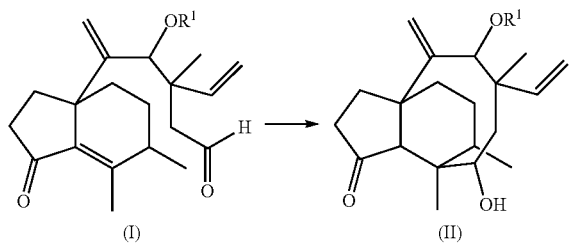

In some embodiments, IV is H. In other embodiments, IV is an oxygen protecting group. Exemplary oxygen protecting groups are known in the art. See, e.g., Greene and Wuts, "Greene's Protective Groups in Organic Synthesis," Fourth Ed., John Wiley & Sons, Inc., 2007, incorporated by reference herein. In some embodiments, the oxygen protecting group is methoxymethyl ($CH_3$—O—$CH_2$—, "MOM"), tetrahydropyranyl, t-butyl, allyl, benzyl, silyl, acetyl, pivaloyl, trityl, or benzoyl. In preferred embodiments, the oxygen protecting group is -MOM.

In some aspects, a molar excess of the samarium(II) iodide ($SmI_2$) is used. That is, according to the disclosure, more than 1 mole of samarium (II) iodide per 1 mole of the compound of Formula I is used. In some embodiments, the processes comprise greater than about 2 moles of samarium (II) iodide per 1 mole of the compound of Formula I. In other embodiments, the reaction comprises about 2.5 to about 3.5 moles of samarium(II) iodide per 1 mole of the compound of Formula I. In further embodiments, the reaction comprises, about 2.5, about 2.6, about 2.7, about 2.8, about 2.9, about 3.0, about 3.1, about 3.2, about 3.3, about 3.4, or about 3.5 moles of samarium(II) iodide per 1 mole of the compound of Formula I. Preferably, about 3 mol of samarium(II) iodide per 1 mole of the compound of Formula I are utilized. In preferred aspects, the $SmI_2$ is added in portions, i.e., not all at once, over time.

According to the methods of the disclosure, the compounds of Formula II are prepared under conditions that are anaerobic. The term "anaerobic" as used herein refers to the substantial absence of oxygen, that is, having less than 0.5 ppm of oxygen, preferably, less than 0.4 or less than 0.3 or less than 0.2 or less than 0.1 ppm of oxygen. Preferably, the reaction vessel is protected from ambient oxygen. More preferably, the reagents and reaction mixture can be deoxygenated prior to the combination of reagents. Methods of deoxygenating reagents and reaction mixtures are known in the art and include, for example, adding reagents that selectively react with oxygen or bubbling of another gas, for example, nitrogen, argon, for hydrogen, through the reagents and/or reaction mixture, at a flow rate and for a time sufficient to deoxygenate the reagents/reaction mixture.

According to the methods of the disclosure, the compounds of Formula I are contacted with samarium(II) iodide in an organic solvent. In some embodiments, the organic solvent is a polar organic solvent or a mixture of polar organic solvents. In other embodiments, the organic solvent comprises an ethereal solvent. Exemplary organic solvents include cyclic ethers such as tetrahydrofuran, without limitation. In other aspects, the solvent is tetrahydrofuran, ethyl ether, dichloromethane, ethyl acetate, acetone, dimethylformamide, acetonitrile, dimethylsulfoxide, or a combination thereof.

The reaction mixtures to produce compounds of Formula II further comprise water, preferably deoxygenated water. The water may be miscible with the organic solvent/mixture of organic solvents. In some aspects, the addition of water has been observed to minimize the formation of side-products. In other aspects, the addition of water has been observed to increase the diastereoselectivity of the reaction forming the compound of Formula II. In some embodiments, the water is in a molar excess, as compared to the compound of Formula I. That is, more than 1 mol of water is used for every 1 mol of the compound of Formula I. In other embodiments, at least about 2 mol of water are used, based on 1 mol of the compound of Formula I. In further embodiments, about 2 to about 20, about 2 to about 15, about 2 to about 10, about 2 to about 8, about 4 to about 8 mol of water are used. In still other embodiments, at least about 1.5, about 2, about 3, about 4, about 5, about 6, about 7, about 8, about 9, about 10, about 11, about 12, about 13, about 14, about 15, abut 16, about 17, about 18, about 19, or about 20 mol of water are used.

Preferably, the conversion of the compounds of Formula I to the compounds of Formula II is carried out at a temperature that is below room temperature, i.e., at a temperature that is below 25° C. In some aspects, the temperature of the reaction mixture is about −20° C. to about 20° C. In other embodiments, the temperature of the reaction mixture is about −10 to about 10° C. In further embodiments, the temperature of the reaction mixture is about −5 to about 5° C. In yet other embodiments, the temperature of the reaction mixture is about −10, about −9, about −8, about −7, about −6, about −5, about −4, about −3, about −2, about −1, about 0, about 1, about 2, about 3, about 4, about 5, about 6, about 7, about 8, about 9, or about 10° C., preferably about 0° C.

In some aspects, the compound of Formula I is

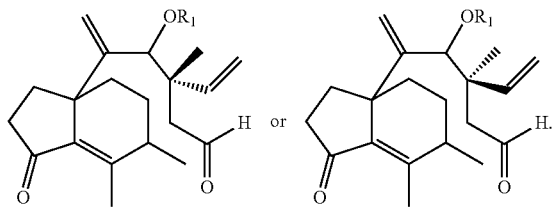

In other aspects, the compound of Formula I is

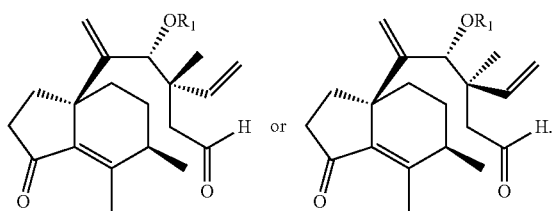

In preferred aspects, the compound of Formula I is

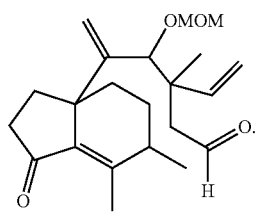

In other preferred aspects, the compound of Formula I is

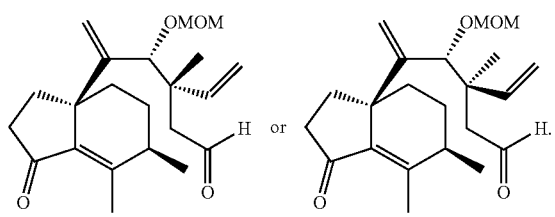

In some aspects, the compound of Formula II is

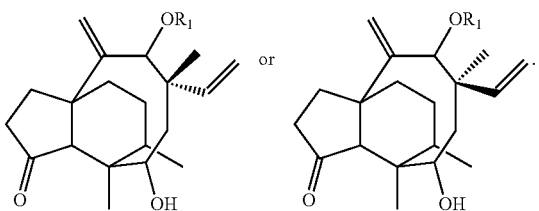

In other aspects, the compound of Formula II is

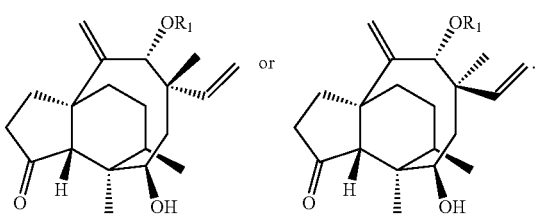

In preferred aspects, the compound of Formula II is

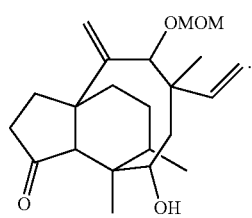

In other preferred aspects, the compound of Formula II is

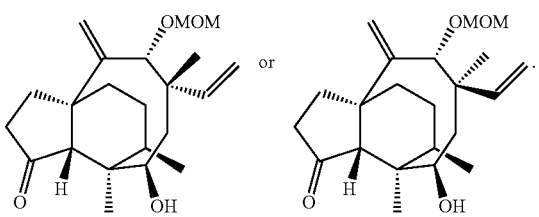

In an exemplary transformation, a compound of Formula I, in aqueous THF is treated with about 2.5 to about 3.5 equivalents, preferably 3 equivalents, of $SmI_2$ under an inert atmosphere for a time sufficient to form a cyclic, samarium (III) intermediate.

While not wishing to bound to any particular theory, it is believed that a cyclic samarium (III) intermediate is of the formula:

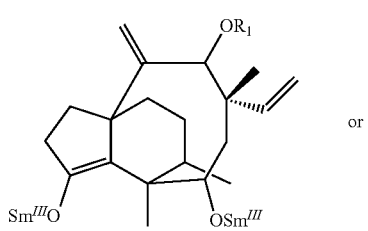

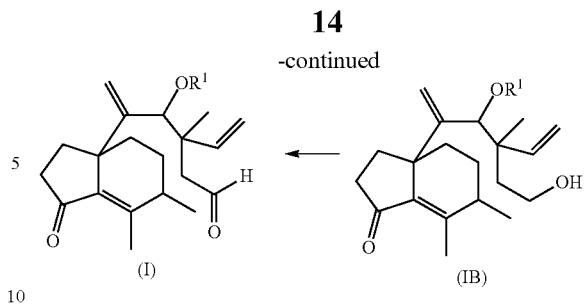

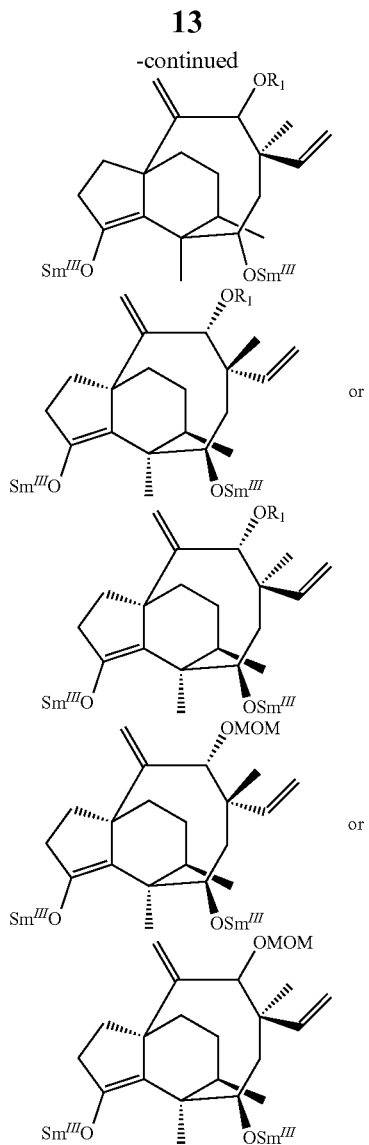

Treatment of the reaction mixture, e.g., the samarium (III) intermediate with a molar excess of an alkylsilyl halide, for example, trimethylsilyl chloride, relative to the moles of a compound of Formula I, produces the compound of Formula II.

According to the methods of the disclosure, the compounds of Formula I may be prepared from a compound of Formula III. An exemplary synthetic route to compounds of Formula I from compounds of Formula III is shown below.

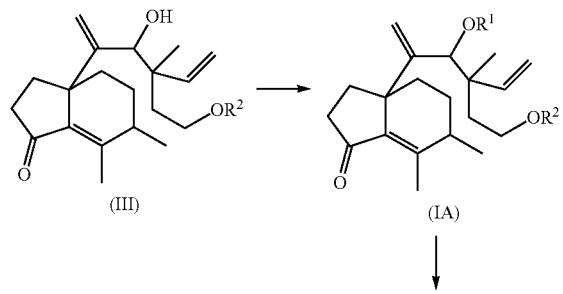

According to the disclosure, the compound of Formula III is contacted with an oxygen protecting group reagent, in the presence of an organic solvent, for example, an aprotic, polar organic solvent to form a compound of Formula IA. According to the disclosure, $R^2$ is an oxygen protecting group that is an orthogonal protecting group, as compared to $R^1$. As used herein, "orthogonal protecting groups" are protecting groups wherein the reaction conditions that will provide for the deprotection of one protecting group, are insufficient to also remove the other protecting groups(s). Exemplary oxygen protecting groups that are known in the art to be orthogonal to the $R^1$ protecting groups described herein are known in the art. See, e.g., Wuts and Greene cited above. See, e.g., Greene and Wuts, "Greene's Protective Groups in Organic Synthesis," Fourth Ed., John Wiley & Sons, Inc., 2007. In some embodiments, the orthogonal oxygen protecting group is triphenyl methyl (trityl, Trt).

The term "oxygen protecting group reagent" as used herein refers to a chemical compound that contains an oxygen protecting group as one moiety of the reagent and a leaving group (i.e., an $S_N2$ leaving group) as the other moiety of the reagent. Preferably, the oxygen protecting group reagent contains the $R^1$ group. Exemplary oxygen protecting group reagents are known in the art. See, e.g., Greene and Wuts, "Greene's Protective Groups in Organic Synthesis," Fourth Ed., John Wiley & Sons, Inc., 2007. In some embodiments, the oxygen protecting group reagent is methoxymethyl chloride (MOMCl).

Desirably, a molar excess of the oxygen protecting reagent is utilized. In certain embodiments, about 2 to about 50 equivalents, for example, about 5 to about 40, about 10 to about 30, about 20 to about 25, or about 20, about 21, about 22, about 23, about 24, about 25, about 26, about 27, about 28, about 29, or about 30, preferably about 25 equivalents, of the oxygen protecting group agent are utilized.

The reaction to prepare a compound of Formula IA is performed in the presence of a base, such as an amine base. For example, the base can be a trialkyl amine base such as diisopropylethylamine, triisopropylamine, trimethylamine, or trimethylamine, or mixtures thereof may be utilized. Preferably, the base comprises or is diisopropylethylamine. Preferably, the base is utilized in a molar excess, as compared to the compound of Formula III. In certain embodiments, about 2 to about 50 equivalents, for example, about 5 to about 40, about 10 to about 30, about 20 to about 25, or about 20, about 21, about 22, about 23, about 24, about 25, about 26, about 27, about 28, about 29, or about 30, preferably about 25 equivalents, of the base are utilized.

In some aspects, the compound of Formula IA is a compound of the formula:

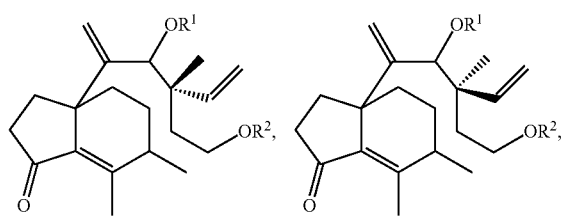

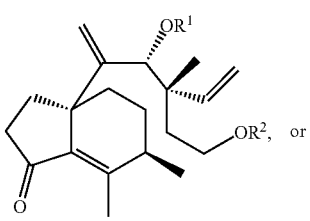

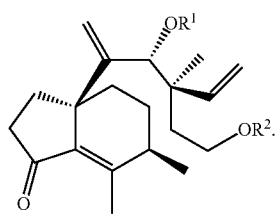

In some embodiments, the compound of Formula IA is a compound of Formula IA-1a or IA-1b:

(IA-1a)

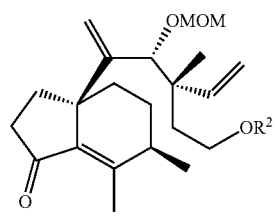

(IA-1b)

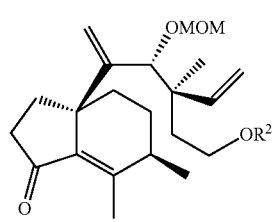

wherein $R^2$ is as defined herein.

In other embodiments, the compound of Formula IA is a compound of Formula IA-2a or IA-2b:

(IA-2a)

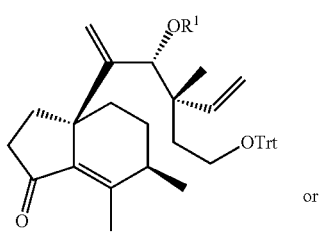

or (IA-2b)

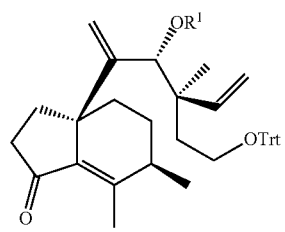

wherein $R^1$ is as defined herein.

In preferred embodiments, the compound of Formula IA is

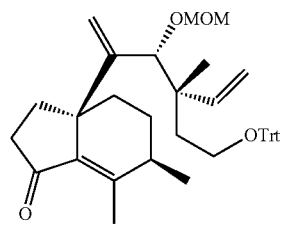

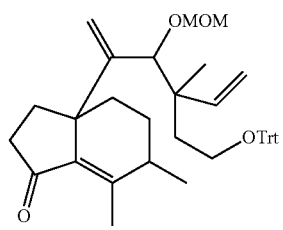

or

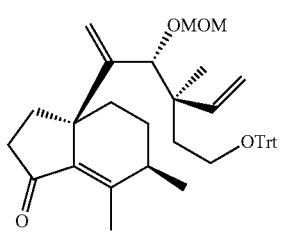

In an exemplary transformation, a compound of Formula III in dichloromethane is treated with diisopropylethylamine and chloromethyl methyl ether to form the compound of Formula I.

The compound of Formula IA is subjected to conditions effective to produce a compound of Formula IB. An exemplary synthetic scheme is summarized below.

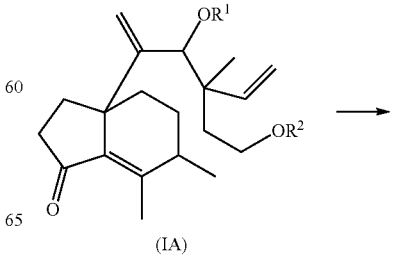

(IA)

-continued

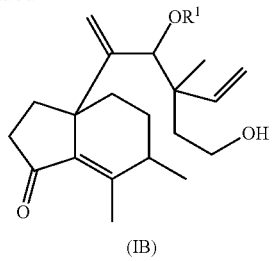

(IB)

In some embodiments, the compound of Formula IB is

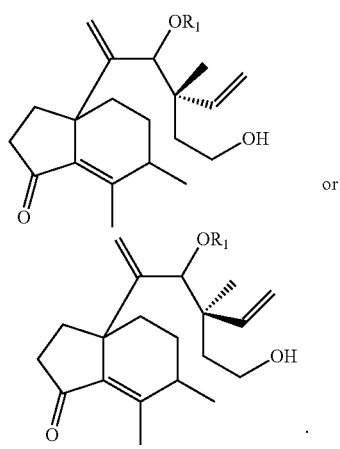

or

In other embodiments, the compound of Formula IB is

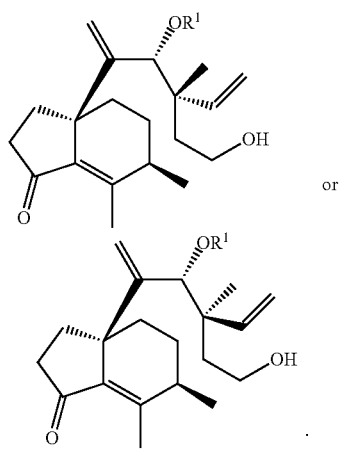

In preferred aspects, the compound of Formula IB is

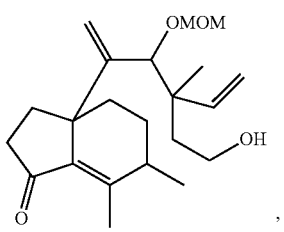

,

-continued

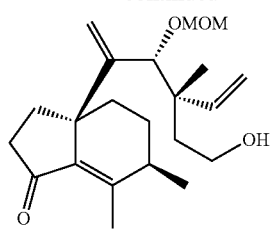

or

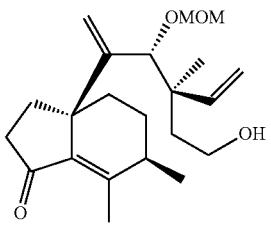

According to the methods described herein, the conditions that are effective to convert the compound of Formula IA to the compound of Formula IB include performing the reaction with in the presence of an acid, for example, formic acid. Alcoholic solvents, for example, methanol, ethanol, propanol, preferably ethanol, and aliphatic ethers such as diethylether, dimethylether, methylethylether, preferably diethylether, and mixtures thereof, are preferred solvents.

In an exemplary transformation, a compound of Formula IA is treated with formic acid in diethylether to provide the compound of Formula IB.

According to the disclosure, the compounds of Formula IB are oxidized under conditions sufficient to produce the compounds of Formula I.

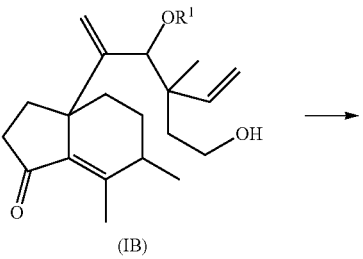

(IB)

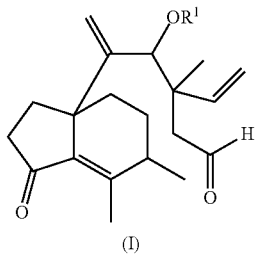

(I)

Preferred compounds of Formula IB include, for example:

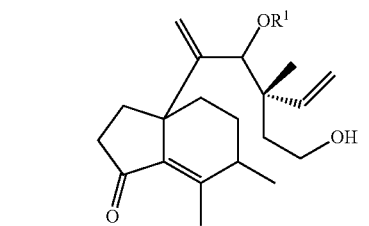

and

-continued

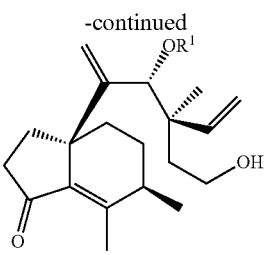

The oxidizing conditions required to effect this transformation comprise, for example, the oxidation conditions as described in Steves and Stahl, J. Am. Chem. Soc., 2013, 135, 15742, which is incorporated by reference herein. In some embodiments, the oxidation conditions comprise a copper catalyst such as [Cu(MeCN)$_4$]OTf or CuCu(OTf)$_2$, preferably [Cu(MeCN)$_4$]OTf. In other embodiments, the conditions required to effect this transformation include a bipyridine analog such as bipyridine or 4-OMe-bipyridine, preferably 4-OMe-bipyridine. In further embodiments, the oxidation conditions comprise a copper complex formed from the copper catalyst and bipyridine analog. The conditions required to effect this transformation may also include a nitro oxide radical catalyst such as 9-azabicyclo[3.3.1]nonane N-oxyl (ABNO) or (2,2,6,6-tetramethylpiperidin-1-yl)oxyl (TEMPO), preferably ABNO. In some preferred embodiments, the oxidation conditions also comprise N-methylimidazole (NMI). Suitable organic solvents include, for example, polar hydrocarbon solvents such as acetonitrile and toluene. Acetonitrile is one preferred solvent. Other oxidizing conditions are known in the art.

In an exemplary transformation, a compound of Formula IB in acetonitrile is treated with [Cu(MeCN)$_4$]OTf, 4-methoxy-bipyridine, ABNO, and NMI to provide the compound of Formula I. Desirably, a solution comprising [Cu(MeCN)$_4$]OTf and 4-methoxy-bipyridine is added first, followed by NMI, and then ABNO.

According to the methods described herein, the compounds of Formula III may be prepared by contacting a compound of Formula A with a compound of Formula IVa or IVb:

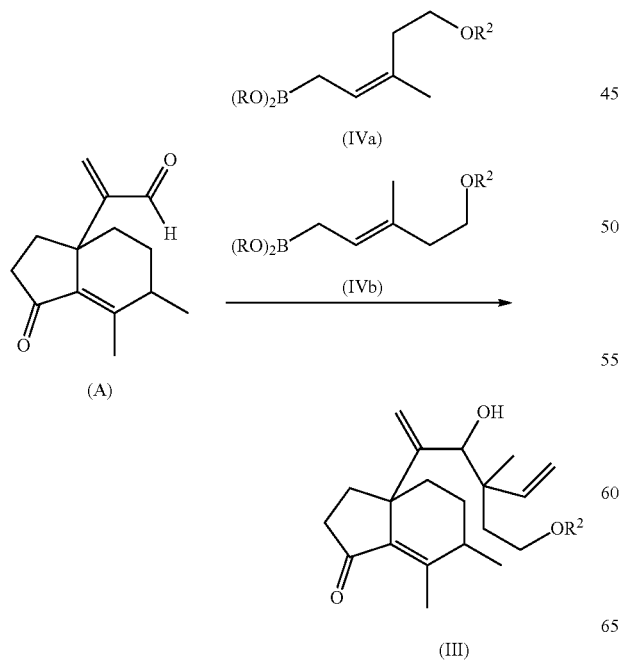

In some embodiments, the compound of Formula A is contacted with the compound of Formula IVa. In other embodiments, the compound of Formula A is contacted with the compound of Formula IVb. According to the disclosure, R is H or C$_{1-10}$alkyl or each R, together with the carbons to which they are attached, forms a cyclic boronic ester moiety. Preferably, R is H.

In the compounds of Formula IVa and IVb, R$^2$ is H or R$^2$ is an oxygen protecting group that is an orthogonal protecting group, as compared to R$^1$. In some embodiments, R$^2$ is H. In other embodiments, R$^2$ is methyl substituted with 3 phenyl groups, i.e., a trityl group (C(Ph$_3$)). Preferably, the compound of Formula IVa is

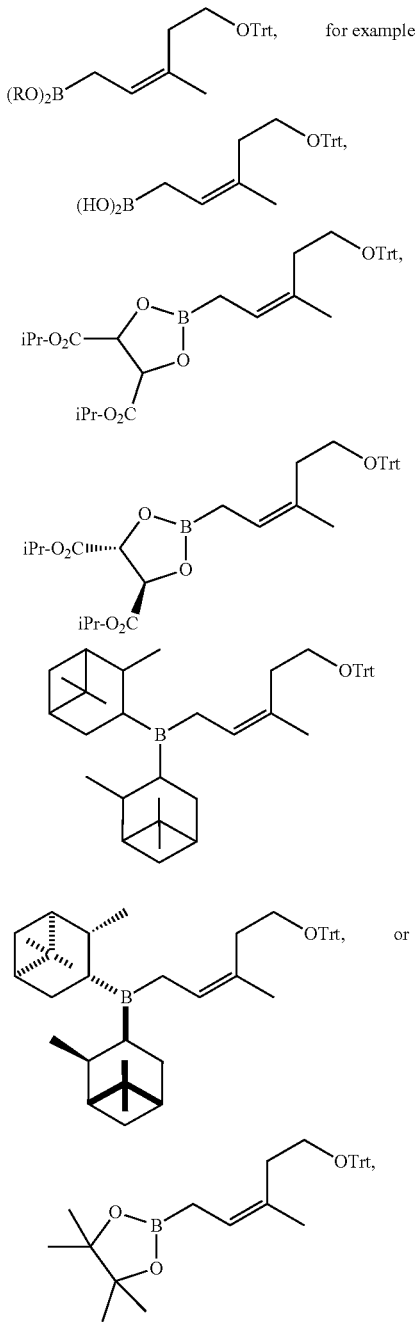

preferably

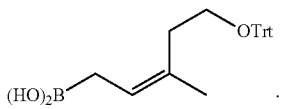

Preferably, the compound of Formula IVb is

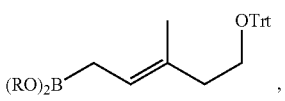

for example,

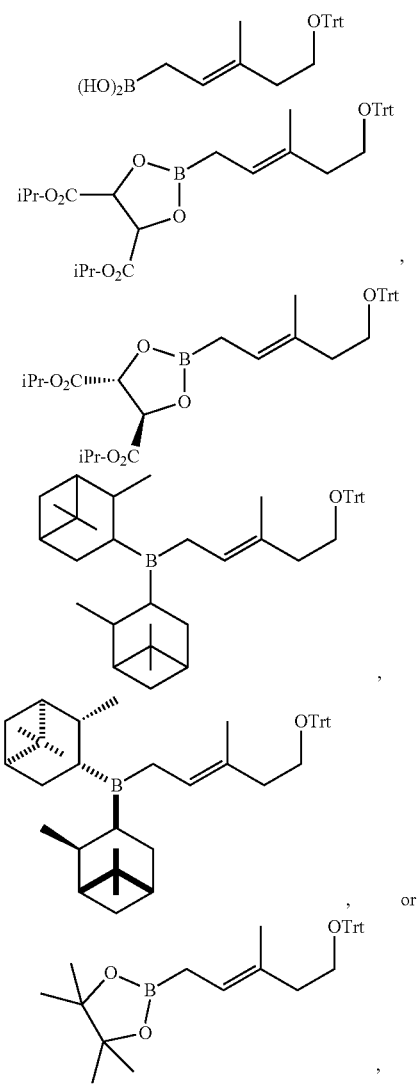

preferably

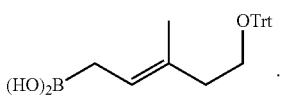

According to the methods described herein, the compounds of Formula IVa may be prepared via a 4-step process, wherein R2 is defined herein and R is, independently, H or $C_{1-6}$alkyl or R, together with the atoms to which they are attached, forms a cyclic boronic ester moiety.

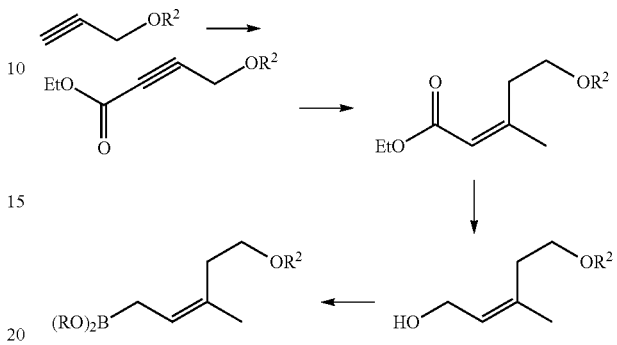

As a first step, 3-butyl-1-ol is trityl protected using transformations known in the art. In some embodiments, 3-butyn-1-ol is treated with in the presence of a coupling reagent, such as, for example 4-dimethylaminopyridine (DMP), 1-hydroxy-1H-benzotriazole, or 1-hydroxy-1H-azabenzotrilae, preferably DMAP. In some embodiments, at least about 1.5 equivalents, about 2 equivalents, about 3 equivalents, about 4 equivalents, about 5 equivalents, about 6 equivalents, about 7 equivalents, about 8 equivalents, about 9 equivalents, or about 10 equivalents, preferably at least about 6 equivalents, of the coupling reagent are utilized. The reaction is performed in a polar organic solvent, such as dichloromethane. Addition of a base and trityl chloride afforded the product. For example a trialkyl amine base such as diisopropylethylamine, triisopropylamine, trimethylamine, or trimethylamine, or mixtures thereof may be utilized. Preferably, the base comprises or is triethylamine. In some embodiments, at least about 1.1 equivalents, about 1.2 equivalents, about 1.3 equivalents, about 1.4 equivalents, about 1.5 equivalents, about 1.6 equivalents, about 1.7 equivalents, about 1.8 equivalents, about 1.9 equivalents, about 2 equivalents, about 2.5 equivalents, about 3 equivalents, about 3.5 equivalents, or about 4 equivalents, preferably at least about 2 equivalents, of the trialkylamine are utilized.

In an exemplary transformation, 3-butyl-1-ol in dichloromethane is treated with trityl chloride, trimethylamine and DMAP to provide the trityl intermediate.

The corresponding alkanoate ester is then prepared from the trityl intermediate.

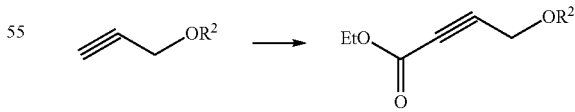

The conditions required to effect the transformation include treating the trityl protected intermediate with a strong base, followed by ethylchloroformate. In some embodiments, at least about 1.5 equivalents, about 2 equivalents, about 2.5 equivalents, about 3 equivalents, about 3.5 equivalents, or about 4 equivalents, preferably at least about 3 equivalents, of the ethylchloroformate are utilized. The strong base is preferably lithium diisopropylamide. Desirably, the transformation is performed under anhydrous conditions. Such anhydrous conditions may include the use of inert gases, such as nitrogen or argon, and/or anhydrous reagents such as dried solvents. Suitable solvents ethereal solvents, in particular, cyclic ethers such as tetrahydrofuran. The transformation can take place at any suitable temperature, for example, ambient temperature or below. Suitable temperatures may include, for example, about 20, 15, 10, 5, 0, −5, −10, −15, −20, −25, −30, −40, −50, −60, −70 or about −80° C., preferably about −70 to about −80° C., preferably less than −20° C., preferably less than −50° C.

In an exemplary transformation, the trityl intermediate is treated with lithium diisopropylamide and ethylchloroformate at reduced temperatures to provide the alkanoate ester. Desirably, the trityl intermediate is treated with lithium diisopropylamide, followed by ethylchloroformate at reduced temperatures such as about −70 to about −80° C. to provide the alkanoate ester.

According to the methods described herein, the alkanoate ester is then converted to the corresponding acrylate via a methyl conjugate addition.

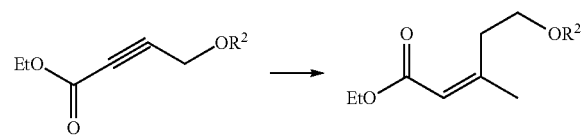

Preferably, the alkanoate ester is reacted with a Gilman reagent, such as Me$_2$CuLi. The Gilman reagent may be prepared using skill in the art. In some embodiments, the Gilman reagent used herein is prepared using CuI and MeLi, preferably an excess of MeLi such as at least about 1.5 equivalents, about 2 equivalents, about 2.5 equivalents, about 3 equivalents, about 3.5 equivalents, or about 4 equivalents, preferably at least about 2 equivalents. Desirably, the transformation is performed under anhydrous conditions. Such anhydrous conditions may include the use of inert gases, such as nitrogen or argon, and/or anhydrous reagents such as dried solvents. Suitable solvents ethereal solvents, in particular, cyclic ethers such as tetrahydrofuran. The transformation can take place at any suitable temperature, for example, ambient temperature or below. Suitable temperatures may include, for example, about 20, 15, 10, 5, 0, −5, −10, −15, −20, −25, −30, −40, −50, −60, −70 or about −80° C., preferably about −70 to about −80° C., preferably less than −20° C., preferably less than −50° C.

In an exemplary transformation, the alkanoate ester is treated with Me$_2$CuLi at reduced temperatures to provide the acrylate. Desirably, the alkanoate ester is added to a solution containing copper iodide and methyl lithium at reduced temperatures such as about −70 to about −80° C. to provide the acrylate.

According to the methods described herein, the acrylate is then reduced to the corresponding alcohol.

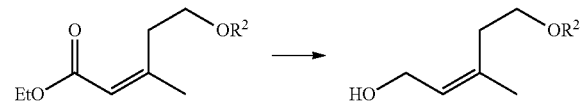

The reduction may be performed using a strong reducing agent, preferably a bulky reducing agent. In some embodiments, the reducing agent is di-isobutyl aluminum hydride (DIBAL-H), lithium aluminum hydride (LAH), or LiAl(O$^t$Bu)$_3$H, preferably DIBAL-H. Preferably, the strong reducing agent is used in an excess, for example, greater than about 5 equivalents, based on the acrylate. In some embodiments, the reaction is performed with at least about 10, about 25, about 50, about 75, about 100, about 125, about 150, about 160, or about 170 equivalents, preferably about 150 equivalents, of the strong reducing agent. Desirably, the transformation is performed under anhydrous conditions. Such anhydrous conditions may include the use of inert gases, such as nitrogen or argon, and/or anhydrous reagents such as dried solvents. Suitable solvents include dichloromethane. The transformation can take place at any suitable temperature, for example, ambient temperature or below. Suitable temperatures may include, for example, about 20, 15, 10, 5, 0, −5, −10, −15, −20, −25, −30, −40, −50, −60, −70 or about −80° C., preferably about −70 to about −80° C., preferably less than −20° C., preferably less than −50° C.

In an exemplary transformation, the acrylate is treated with DIBAL in dichloromethane at reduced temperatures such as about −70 to about −80° C. to provide the alcohol.

According to the methods described herein, the alkyl boronic acid is then prepared from the alcohol. See, e.g., Szabó described above.

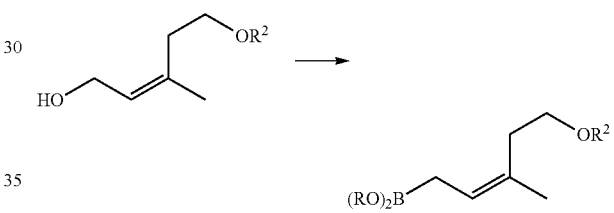

This transformation may be performed using a palladium catalyst and a boron source. The palladium catalyst that may be used to effect the transformation includes Pd(OAc)$_2$, Pd$_2$(dba)$_3$, or Pd(MeCN)$_4$(BF$_4$)$_2$, preferably Pd(MeCN)$_4$(BF$_4$)$_2$. A catalytic amount of the palladium catalyst, such as at least about a 5 mol %, 10 mol %, 20 mol %, 30 mol %, 40 mol %, 50 mol %, 60 mol %, preferably about 10 mol %, is used. The boron source may include tetrahydroxydiboron or bis(pinacolato)diboron, preferably tetrahydroxydiboron. Equal equivalents of the boron source, based on the acrylate, or a slight excess of the boron source may be used. In some embodiments, about 1 equivalent, at least about 1 equivalent, about 1.1, about 1.2, about 1.3, about 1.4, about 1.5, or about 2 equivalents, preferably about 1.2 equivalents of the boron source are utilized. A highly polar organic solvent such as DMSO, DMF, DMA, or benzonitrile, preferably DMSO, may be used. Desirably, the transformation is performed under anhydrous conditions. Such anhydrous conditions may include the use of inert gases, such as nitrogen or argon, and/or anhydrous reagents such as dried solvents. Suitable solvents include aromatic solvents, for example, toluene. The transformation can take place at any suitable temperature, for example, ambient temperature.

In an exemplary transformation, the alcohol is treated with a slight excess, of tetrahydroxydiboron, Pd(MeCN)$_4$(BF$_4$)$_2$ in DMSO to provide the boronic acid.

According to the methods described herein, the compound of Formula IVb may also be prepared via a 4-step process, wherein R and R$^2$ are defined herein.

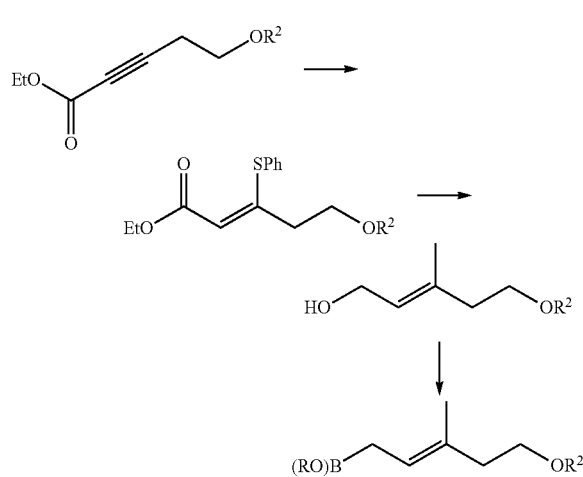

The initial steps includes converting the alkynone ester to the corresponding thiolacrylate:

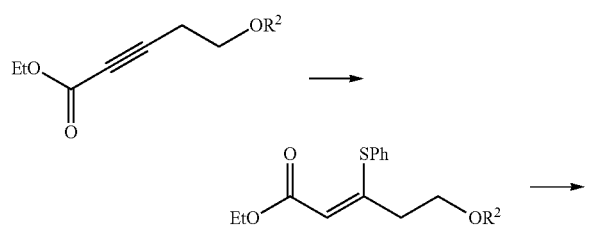

The alkynone ester is first treated with thiophenol in the presence of a weak base, preferably sodium methoxide, in an organic solvent. Suitable solvents include alcoholic solvents such as, for example, methanol, ethanol, propanol, t-butanol, and mixtures thereof, preferably methanol. Preferably the transformation is performed in under anhydrous conditions including the use of inert gases, such as nitrogen or argon.

In an exemplary transformation, the alkynone ester is treated with NaOMe, and thiophenol to provide the thiolacrylate.

According to the methods described herein, the thiolacrylate is then converted to the corresponding alcohol.

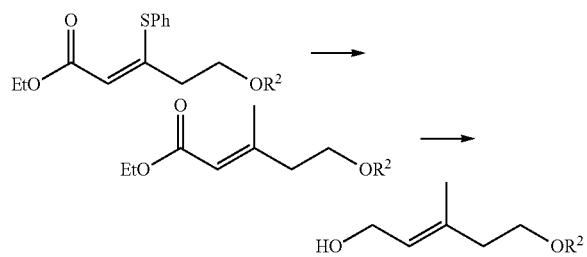

The first step includes a substitution reaction, wherein the thiophenol moiety is substituted with a methyl group. Preferably, the alkanoate ester is reacted with a Gilman reagent, such as Me$_2$CuLi. The Gilman reagent may be prepared using skill in the art. In some embodiments, the Gilman reagent used herein is prepared using CuI and MeMgBr. Preferably, an excess of one or both of Cu and MeMgBr are utilized. In some embodiments, an excess of MeMgBr is used, such as at least about 1.1 equivalents, about 1.2 equivalents, about 1.3 equivalents, about 1.4 equivalents, 1.5 equivalents, or about 2 equivalents, preferably at least about 1.2 equivalents. In other embodiments, an excess of CuI is used, such as at least about 1.1 equivalents, about 1.2 equivalents, about 1.3 equivalents, about 1.4 equivalents, 1.5 equivalents, or about 2 equivalents, preferably at least about 1.2 equivalents. Desirably, the transformation is performed under anhydrous conditions. Such anhydrous conditions may include the use of inert gases, such as nitrogen or argon, and/or anhydrous reagents such as dried solvents. Suitable solvents ethereal solvents, in particular, cyclic ethers such as tetrahydrofuran. The transformation can take place at any suitable temperature, for example, ambient temperature or below. Suitable temperatures may include, for example, about 20, 15, 10, 5, 0, −5, −10, −15, −20, −25, −30, −40, −50, −60, −70 or about −80° C., preferably about −70 to about −80° C., preferably less than −20° C., preferably less than −50° C.

The second step includes reducing the acrylate to the alcohol. reduction may be performed using a strong reducing agent, preferably a bulky reducing agent. In some embodiments, the reducing agent is di-isobutyl aluminum hydride (DIBAL-H), lithium aluminum hydride (LAH), or LiAl(O$^t$Bu)$_3$H, preferably DIBAL-H. Preferably, the strong reducing agent is used in an excess, for example, greater than about 5 equivalents, based on the acrylate. In some embodiments, the reaction is performed with at least about 2, about 3, about 4, about 5, about 6, about 7, about 8, about 9, or about 10, preferably about 4 equivalents, of the strong reducing agent. Desirably, the transformation is performed under anhydrous conditions. Such anhydrous conditions may include the use of inert gases, such as nitrogen or argon, and/or anhydrous reagents such as dried solvents. Suitable solvents include dichloromethane, hydrocarbons (e.g., hexanes), or mixtures thereof. The transformation can take place at any suitable temperature, for example, ambient temperature or below. Suitable temperatures may include, for example, about 20, 15, 10, 5, 0, −5, −10, −15, −20, −25, −30, −40, −50, −60, −70 or about −80° C., preferably about −70 to about −80° C., preferably less than −20° C., preferably less than −50° C.

In an exemplary transformation, the thiolacrylate is treated with copper iodide and methylmagnesium bromide, in THF at reduced temperatures. The acrylate intermediate is then treated with DIBAL-H at reduced temperatures to provide the corresponding alcohol.

According to the methods described herein, the alcohol is converted to the boronic acid of Formula IVb:

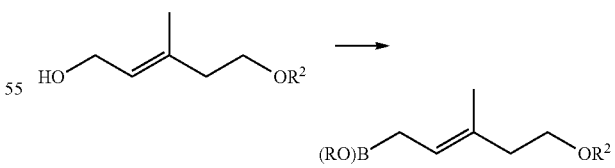

This transformation may be performed using a palladium catalyst and a boron source. See, e.g., Szabo described above. The palladium catalyst that may be used to effect the transformation includes Pd(OAc)$_2$, Pd$_2$(dba)$_3$, or Pd(MeCN)$_4$(BF$_4$)$_2$, preferably Pd(MeCN)$_4$(BF$_4$)$_2$. A catalytic amount of the palladium catalyst, such as at least about a 5 mol %, 10 mol %, 20 mol %, 30 mol %, 40 mol %, 50 mol %, 60 mol %, preferably about 10 mol %, is used. The boron source may include tetrahydroxydiboron or bis(pinacolato) diboron, preferably tetrahydroxydiboron. Equal equivalents of the boron source, based on the acrylate, or a slight excess of the boron source may be used. In some embodiments, about 1 equivalent, at least about 1 equivalent, about 1.1, about 1.2, about 1.3, about 1.4, about 1.5, or about 2 equivalents, preferably about 1.2 equivalents of the boron source are utilized. A highly polar organic solvent such as DMSO, DMF, DMA, or benzonitrile, preferably DMSO, may be used. Desirably, the transformation is performed under anhydrous conditions. Such anhydrous conditions may include the use of inert gases, such as nitrogen or argon, and/or anhydrous reagents such as dried solvents. Suitable solvents include aromatic solvents, for example, toluene. The transformation can take place at any suitable temperature, for example, ambient temperature.

In an exemplary transformation, the alcohol is treated with tetrahydroxydiboron in the presence of Pd(MeCN)$_4$(BF$_4$)$_2$ in DMSO to provide the trityl reagent of Formula IVb.

According to the methods described herein, the transformation to the compounds of Formula III is performed in the presence of a catalyst such as (R)-3,3'-Br$_2$-BINOL, (S)-3,3'-Br$_2$-BINOL, (R)-(+)-3,3'-bis(3,5-bis(trifluoromethyl)phenyl)-1,1'-bi-2-naphthol, 2,2',3,3'-tetrahydro-1,1'-spirobi[indene]-4,4'-diol, (R)-VANOL (3,3'-diphenyl-2,2'-bi-1-naphthalol), or (R)-VAPOL (2,2'-diphenyl-3,3'-(4-biphenanthrol)), preferably (R)-3,3'-BINOL-Br$_2$. See, e.g., Alam, Vollgraff, Eriksson, Szabó, J. Am. Chem. Soc. 2015, 137, 11262, which is herein incorporated by reference. In preferred aspects, the reaction is carried out under substantially anhydrous conditions, for example, the reaction mixture includes 1% of less (v/v) of water.

The catalyst can be present in an amount of from 1 mol % to about 50 mol %, 5 mol % to about 40 mol %, 10 mol % to about 30 mol %, 15 mol % to about 25 mol %, or 17 mol % to about 22 mol %. Preferably, about 20 mol % of the catalyst is used.

According to the disclosure, the contacting is performed in an organic solvent under conditions sufficient to produce the compound of Formula III. Suitable solvents include hydrocarbons (e.g., hexanes) and aromatic solvents, for example, toluene, or mixtures thereof, with one or more alcoholic solvents such as, for example, methanol, ethanol, propanol, t-butanol, and mixtures thereof. Preferably, the organic solvent is a mixture of toluene and t-butanol.

The preparation of the compounds of Formula III can take place at ambient temperature or below, for example, about 20, 15, 10, 5, 0, −5, −10, −15, or about −20° C. Preferably, the compounds of Formula III are prepared at reduced temperatures such as −20 to about 20° C., −10 to about 10° C., about −5 to about 5° C., or about 0° C.

Desirably, the transformation is performed under anhydrous conditions. Such anhydrous conditions may include the use of inert gases, such as nitrogen or argon, and/or drying agents that may be added to the reaction mixture and/or reagents. For example, molecular sieves can be added to the solvent. Preferably, 3 or 4 Å molecular sieves are utilized.

In preferred embodiments, the compounds of Formula III are prepared having a diastereomeric excess of about 20% to about 99%. For example, in preferred aspects, the diastereomeric excess is at least about 20%, preferably at least about 30%, at least about 40, at least about 50%, at least about 60%, at least about 70%, at least about 80%, at least about 90%, or at least about 99%.

In some embodiments, the compound of Formula III is

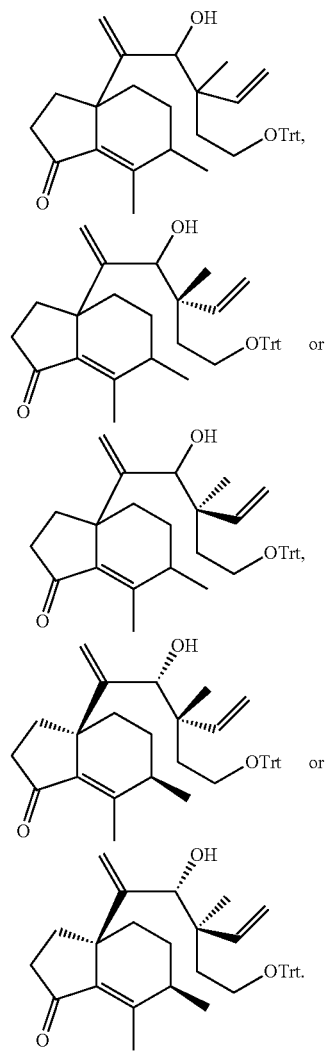

In an exemplary transformation, a compound of Formula A is treated with a compound of Formula IVa (or a compound of Formula IVb), 20 mol % of (R)-3,3'-Br$_2$-BINOL, t-butanol, and toluene at 0° C., for a time sufficient to form the compound of Formula III.

According to the disclosure, pleuromutilin may be prepared from the compounds of Formula II through a sequence of further synthetic steps. As such, the compounds of Formula II can be subjected to conditions effective to produce compounds of Formula V, Formula VA, or a combination thereof

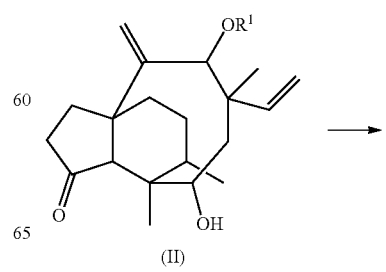

(II)

-continued

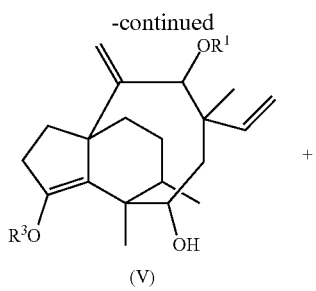
(V)

+

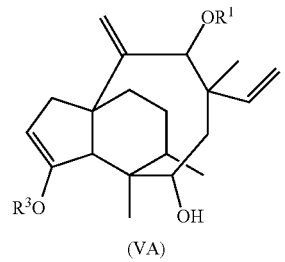
(VA)

In these compounds of Formula V or VA, $R^3$ is a silyl protecting group. In some embodiments, $R^3$ is triisopropylsilyl (TIPS), trimethylsilyl (TMS), tert-butyldiphenylsilyl (TBDPS), and tert-butyldimethylsilyl (TBDMS), preferably TIPS. The $R^3$ group is orthogonal to the $R^1$ protecting group of the compound of Formula V or VA. The conditions effective to produce the compound of Formula V or VA include the conversion of the compound of Formula II to a silyl enol ether of Formula V or VA. The reaction is preferably performed in the presence of a base such as, for example, potassium hexamethyldisilazide, lithium hexamethyldisilazide, or sodium hexamethyldisilazide, preferably lithium hexamethyldisilazide. The base can be present in a molar excess, preferably, an amount of from about 1.1 mol % to about 10 mol %, about 1.5 to about 7 mol %, about 1.7 to about 5 mol %, about 2 mol % to about 5 mol %, about 2 mol % to about 4 mol %, about 3 mol % to about 5 mol %, or about 3 mol % to about 4 mol %. Preferably, about 3 mol % of the base is used.

The reaction also is performed using an $R^3$ protecting group reagent that that provides an $R^3$ group that is orthogonal to the $R^1$ protecting group. In some embodiments, the $R^3$ protecting group reagent is triisopropylsilyl triflate, triisopropylsilyl chloride, or dimethylhexylsilyl chloride, preferably triisopropylsilyl triflate. The $R^3$ protecting group reagent can be present in a molar excess, preferably, an amount of from about 1.1 mol % to about 10 mol %, about 1.5 to about 7 mol %, about 1.7 to about 5 mol %, about 2 mol % to about 5 mol %, about 2 mol % to about 4 mol %, or about 2 mol % to about 3 mol %. Preferably, about 2 mol % of the base is used. The base may be added at a rate that results in the compounds of Formula V or VA.

Suitable solvents for the preparation of compounds of Formula V or VA include ethereal solvents, in particular, cyclic ethers such as tetrahydrofuran. The transformation can take place at any suitable temperature, for example, ambient temperature or below. Suitable temperatures may include, for example, about 20, 15, 10, 5, 0, −5, −10, −15, −20, −25, −30, −40, −50, −60, −70 or about −80° C., preferably about −70 to about −80° C., preferably less than −20° C., preferably less than −50° C. Desirably, the transformation is performed under an inert atmosphere, such as argon or nitrogen.

The compounds of Formula V and VA may be isolated and separated using techniques known in the art. Preferably, the compound of Formula V is separated from the compound of Formula VA using chromatography.

In an exemplary transformation, a compound of Formula II is treated with triisopropylsilyltriflate and lithium hexamethyldisilazide in tetrahydrofuran at about −78 to about 0° C. for a time sufficient to produce the compound of Formula V or VA.

In some embodiments, the compound of Formula V is a compound of Formula V-1:

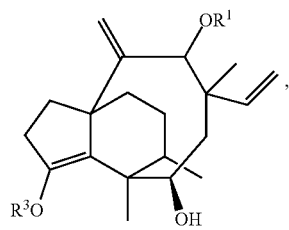

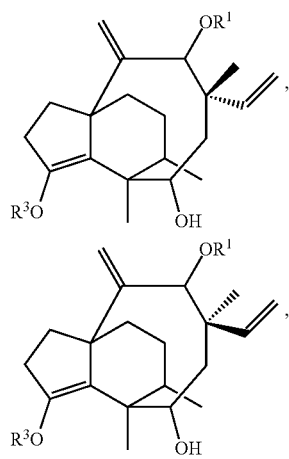

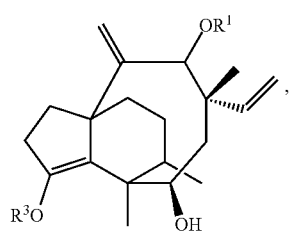

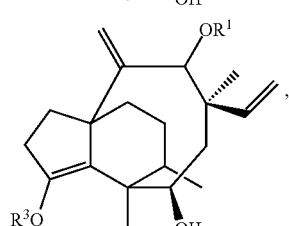

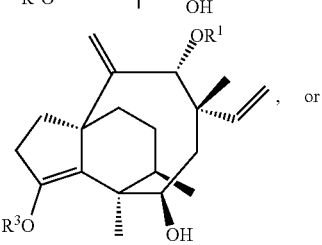
, or

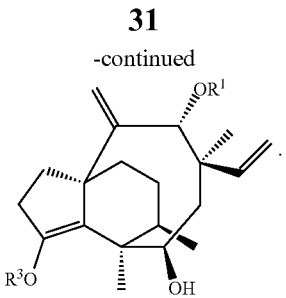
wherein $R^1$ and $R^3$ are defined herein. In other embodiments, the compound of Formula V is a compound of Formula V-2:
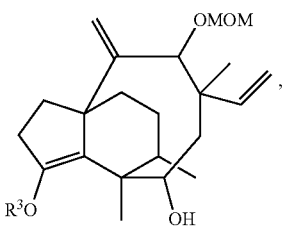
wherein $R^3$ is defined herein, preferably
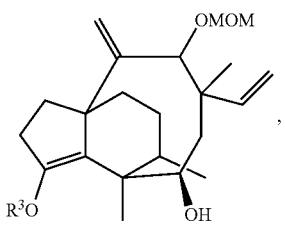
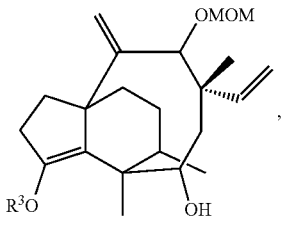
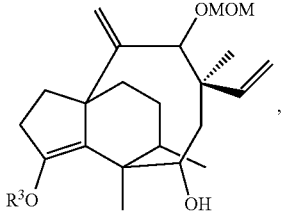
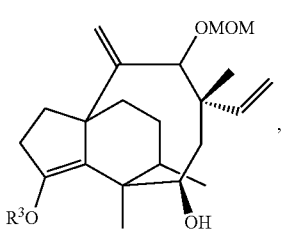
In further embodiments, the compound of Formula V is a compound of Formula V-3
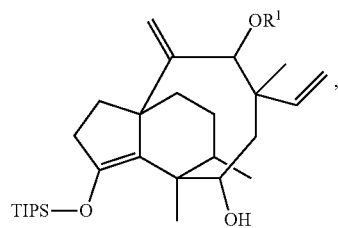
wherein $R^1$ is defined herein, preferably
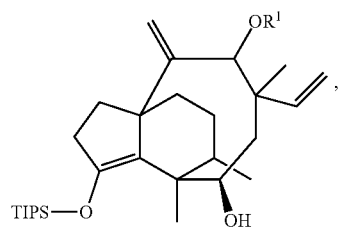
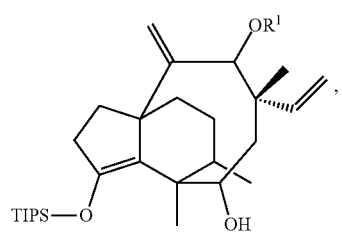

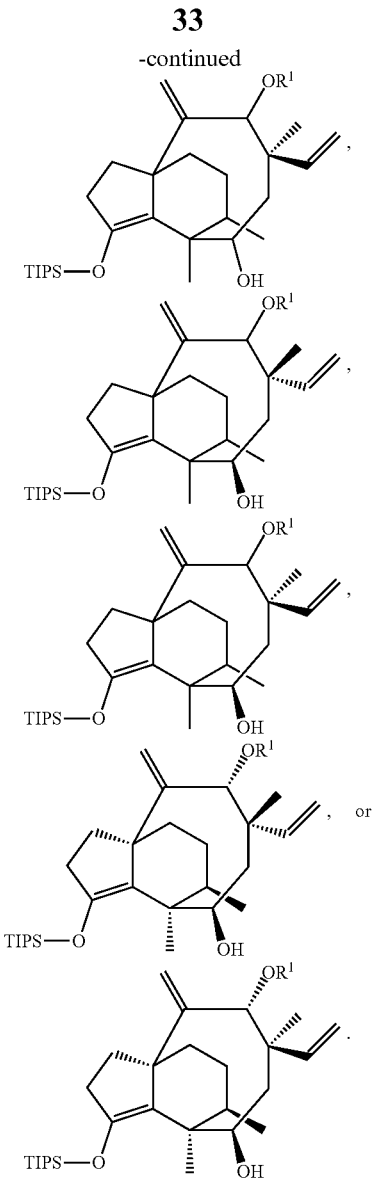
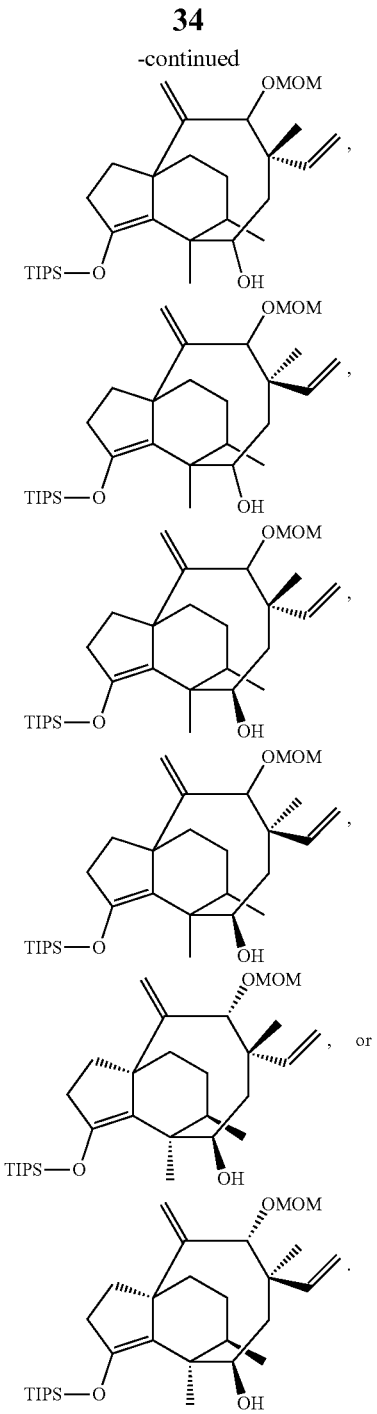
In yet other embodiments, the compound of Formula V is
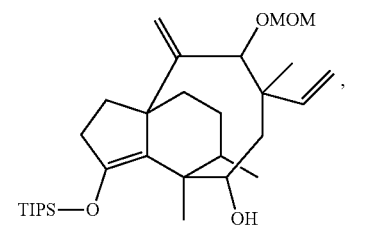
preferably
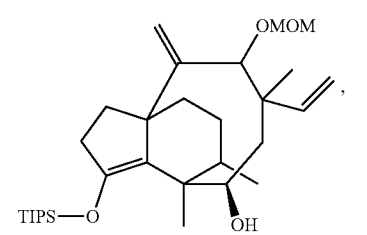
In some embodiments, the compound of Formula VA is a compound of Formula VA-1:
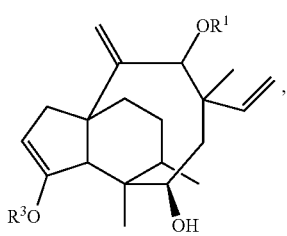

-continued
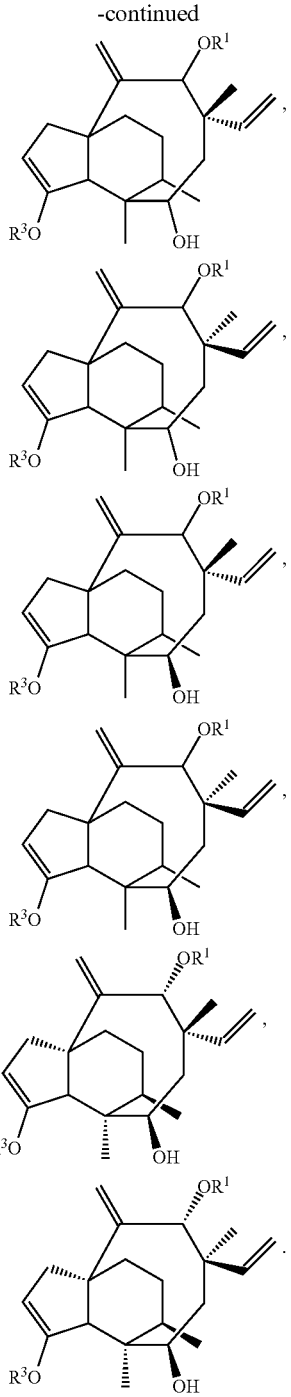
wherein R¹ and R³ are defined herein. In other embodiments, the compound of Formula VA is a compound of Formula VA-2:
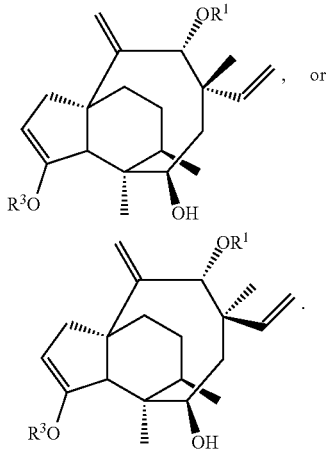
wherein R³ is defined herein, preferably
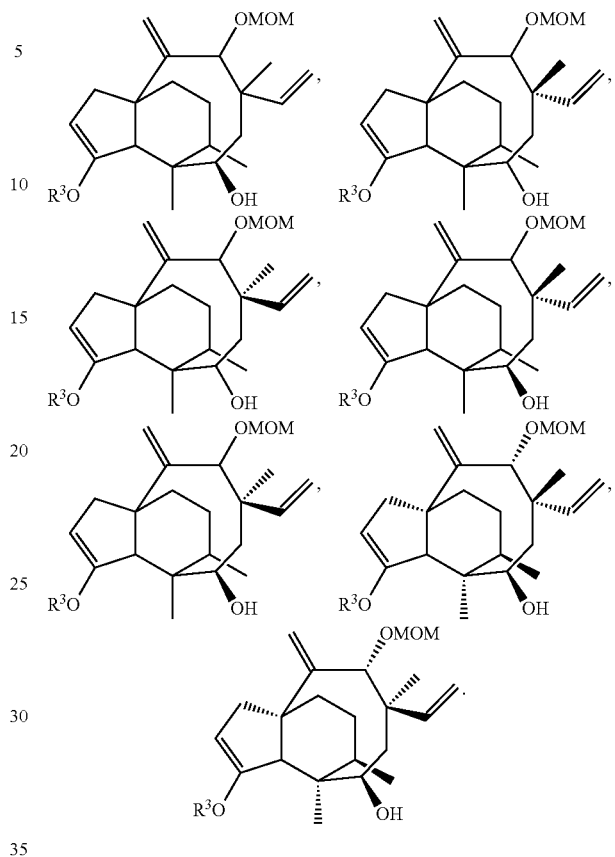
In further embodiments, the compound of Formula VA is a compound of Formula VA-3:
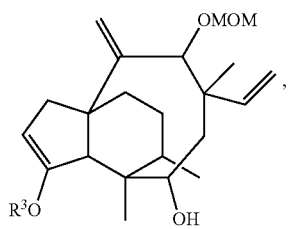
wherein R¹ is defined herein, preferably
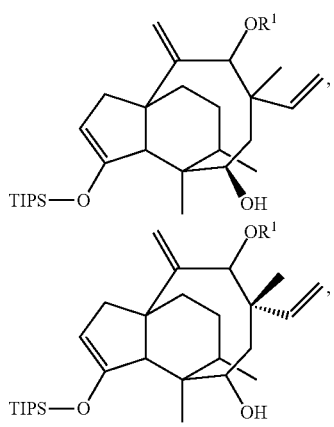

-continued
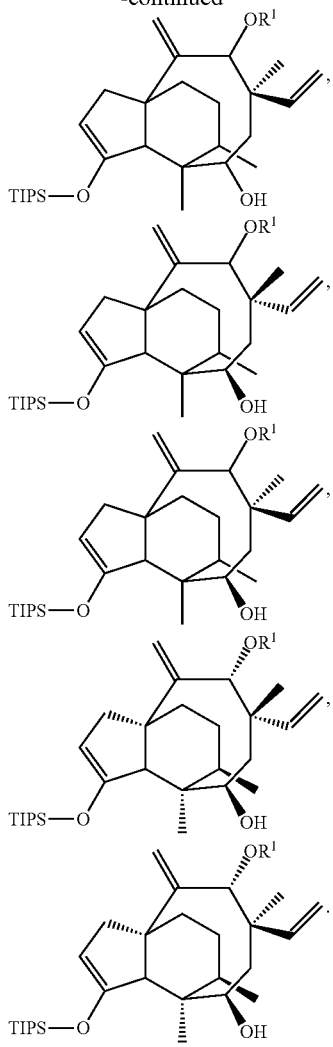
In yet other embodiments, the compound of Formula VA is
preferably
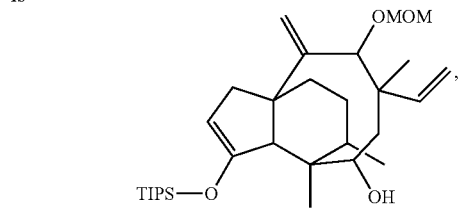
-continued
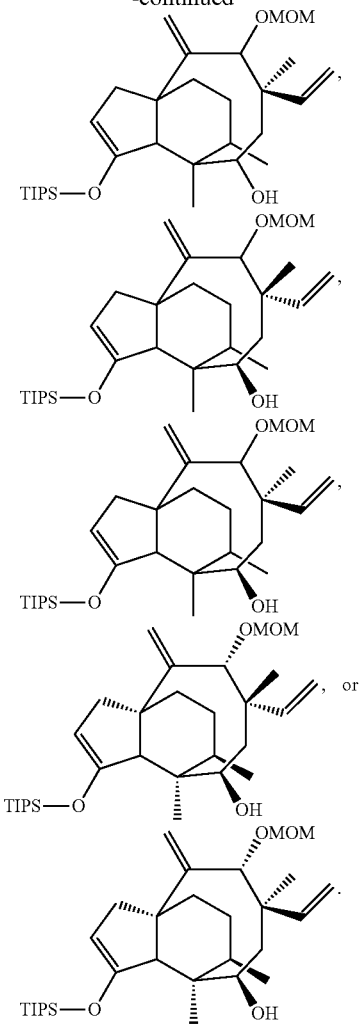
According to the disclosure provided herein, the compounds of Formula V or VA are subjected to conditions sufficient to provide a compound of Formula VI. Desirably, the transformation provides a single diastereomer of the compound of Formula VI.
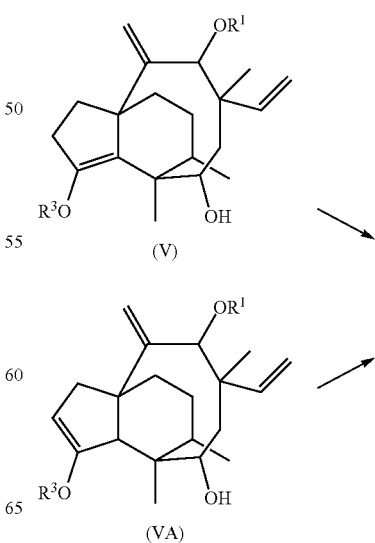

-continued

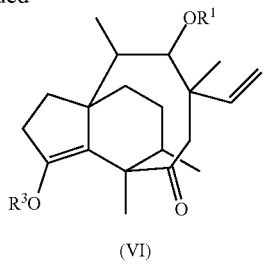

(VI)

The conditions sufficient to provide the compound of Formula VI comprise hydrogen atom transfer conditions. See, e.g., Shenvi (*J. Am. Chem. Soc.* 2014, 136, 1300), which is herein incorporated by reference. The hydrogen atom transfer is performed using a catalyst such as tris(2,2,6,6-tetramethyl-3,5-heptanedionato)manganese (III), tris(2,2,6,6-tetramethyl-3,5-heptanedionato)cobalt (III), or (R,R)-(−)-N,N'-bis(3,5-di-tert-butylsalicylidene)-1,2-cyclohexanediaminocobalt(II) chloride (Co(Salen$^{tBu,tBu}$)Cl), preferably tris(2,2,6,6-tetramethyl-3,5-heptanedionato)manganese (III). A catalytic amount of the catalyst may be used, such as about 2 mol % to about 20 mol %, about 5 mol % to about 15 mol %, or about 10 mol %. The catalyst may be added in one aliquot or 2 or more aliquots, preferably the catalyst is added in several aliquots. In some embodiments, each addition of the catalyst contains the same molar equivalent. In other embodiments, the first addition of the catalyst contains a greater molar equivalence than subsequent additions. In further embodiments, the first addition of the catalyst contains at least about 2 times, preferably at least about 3 times of the amount of catalyst used in the second addition.

Alcoholic solvents, for example, methanol, ethanol, propanol such as isopropanol, and mixtures thereof, are preferred solvents, preferably the solvent is isopropanol. The catalysis is performed in the presence of an aryl silane such as phenylsilane or phenyl-isopropyl-silane, preferably phenylsilane, and an organic peroxide such as tert-butyl hydroperoxide (TBHP). Preferably, each of the aryl silane and organic peroxide are used in a slight excess, for example, greater than about 1.1 equivalents, based on the compound of Formula V. In some embodiments, the reaction is performed with at least about 1.1, about 1.2, about 1.3, about 1.4, about 1.5, about 1.6, about 1.7, about 1.8, about 1.9, about 2, about 3, about 4, or about 5 equivalents, preferably about 1.5 equivalents, of the aryl silane. Similarly, the reaction may be performed with at least about 1.1, about 1.2, about 1.3, about 1.4, about 1.5, about 1.6, about 1.7, about 1.8, about 1.9, about 2, about 3, about 4, or about 5 equivalents, preferably about 2 equivalents, of the organic peroxide.

Desirably, the transformation is performed under anhydrous and inert atmosphere conditions, such as nitrogen or argon. Alcoholic solvents, for example, methanol, ethanol, propanol, aliphatic alkanes such as pentane, hexane, or heptanes, preferably hexane, aryl hydrocarbons such as benzene and toluene, preferably benzene, and mixtures thereof, are preferred solvents for the conversion to the compounds of Formula VI.

As shown below, the inventors found that the combination of Mn(dpm)$_3$ (in several aliquots), PhSiH$_3$, TBHP, and isopropanol provided the highest yield of the desired product.

In some embodiments, the compound of Formula VI is a compound of Formula VI-1:

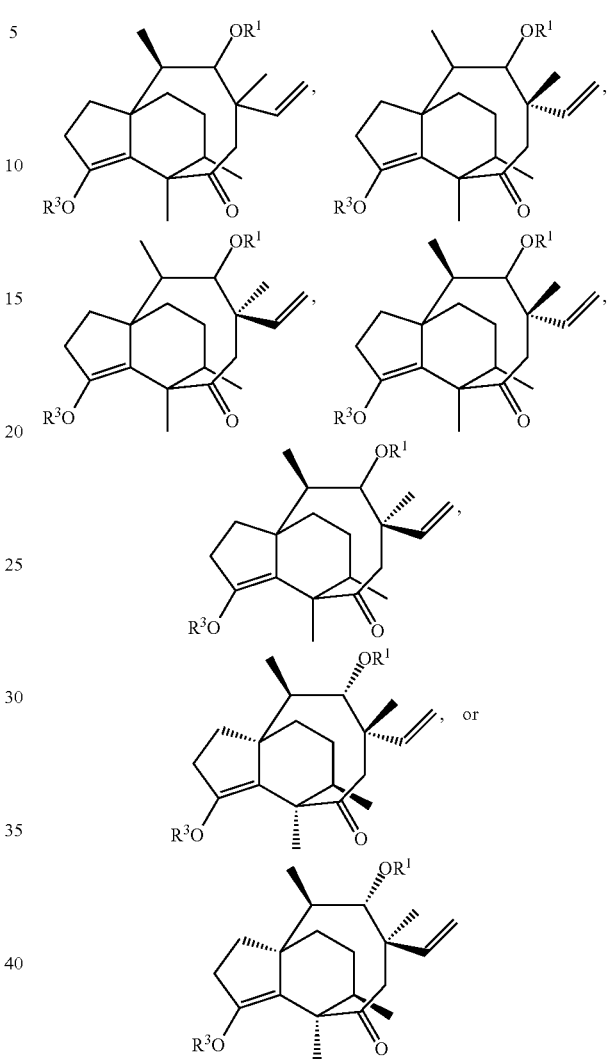

wherein $R^1$ and $R^3$ are defined herein.

In other embodiments, the compound of Formula VI is a compound of Formula VI-2:

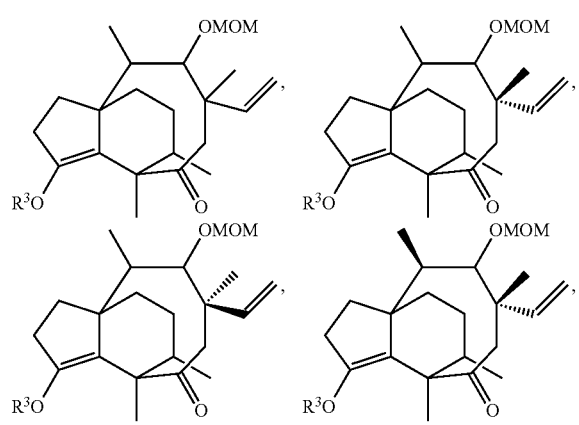

-continued
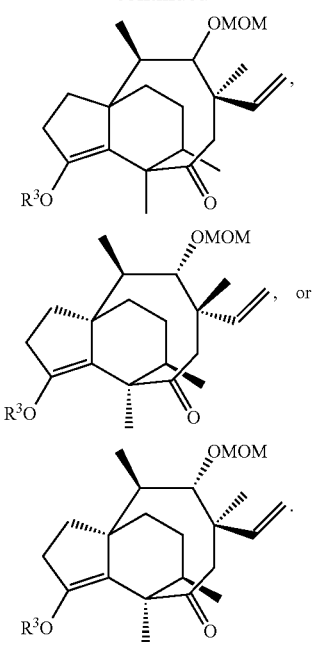
wherein R³ is defined herein, preferably.
In further embodiments, the compound of Formula VI is a compound of Formula VI-4:
-continued
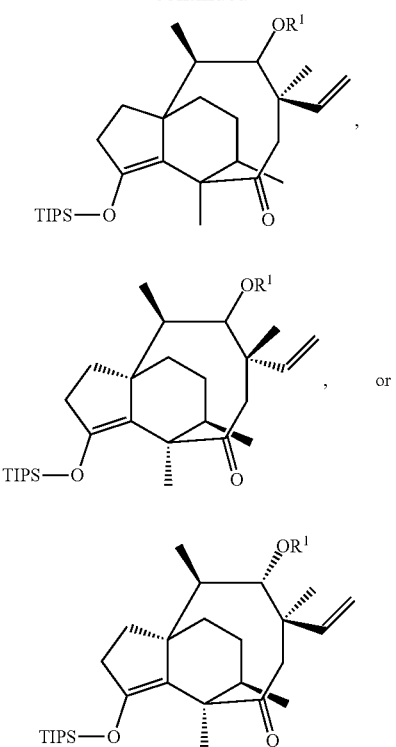
wherein R¹ is defined herein.
In yet other embodiments, the compound of Formula VI is
preferably
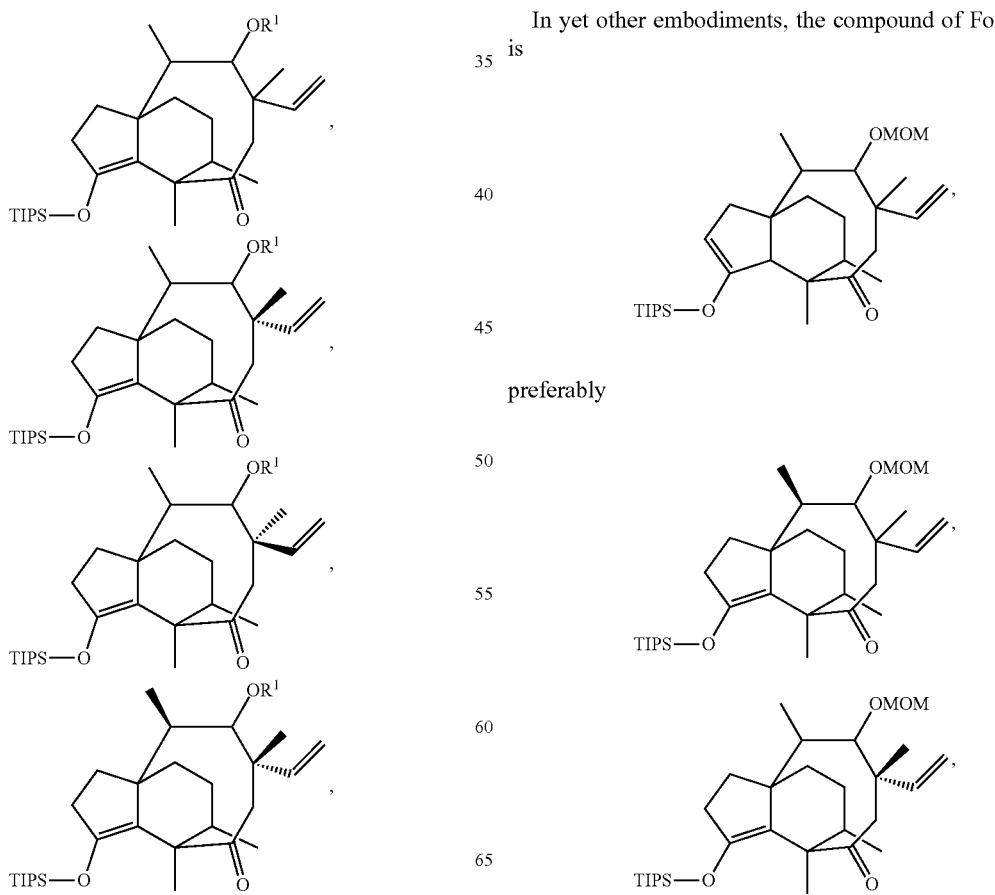

-continued

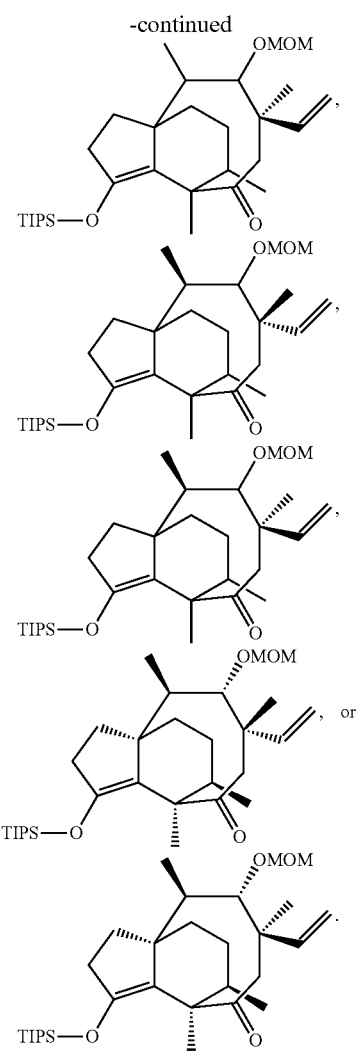

In an exemplary transformation, a compound of Formula V is treated with Mn(dpm)₃, phenylsilane, TBHP in isopropanol at room temperature for a time sufficient to form the compound of Formula VI.

The compounds of Formula VI are then subjected to conditions sufficient to produce compounds of Formula VII.

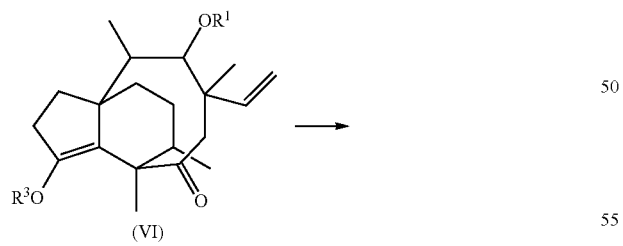

The conditions for such a transformation include reduction of the ketone moiety. The reduction may be performed using, for example, an alkali metal in ammonia. Preferably, the reduction is performed using sodium, lithium, or potassium, more preferably lithium, in ammonia. The reduction can be performed in an aliphatic alcohol such as ethanol or tert-butanol, preferably ethanol, aliphatic ether such as diethylether, dimethylether, methylethylether, preferably diethylether, or mixtures thereof.

The transformation can take place at any suitable temperature, for example, ambient temperature or below. Suitable temperatures may include, for example, about 20, 15, 10, 5, 0, −5, −10, −15, −20, −25, −30, −40, −50, −60, −70 or about −80° C., preferably about −20° C. to about −80° C. or about −70 to about −80° C. Preferably, an excess of the alkali metal is utilized for the reduction, for example, at least about 50, about 100, about 150, about 200, or about 225 equivalents, preferably at least about 20 equivalents, of the alkali metal.

Desirably, the transformation is performed under anhydrous and inert atmosphere conditions, such as nitrogen or argon. Alcoholic solvents, for example, methanol, ethanol, propanol, preferably ethanol, and aliphatic ethers such as diethylether, dimethylether, methylethylether, preferably diethylether, and mixtures thereof, are preferred solvents for the conversion of the compounds of Formula VI to the compounds of Formula VII.

The compounds of Formula VII may be prepared in a diastereomeric excess. For example, the compounds of Formula VII may be prepared in a diastereomeric excess of at least about 5:1, about 6:1, about 7:1, about 8:1, about 9:1, about 10:1, about 11:1, about 12:1, about 13:1, or about 14:1, preferably at least about 14:1.

In some embodiments, the compound of Formula VII is a compound of Formula VII-1:

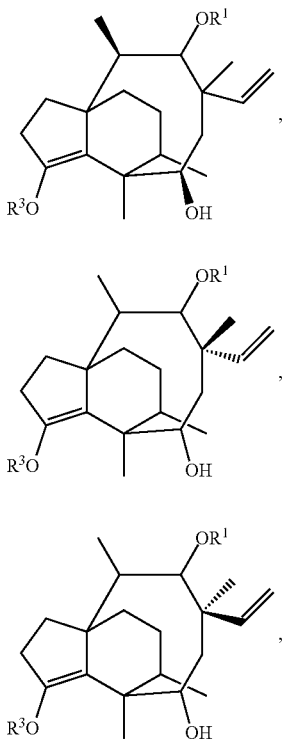

-continued
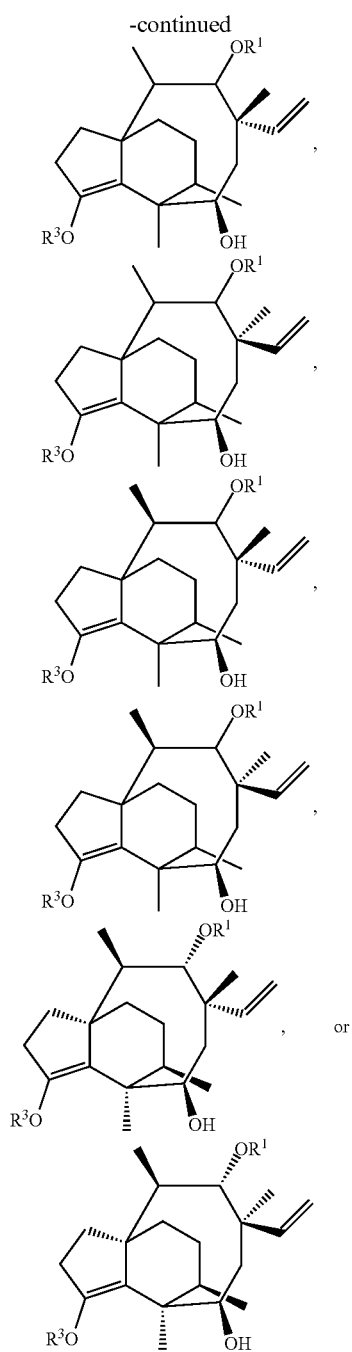
wherein $R^1$ and $R^3$ are defined herein.
In other embodiments, the compound of Formula VII is a compound of Formula VII-2:
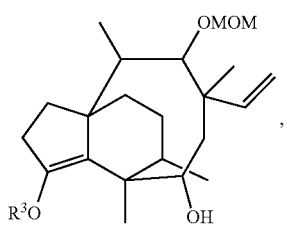, preferably
-continued
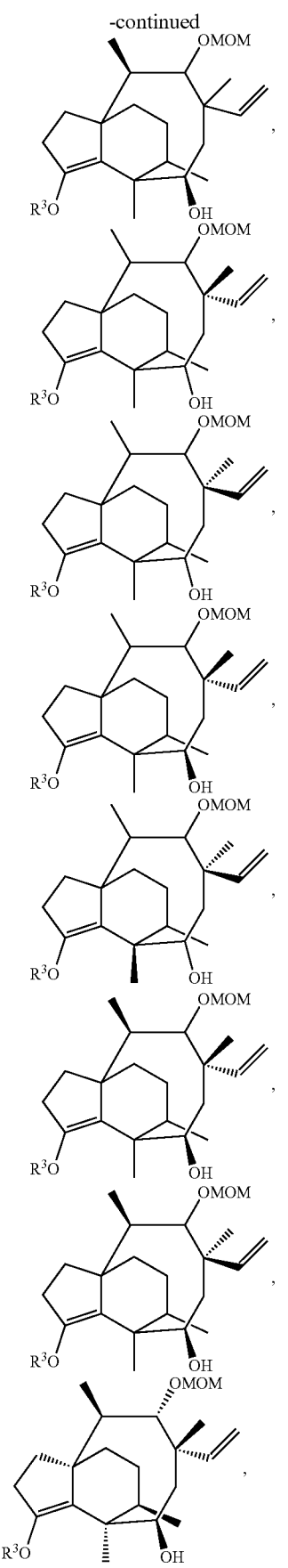, or -continued
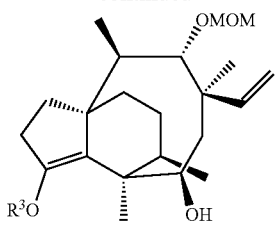
wherein R³ is defined herein.
In further embodiments, the compound of Formula VII is a compound of Formula VII-3:
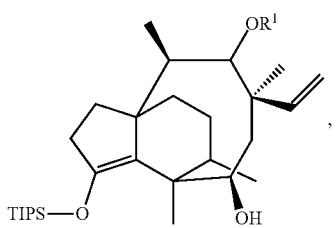
wherein R¹ is defined herein, preferably
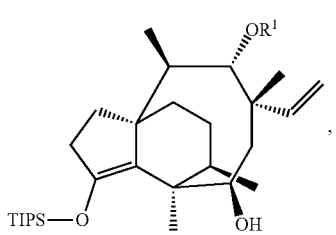,
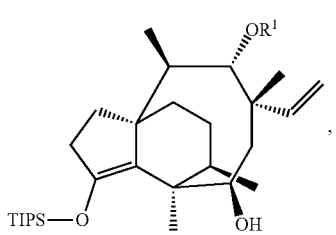,
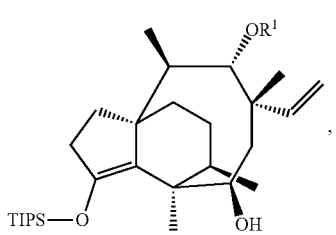,
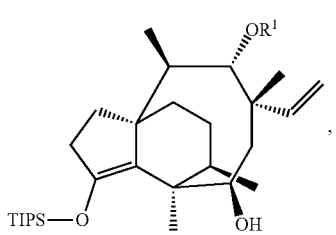,
-continued
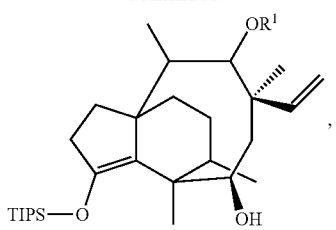,
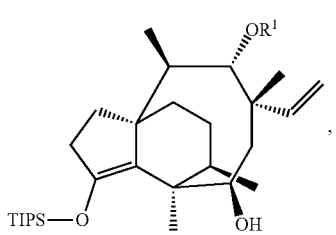,
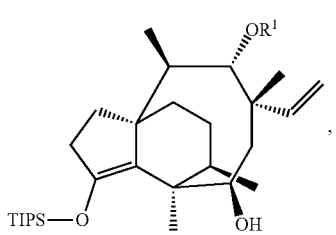,
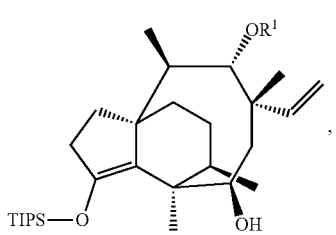,
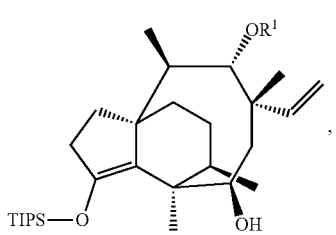.
In yet other embodiments, the compound of Formula VII is:
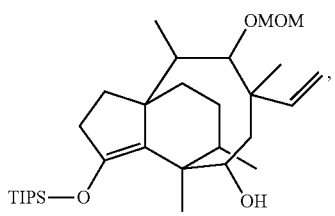,
preferably
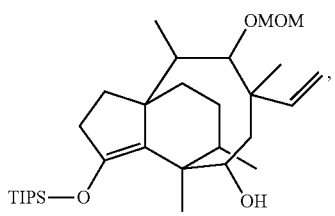, -continued

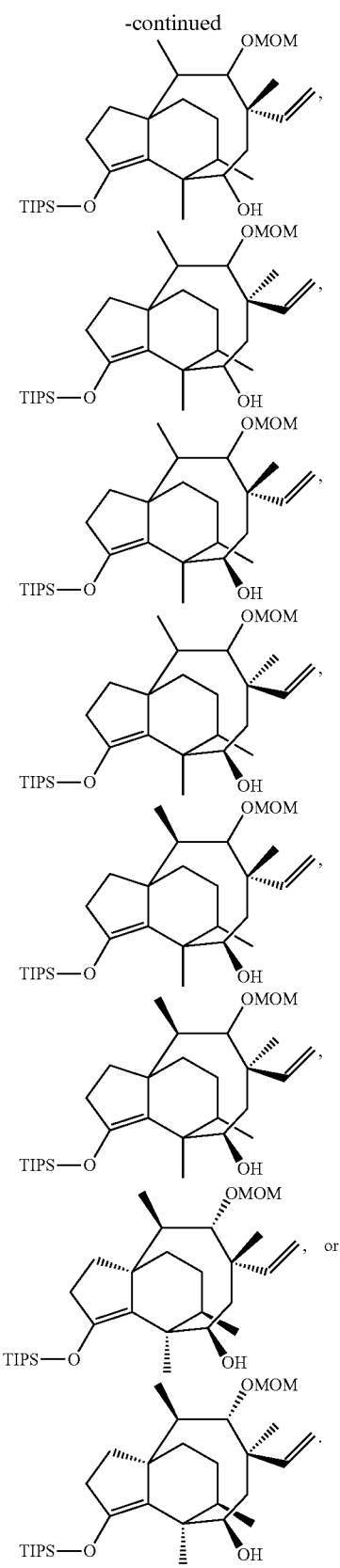

In an exemplary transformation, a compound of Formula VI is treated with excess lithium in ammonia in ethanol and diethylether at reduced temperature to form the compound of Formula VII.

Compounds of Formula VII are subjected to conditions sufficient to provide pleuromutilin. See, e.g., Procter, *Chem. Eur. J.* 2013, 19, 6718, which is incorporated by reference herein. In some embodiments, the pleuromutilin is (+)-pleuromutilin.

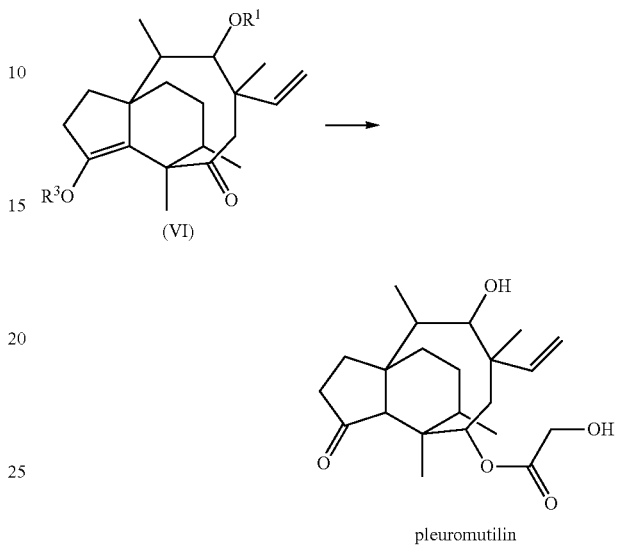

pleuromutilin

The conditions sufficient to provide the pleuromutilin first comprise acylating the compound of Formula VI. The acylation is preferably performed using, for example, 2-(2,2,2-trifluoroacetoxy)acetic acid in the presence of a coupling reagent, such as, for example 4-dimethylaminopyridine (DMP), 1-hydroxy-1H-benzotriazole, or 1-hydroxy-1H-azabenzotrilae, preferably DMAP, and a carbonyl activating agent such as, for example, dicyclohexylcarbodiimide or 1-ethyl-3-(3'dimethylaminopropyl)-carbodiimide (EDCI) or its hydrochloride derivative, preferably EDCI. Preferably, a molar excess of one or more of 2-(2,2,2-trifluoroacetoxy) acetic acid, the coupling reagent, and/or carbonyl activating agent are utilized. In some embodiments, at least about 1.5 equivalents, about 2 equivalents, about 3 equivalents, about 4 equivalents, about 5 equivalents, about 6 equivalents, about 7 equivalents, about 8 equivalents, about 9 equivalents, or about 10 equivalents, preferably at least about 6 equivalents, of 2-(2,2,2-trifluoroacetoxy)acetic acid are utilized. In further embodiments, at least about 1.5 equivalents, about 2 equivalents, about 3 equivalents, about 4 equivalents, about 5 equivalents, about 6 equivalents, about 7 equivalents, about 8 equivalents, about 9 equivalents, or about 10 equivalents, preferably at least about 6 equivalents, of the coupling reagent are utilized. In other embodiments, at least about 1.5 equivalents, about 2 equivalents, about 3 equivalents, about 4 equivalents, about 5 equivalents, about 6 equivalents, about 7 equivalents, about 8 equivalents, about 9 equivalents, or about 10 equivalents, preferably at least about 6 equivalents, of the carbonyl activating agent are utilized. The reaction is performed in a polar organic solvent, such as methylene chloride. Desirably, the transformation is performed under anhydrous and inert atmosphere conditions, such as nitrogen or argon.

Thereafter, the acylated product is subject to a methanolysis using methanol in the presence of a base. For example a trialkyl amine base such as diisopropylethylamine, triisopropylamine, trimethylamine, or trimethylamine, or mixtures thereof may be utilized. Preferably, the base comprises or is triethylamine. Preferably, the base is utilized in a molar excess. In certain embodiments, at least about 2, at least about 5, at least about 10, at least about 20, at least about 30 equivalents, preferably about 20 equivalents, of the base are utilized. Similarly, it is preferred that the methanol is present in a molar excess. In certain embodiments, at least about 2, at least about 5, at least about 10, at least about 20, at least about 30 equivalents, preferably about 20 equivalents, of methanol are utilized.

Pleuromutilin is prepared by subjecting the methanol intermediate to an acidic hydrolysis. Suitable acids include, without limitation, hydrochloric acid or sulfuric acid, preferably hydrochloric acid. Suitable solvents for the preparation of compounds of Formula V include ethereal solvents, in particular, cyclic ethers such as tetrahydrofuran. The transformation can take place at any suitable temperature, for example, ambient temperature or above. Suitable temperatures may include, for example, at least about 30, about 40, about 50, about 60, or about 70° C., preferably at least about 50° C.

In an exemplary transformation, a compound of Formula VII is acylated with 2-(2,2,2-trifluoroacetoxy)acetic acid followed by trifluoroacetate methanolysis then acidic hydrolysis effected global deprotection to deliver pleuromutilin. In another exemplary transformation, a compound of Formula VII is treated with EDCI.HCl, DMAP, and 2-(2,2,2-trifluoroacetoxy)acetic acid, followed by methanol in trimethylamine, and ending with hydrolysis using hydrochloride acid in tetrahydrofuran at elevated temperature to provide pleuromutilin, such as, for example:

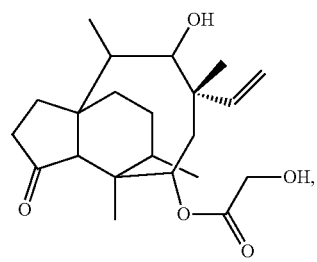

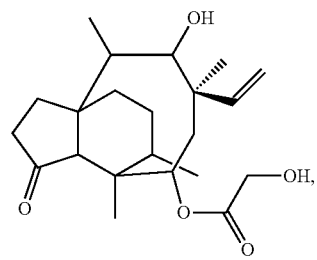

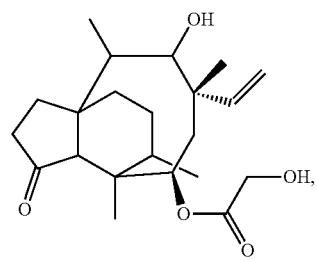

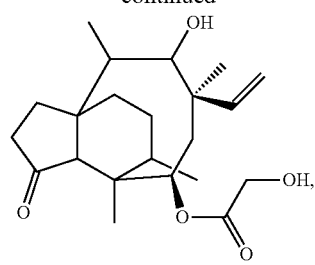

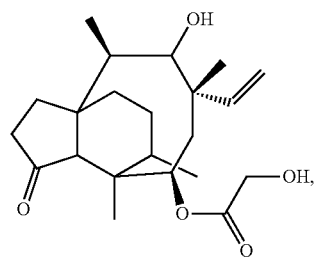

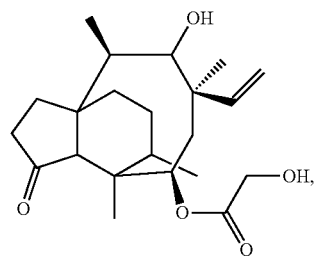

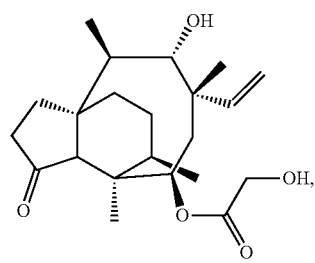

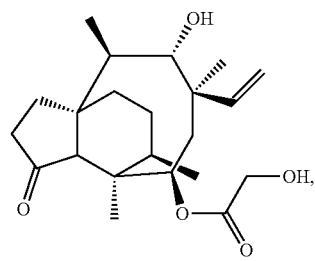

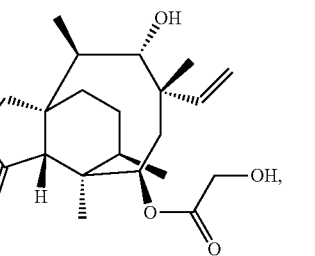 or

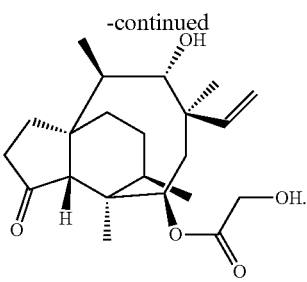

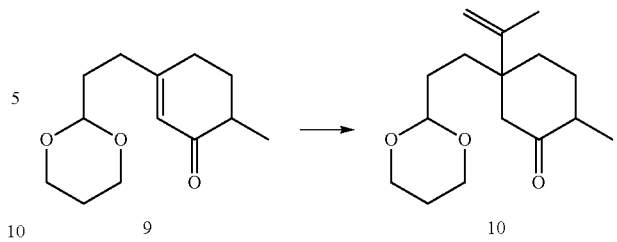

The preparation of pleuromutilin may be initiated with the preparation of enone 7 in one step from commercially available (+)-trans-dihydrocarvone as described in White, Org. Synth. 2005, 82, 108 (Coll. Vol. 11, 2009, 100).

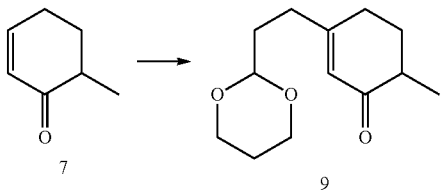

Compound 7 may then be reacted with the cuprate derived from

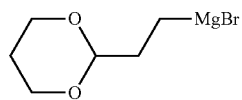

and CuCN.2LiCl in the presence of a silyl reagent, preferably TMSCl, to provide a silyl enol ether intermediate. The transformation can take place at any suitable temperature, for example, ambient temperature or below. Suitable temperatures may include, for example, about 20, 15, 10, 5, 0, −5, −10, −15, −20, −25, −30, −40, −50, −60, −70 or about −80° C., preferably about −40 to about −50° C. The silyl enol ether then undergoes a Pd-catalyzed desaturation for a time and at a temperature sufficient, followed by oxygen sparging, to provide compound 9. The palladium catalyst that may be used to effect the transformation includes Pd(OAc)$_2$. A catalytic amount of the palladium catalyst, such as at least about a 5 mol %, 10 mol %, 20 mol %, 30 mol %, 40 mol %, 50 mol %, 60 mol %, preferably about 10 mol %, is used. A highly polar, non-acidic, organic solvent such as DMSO, DMF, DMA, or benzonitrile, preferably DMSO, may be used.

Compound 9 is then subjected to a conjugate addition reaction under conditions for a time and at a temperature sufficient to provide isopropenyl cyclohexanone 10. In some embodiments, compound 9 is reacted with isopropenylmagnesium halide, preferably a bromide, or an allylic chloride in the presence of a copper reagent, preferably a copper halide such as CuI. Suitable temperatures may include, for example, about 20, 15, 10, 5, 0, −5, −10, −15, −20, −25, −30, −40, −50, −60, −70 or about −80° C., preferably about −70 to about −80° C. Desirably, the transformation is performed under anhydrous and inert conditions, such as nitrogen or argon, preferably argon.

Compound 10 is then converted to the allylic chloride 11 via an allylic chloride intermediate using trichloroisocyanuric acid (TCCA) for a sufficient time and at a sufficient temperature. See, e.g., Singh, Org. Process Res. Dev. 2017, 21, 551. Desirably, the transformation is performed under anhydrous and inert conditions, such as nitrogen or argon, preferably argon. In some embodiments, the reaction is performed in the presence of molecular sieves, e.g., 3 or 4 Å. Suitable temperatures may include, for example, about 20, 15, 10, 5, 0, −5, −10, −15, −20, preferably about 55 to about 5° C. An organic solvent such as cyclohexanone, benzonitrile, ethyl acetate, acetone, or mixtures thereof, preferably an ethyl acetate/cyclohexanone mixture, may be used.

The allylic chloride intermediate is then reacted with an aqueous acid solution for a sufficient time and at a sufficient temperature to provide enone compound 11. Suitable solvents for the preparation of compound 11 include ethereal solvents, in particular, cyclic ethers such as tetrahydrofuran. The transformation can take place at any suitable temperature, for example, ambient temperature or above. Suitable temperatures may include, for example, at least about 30, about 40, about 50, about 60, about 70° C., about 80° C., or about 90° C., preferably at least about 50° C. The aqueous acid solution may include a strong acid such as hydrochloric acid or sulfuric acid solution, preferably hydrochloric acid.

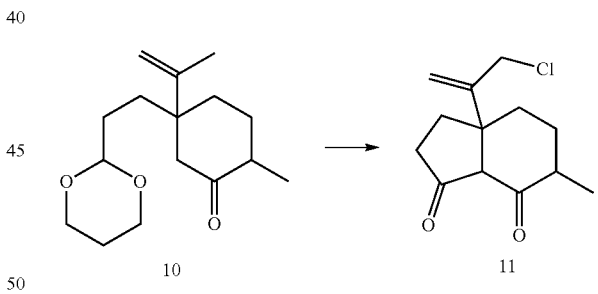

Compound 11 is then converted to compound 12 via an allylic alcohol intermediate. Compound 11 is treated with methyl magnesium chloride in the presence of a Cerium catalyst at a temperature sufficient to effect the translation. See, e.g., Krasovskiy, Angew. Chem. Int. Ed. 2006, 45, 497. Preferably, the catalyst is CeCl$_3$.2 LiCl. Desirably, an excess of the methyl magnesium chloride is utilized. In certain embodiments, at least about 1.2, about 1.3, about 1.4, about 1.5, about 1.6, about 1.7, about 1.8, about 1.9, about 2, about 2.5, or about 3 equivalents, preferably about 2 equivalents, of the Grignard reagent are utilized. Suitable temperatures may include, for example, about 20, 15, 10, 5, 0, −5, −10, −15, −20, −25, −30, −40, −50, −60, −70 or about −80° C., preferably about −70 to about −80° C. Desirably, the transformation is performed under anhydrous and inert conditions, such as nitrogen or argon, preferably argon.

The allylic alcohol intermediate is then converted to the hydrinenone compound 12 under conditions and for a time sufficient to effect an oxidative transposition. See, e.g., Dauben, *J. Org. Chem.* 1977, 42, 682. Desirably, the allylic alcohol intermediate is reagent with a mild oxidizing agent such as dimethyl sulfoxide, hypervalent iodine compounds such as Dess-Martin periodinane (DMP), or pyridinium chlorochromate (PCC), preferably PCC. An excess of the mild oxidizing agent may be utilized. In certain embodiments, at least about 1.5, about 2, about 2.5, about 3, about 3.5, about 4, about 4.5, or about 5 equivalents, preferably about 3 equivalents, of the mild oxidizing agent are utilized. Suitable temperatures may include room temperatures.

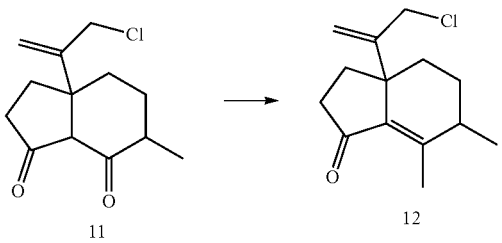 [SMILES: C=C(CCl)C12CCC(=O)C1C(=O)C(C)CC2 ; C=C(CCl)C12CCC(=O)C1=C(C)C(C)CC2]

Compound 12 is then converted to compound 5. See, e.g., Poulsen, Microbiol., 2001, 41, 1090-1099. The conversion was effected using a Kornblum oxidation technique via a 1-step conversion of the allyl halide to a conjugated aldehyde, the general techniques of which are known to those skilled in the art. Preferably, the conversion is performed using monopotassium phosphate and an alkali halide such as sodium iodide. An excess of monopotassium phosphate may be utilized. In certain embodiments, at least about 1.5, about 2, about 2.5, about 3, about 3.5, about 4, about 4.5, or about 5 equivalents, preferably about 2.5 equivalents, of monopotassium phosphate are utilized. A highly polar organic solvent such as DMSO, DMF, DMA, or benzonitrile, preferably DMSO, may be used. Suitable temperatures are elevated and may include, for example, at least about 70° C., about 75° C., about 80° C., about 85° C., about 90° C., about 95° C., about 100° C., about 105° C., about 110° C., about 115° C., or about 120° C., preferably at least about 95° C.

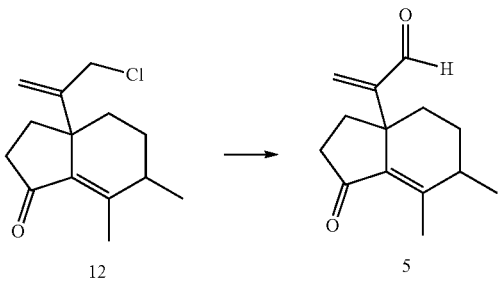 [SMILES: C=C(CCl)C12CCC(=O)C1=C(C)C(C)CC2 ; C=C(C=O)C12CCC(=O)C1=C(C)C(C)CC2]

The brevity and modularity of the processes described herein will enable the design and synthesis of new fully synthetic variants of mutilin antibiotics.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

EXAMPLES

Exemplary compounds useful in methods of the disclosure will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Unless otherwise stated, reactions were performed under an inert atmosphere (Ar) with freshly dried solvents utilizing standard Schlenk techniques. Glassware was oven-dried at 120° C. for a minimum of four hours, or flame-dried utilizing a Bunsen burner under high vacuum. Tetrahydrofuran (THF), methylene chloride ($CH_2Cl_2$), diethyl ether ($Et_2O$), benzene (PhH), and toluene (PhMe) were dried by passing through activated alumina columns. Absolute ethanol (200 Proof) was purchased from Koptec. Methanol (HPLC grade) was purchased from Fisher Scientific. Anhydrous ammonia ($NH_3$) was purchased from Matheson Tri-Gas. N,N-diisopropylethylamine ($iPr_2NEt$), triethylamine ($Et_3N$), methanol (MeOH), isopropanol (iPrOH), tert-butanol (tBuOH), and trimethylsilyl chloride (TMSCl) were distilled over calcium hydride prior to use. Unless otherwise stated, chemicals and reagents were used as received. All reactions were monitored by thin-layer chromatography using EMD/Merck silica gel 60 F254 pre-coated plates (0.25 mm) and were visualized by UV (254 nm), p-anisaldehyde, and/or $KMnO_4$ staining. Flash column chromatography was performed using silica gel (SiliaFlash® P60, particle size 40-63 microns [230 to 400 mesh]) purchased from Silicycle. $^1H$ and $^{13}C$ NMR spectra were recorded on a Bruker Avance III HD with Prodigy Cryoprobe (at 400 MHz and 101 MHz, respectively) or a Varian Inova 500 (at 500 MHz and 101 MHz respectively) and are reported relative to internal $CHCl_3$ (1H, δ=7.26) and $CDCl_3$ ($^{13}C$, δ=77.0). Data for $^1H$ NMR spectra are reported as follows: chemical shift (6 ppm) (multiplicity, coupling constant (Hz), integration). Multiplicity and qualifier abbreviations are as follows: s=singlet, d=doublet, t=triplet, q=quartet, m=multiplet, br=broad, app=apparent. IR spectra were recorded on a Perkin Elmer Paragon 1000 spectrometer and are reported in frequency of absorption ($cm^{-1}$). HRMS were acquired from the Caltech Mass Spectral Facility using fast-atom bombardment (FAB), electrospray ionization (ES+-TOF) or electron impact (EI). Optical rotations were measured on a Jasco P-2000 polarimeter using a 100 mm path-length cell at 589 nm.

Reagents were purchased from commercial vendors as follows: 2-(2-bromoethyl)-1,3-dioxane was purchased from TCI America. Palladium(II) acetate (Pd(OAc)$_2$, >99%), copper(I) iodide (CuI, 99.999%) and tetrakis(acetonitrile)palladium(II) tetrafluoroborate (Pd(CH$_3$CN)$_4$(BF$_4$)$_2$, >98%) were purchased from Strem Chemicals and stored in a nitrogen-filled glovebox. Tetrahydroxydiboron (B$_2$(OH)$_2$, 95%) and copper(I) cyanide (CuCN, 99.98%) were purchased from Sigma-Aldrich and stored in a nitrogen-filled glovebox. Samarium ingot (99.9% trace rare earth metals basis), tris(2,2,6,6-tetramethyl-3,5-heptanedionato)manganese(III) (Mn(dpm)$_3$, 97%), phenylsilane (PhSiH$_3$, 97%), lithium (wire stored in mineral oil, 99.9% trace metal basis), and tert-butyl hydroperoxide (TBHP, 5.5 M in decane over 4 Å MS) were purchased from Sigma-Aldrich.

Example 1: Synthesis of Hydrindanone Enal (5)

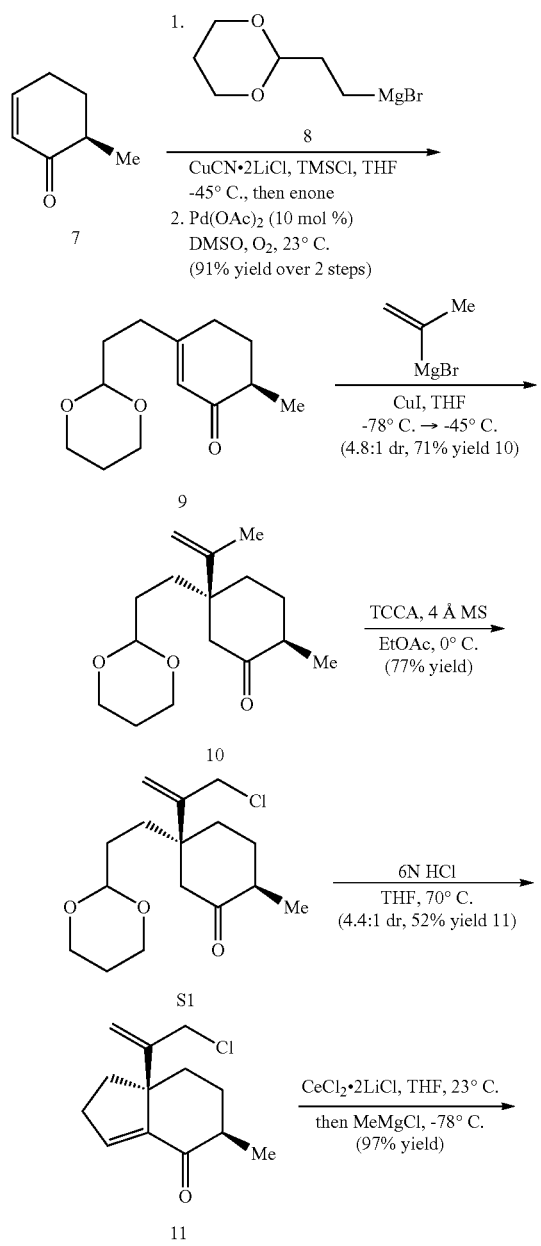

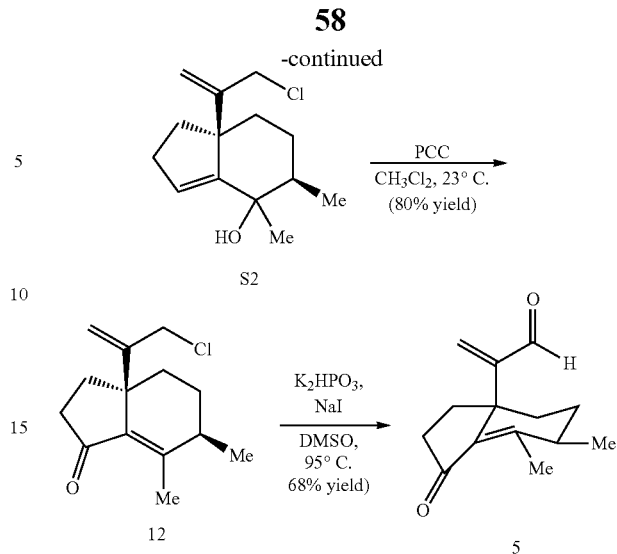

A. Preparation of Trisubstituted Enone (9):

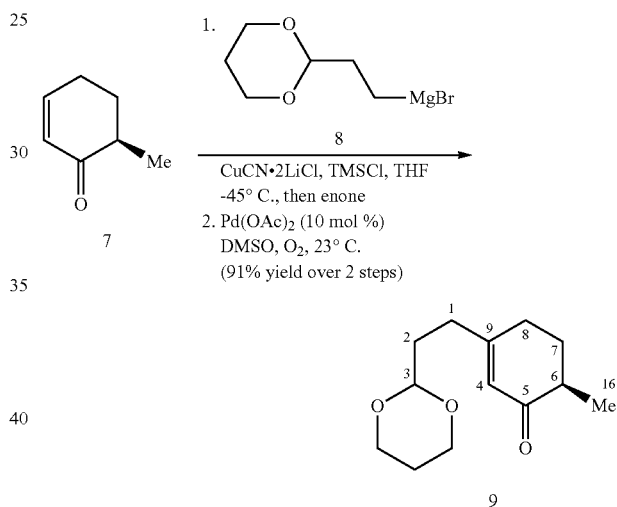

A flame-dried, 1 L, 3-necked round bottom flask equipped with a stir bar, reflux condenser, addition funnel, and glass stopper was charged with activated magnesium turnings (8.02 g, 330.0 mmol, 3 equiv). The atmosphere was exchanged three times with argon before addition of THF (40 mL). To the rapidly stirred suspension was added 1,2-dibromoethane (3.10 g, 16.5 mmol, 0.15 equiv) dropwise. An exothermic reaction was observed, and the suspension became grey. The reaction was cooled to ambient temperature, and subsequently, a solution of 2-(2-bromoethyl)-1,3-dioxane (42.9 g, 219.9 mmol, 2 equiv) in THF (170 mL, 0.64 M) was added dropwise via an addition funnel over 1 h. Upon completion of addition, the reaction was stirred for an additional 30 min. The resulting suspension was filtered via cannula into a flame-dried, 2 L, 2-necked round bottom flask equipped with a large stir bar under an atmosphere of argon, and the Grignard reagent 8 was diluted with THF (170 mL, 0.64 M). Titration against salicylaldehyde phenylhydrazone yielded the concentration of Grignard reagent 8 as 0.38 M.

The Grignard solution was cooled to −45° C. Subsequently, a freshly prepared solution of CuCN.2LiCl in THF was added via cannula over 20 min. CuCN.2LiCl was prepared by dissolving CuCN (9.85 g, 110.0 mmol, 1 equiv) and LiCl (9.32 g, 220.0 mmol, 2 equiv) in THF (110 mL, 1.0 M w.r.t. CuCN) and vigorously stirring at ambient temperature for 1 h. After an additional 20 min, freshly distilled TMSCl (14.3 g, 132.0 mmol, 1.2 equiv) was added. The reaction became heterogeneous, and stirring was difficult. After 10 min, a solution of (R)-enone 7 (12.1 g, 110.0 mmol, 1 equiv; White, *Org. Synth.* 2005, 82, 108-114) in THF (183 mL, 0.6 M) was added via cannula over 30 min. The reaction was stirred for 1 h and then quenched with sat. aq. NaHCO$_3$ (10 mL) at −45° C. After arming to ambient temperature, pentane (600 mL) was added, and the suspension was filtered through Celite. The volatiles were concentrated under reduced pressure, additional pentane (500 mL) was added and the slurry was filtered through Celite. This process was repeated an additional time to afford 38.2 g of a clear oil. $^1$H NMR (CDCl$_3$) shows desired silyl enol ether along with 2-(2-cyanoethyl)-1,3-dioxane. The silyl enol ether was used immediately without further purification.

To a 1 L round bottom flask equipped with a stir bar was added the silyl enol ether, anhydrous DMSO (550 mL, 0.2 M) and Pd(OAc)$_2$ (2.47 g, 11.0 mmol, 10 mol %). The mixture was sparged with O2 for 2 h then stirred at ambient temperature for 36 h. At this time, $^1$H NMR analysis showed the ratio of product to remaining silyl enol ether was 11:1. Water (700 mL) was added, and the product was extracted into Et$_2$O (4×400 mL). The combined organic layers were washed with brine (1×50 mL), dried over Na$_2$SO$_4$, and concentrated under reduced pressure to afford 38.1 g of a viscous, yellow oil.

Purification was achieved via flash column chromatography on SiO$_2$ [750 g SiO$_2$, 60 mL fractions, Et$_2$O/hexanes=40% (1.5 L), 45% (500 mL), 50% (500 mL), 55% (500 mL), 65% (500 mL), 80% (500 mL)] to afford trisubstituted enone 9 (20.3 g, 90.5 mmol, 91% yield over 2 steps) as a viscous, clear oil.

TLC (25% EtOAc/hexanes): R$_f$=0.23 (UV, p-anisaldehyde).

$^1$H NMR (400 MHz, CDCl$_3$): δ 5.84 (s, 1H, C$_4$), 4.53 (t, J=5.0 Hz, 1H, C3), 4.09 (ddt, J=10.7, 5.1, 1.3 Hz, 2H, OCH2CH2CH2O), 3.75 (m, 2H, OCH2CH2CH2O), 2.31 (m, 5H, C1, C2, C6, C8), 2.05 (m, 2H, OCH2CH2, C7), 1.78 (m, 2H, C1, C2), 1.68 (m, 1H, C7), (d sept, J=13.5, 1.4 Hz, 1H, OCH2CH2), 1.12 (d, J=6.9 Hz, 3H, C16).

$^{13}$C NMR (101 MHz, CDCl$_3$): δ 202.3 (C5=O), 164.5 (C9), 125.1 (C4), 101.2 (C3), 66.9 (OCH2CH2), 40.8 (C6), 32.3 (C1), 31.9 (C2), 30.8 (C7), 29.3 (C8), 25.7 (OCH2CH2), 15.1 (C16).

FTIR (AT-IR): 2857, 2249, 1662, 1375, 1211, 1146, 1079, 1046, 907, 647 cm$^{-1}$.

HRMS (FAB+, m/z): calc'd for C$_{13}$H$_{21}$O$_3$ [M+H]$^+$ 225.1491, found: 225.1502. [α]$_D^{23}$: +65° (c=1.055, CHCl$_3$).

B. Preparation of Isopropenyl Cyclohexanone (10):

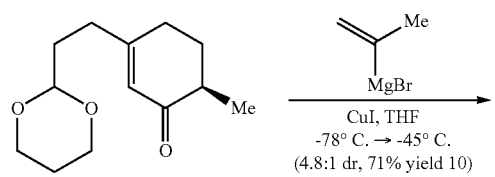

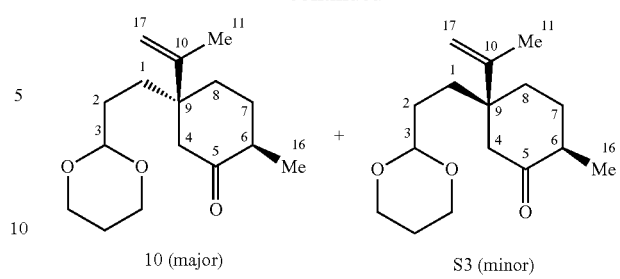

10 (major)  S3 (minor)

A flame-dried, 3 L, 2-necked round bottom flask equipped with a stir bar was evacuated and backfilled with argon three times. The flask was charged with CuI (17.6 g, 92.6 mmol, 1.5 equiv) and THF (617 mL). The suspension was cooled to −78° C. and stirred for 15 min. Isopropenylmagnesium bromide (0.5 M in THF (Aldrich), 371 mL, 185 mmol, 3 equiv) was added dropwise via cannula transfer and the solution was stirred for 5 min. The reaction was warmed to −25° C. and stirred for 10 min. Thereafter, the mixture was cooled back down to −78° C. and stirred for 15 min. Trisubstituted enone 9 (13.9 g, 61.8 mmol, 1 equiv) was dissolved in THF (617 mL) and added dropwise via cannula transfer. The solution was warmed to −50° C. and stirred for 25 min or until complete by TLC analysis. The reaction mixture was quenched with sat. aq. NH$_4$Cl (400 mL) at −50° C. and the biphasic solution was warmed to ambient temperature. The layers were separated and the aqueous phase was extracted with Et$_2$O (3×350 mL). The combined organic layers were washed with brine (100 mL), dried over MgSO$_4$ and concentrated under reduced pressure to afford 18.4 g of a viscous oil.

Purification was achieved via flash column chromatography on SiO$_2$ [1400 g SiO$_2$, 20% EtOAc/hexanes] to afford isopropenyl cyclohexenone 10 (11.64 g, 43.7 mmol, 71% yield) as a white solid.

Major Diastereomer (10)

TLC (20% EtOAc/hexanes): R$_f$=0.16 (p-anisaldehyde).

$^1$H NMR (400 MHz, CDCl$_3$): δ 4.93 (br s, 1H, C17), 4.69 (s, 1H, C17), 4.45 (t, J=4.7 Hz, 1H, C3), 4.07 (m, 2H, OCH2CH2), 3.72 (m, 2H, OCH2CH2), 2.73 (dd, J=14.2, 3.0 Hz, 1H, C4), 2.20 (app d of septets, J=6.7, 1.2 Hz, 1H, C6), 2.07 (dd, J=14.2, 1.0 Hz, 1H, C4), 2.04 (m, 1H, OCH2CH2), 1.96 (dq, J=13.8, 3.2 Hz, 1H, C8), 1.83 (m, 1H, C7), 1.65 (m, 1H, C2), 1.61 (dd, J=1.2, 0.5 Hz, 3H, C11), 1.59 (m, 1H, C8), 1.46 (m, 1H, C1), 1.41 (m, 1H, C1), 1.37 (m, 1H, C2), 1.36 (m, 1H, C7), 1.32 (m, 2H, OCH2CH2), 0.97 (d, J=6.5 Hz, 3H, C16).

$^{13}$C NMR (101 MHz, CDCl$_3$): δ 212.2 (C5=O), 145.7 (C10), 116.0 (C17), 102.3 (C3), 66.9 (OCH2CH2), 49.8 (C4), 47.7 (C9), 44.8 (C6), 34.8 (C8), 34.5 (C2), 30.4 (C7), 29.5 (C1), 25.7 (OCH2CH2), 18.9 (C11), 14.5 (C16).

FTIR (AT-IR): 2960, 2929, 2853, 1706, 1454, 1239, 1144, 994, 880 cm$^{-1}$.

HRMS (FAB+, m/z): calc'd for C$_{16}$H$_{27}$O$_3$ [M+H]$^+$ 267.1960, found: 267.1966.

[α]$_D^{23}$: +42° (c=1.16, CHCl$_3$).

Minor Diastereomer (S3)

TLC (20% EtOAc/hexanes): R$_f$=0.27 (p-anisaldehyde).

$^1$H NMR (400 MHz, CDCl$_3$): δ 4.86 (pent, J=1.2 Hz, 1H, C17), 4.70 (m, 1H, C17), 4.42 (m, 1H, C3), 4.06 (ddt, J=10.5, 5.0, 1.2 Hz, 2H, OCH2CH2), 3.72 (m, 2H, OCH2CH2), 2.40 (dd, J=13.3, 2.0 Hz, 1H, C4), 2.35 (m, 1H, C6), 2.32 (m, 1H, C4), 2.07 (tt, J=13.3, 5.2 Hz, 1H, OCH2CH2), 1.98 (m, 1H, C7), 1.88 (m, 1H, C1), 1.76 (td, J=11.5, 4.1 Hz, 1H, C1), 1.68 (dd, J=1.3, 0.8 Hz, 3H, C11), 1.50 (m, 1H, C7), 1.40 (m, 1H, C2), 1.39 (m, 1H, C2), 1.37 (m, 1H, C8), 1.35 (m, 1H, C8), 1.30 (m, 1H, OCH2CH2), 1.05 (d, J=6.7 Hz, 3H, C16).

$^{13}$C NMR (101 MHz, CDCl$_3$): δ 213.3 (C5=O), 148.8 (C10), 111.9 (C17), 102.3 (C3), 66.9 (OCH2CH2), 66.8 (OCH2CH2), 50.0 (C4), 46.7 (C9), 44.3 (C6), 31.9 (C1), 30.2 (C7), 29.5 (C8), 28.2 (C2), 25.7 (OCH2CH2), 19.0 (C11), 14.9 (C16).

FTIR (AT-IR): 2961, 2930, 2850, 1708, 1635, 1452, 1377, 1143, 994, 880 cm$^{-1}$.

HRMS (FAB+, m/z): calc'd for C$_{16}$H$_{27}$O$_3$ [M+H]$^+$ 267.1960, found: 267.1949.

$[α]_D^{23}$: +1.9° (c=0.91, CHCl$_3$).

C. Preparation of Allylic Chloride (S1):

Hz, 1H, C2), 2.04 (tdd, J=17.5, 8.7, 4.2 Hz, 2H, C1), 1.89 (ddt, J=13.3, 6.6, 3.5 Hz, 1H, C7), 1.80-1.65 (m, 2H, C8), 1.55-1.28 (m, 4H, C1, C7, C2, OCH-2CH2CH2O), 0.99 (d, 3H, C16).

$^{13}$C NMR (101 MHz, CDCl$_3$): δ 211.7 (C5=O), 145.0 (C10), 121.0 (C17), 101.9 (C3), 66.9 (OCH2CH2CH2O), 50.2 (C4), 48.1 (C9), 44.9 (C6), 44.0 (C11), 35.0 (C8), 35.0 (C1), 30.6 (C7), 29.5 (C2), 25.7 (OCH2CH2CH2O), 14.4 (C16).

FTIR (AT-IR): 2929, 2359, 1707, 1377, 1214, 1143, 1079, 880, 730, 668 cm$^{-1}$.

HRMS (FAB+, m/z): calc'd for C$_{16}$H$_{26}$O$_3$Cl [M+H]$^+$ 301.1571, found: 301.1564.

$[α]_D^{23}$: +49° (c=0.495, CHCl$_3$).

D. Preparation of Enone (11):

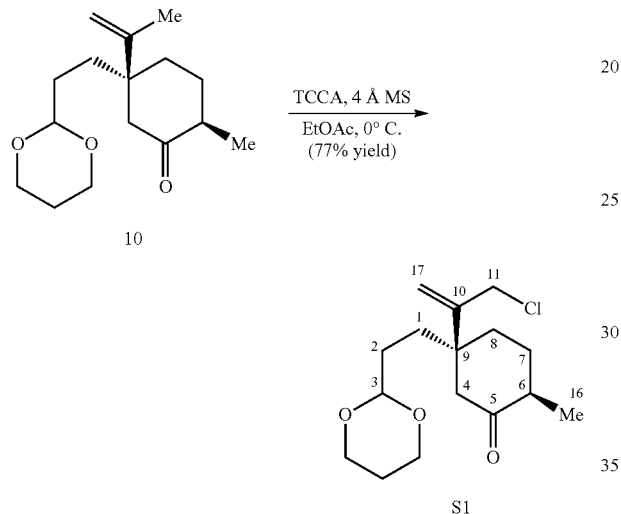

This procedure was adapted from the work of Kumar (*Org. Process. Dev.* 2017, 21, 551-558). A flame-dried, 2 L, 2-neck round bottom flask equipped with a stir bar was charged with activated 4 Å mol sieves and cyclohexanone 10 (12.06 g, 45.28 mmol, 1 equiv). The atmosphere was exchanged three times with argon before adding EtOAc (916 mL, 0.05 M) that had been degassed with argon. The resulting colorless solution was cooled to 0° C. and stirred for an additional 10 min. Subsequently, finely ground trichloroisocyanuric acid (TCCA) (10.52 g, 45.28 mmol, 1 equiv) was added in one portion. The reaction was stirred (900 rpm) for 10 min or until complete by TLC analysis. The reaction mixture was quenched at 0° C. with sat. aq. Na$_2$S$_2$O$_3$ (150 mL). The biphasic solution was warmed to ambient temperature and filtered. The aqueous layer was extracted with EtOAc (4×100 mL). The combined organic layers were washed with H$_2$O (100 mL), dried over MgSO$_4$, filtered, and concentrated under reduced pressure to afford a yellow oil.

Purification was achieved via flash column chromatography on SiO$_2$ [1400 g SiO$_2$, 15% EtOAc/hexanes→30%] to afford allylic chloride Si (10.52 g, 39.5 mmol, 77% yield) as a white solid.

TLC (50% EtOAc/hexanes): R$_f$=0.5 (p-anisaldehyde).

$^1$H NMR (400 MHz, CDCl$_3$): δ 5.54 (s, 1H, C17), 5.15 (s, 1H, C17), 4.46 (t, J=4.8 Hz, 1H, C3), 4.12-4.03 (m, 2H, OCH2CH2CH2O), 4.01 (d, J=1.0 Hz, 2H, C11), 3.73 (td, J=12.2, 2.4 Hz, 2H, OCH2CH2CH2O), 2.76 (dd, J=14.2, 3.0 Hz, 1H, C4), 2.34-2.20 (m, 1H, C6), 2.14 (dd, J=14.2, 1.1

A 250 mL round bottom flask equipped with a stir bar and reflux condenser was charged with allylic chloride 51 (10.8 g, 35.9 mmol, 1 equiv) and THF (125 mL). The homogeneous solution was vigorously stirred (960 rpm) and 6 N HCl (17.96 mL, 108 mmol, 3 equiv) was added dropwise. The reaction was heated to 70° C. and stirred for 4 h. The reaction was quenched with sat. aq. NaHCO$_3$ (45 mL). The layers were separated and the aqueous layer was extracted with Et$_2$O (3×75 mL). The combined organic layers were washed with brine (25 mL) and dried over MgSO$_4$. The suspension was filtered, and concentrated under reduced pressure to afford 10.4 g of a viscous yellow oil.

Purification was achieved via flash column chromatography on SiO$_2$ [1400 g SiO$_2$, 5% Et$_2$O/hexanes→10%] to afford enone 11 (4.15 g, 18.5 mmol, 52% yield) as a colorless solid.

Major Diastereomer (11)

TLC (50% Et$_2$O/hexanes): R$_f$=0.75 (UV, p-anisaldehyde).

$^1$H NMR (400 MHz, CDCl$_3$): δ 6.55 (t, J=2.7 Hz, 1H, C3), 5.39 (s, 1H, C17), 4.96 (s, 1H, C17), 4.16-4.05 (m, 2H, C11), 2.39-2.32 (m, 3H, C1, C2), 2.29-2.18 (m, 2H, C6, C8), 1.95-1.84 (m, 2H, C7, C8), 1.73-1.45 (m, 2H, C1, C7), 1.09 (d, J=6.7 Hz, 2H, C6).

$^{13}$C NMR (101 MHz, CDCl$_3$): δ 202.1 (C5=O), 146.8 (C4), 146.4 (C10), 137.6 (C3), 119.0 (C17), 57.9 (C9), 45.2 (C6), 44.7 (C11), 39.4 (C8), 35.3 (C1), 30.5 (C7), 30.1 (C2), 14.9 (C16).

FTIR (AT-IR): 2929, 2860, 1682, 1622, 1454, 1312, 1232, 1012, 927, 757, cm$^{-1}$.

HRMS (FAB+, m/z): calc'd for $C_{13}H_{18}ClO$ [M+H]$^+$ 225.1046, found: 225.1061.

$[\alpha]_D^{23}$: +58.4° (c=0.715, CHCl$_3$).

Minor Diastereomer (S3)

TLC (50% Et$_2$O/hexanes): $R_f$=0.75 (UV, p-anisaldehyde)

$^1$H NMR (400 MHz, CDCl$_3$): δ 6.70 (t, J=2.7 Hz, 1H, C3), 5.3 (s, 1H, C17), 5.00 (s, 1H, C17), 4.21-4.01 (m, 2H, C11), 2.55-2.44 (m, 1H, C6), 2.42-2.32 (m, 2H, C2), 2.28 (ddt, J=12.6, 5.4, 2.7 Hz, 1H, C1), 2.16 (dt, J=13.8, 4.0 Hz, 1H, C8), 2.04-1.83 (m, 2H, C7), 1.74 (td, J=13.4, 3.9 Hz, 1H, C8), 1.54 (dq, J=13.9, 3.9 Hz, 1H, C7), 1.12 (d, J=7.4 Hz, 3H, C16).

$^{13}$C NMR (101 MHz, CDCl$_3$): δ 203.4 (C5=O), 146.7 (C4), 145.3 (C10), 140.1 (C3), 118.2 (C17), 56.7 (C9), 44.8 (C11), 41.9 (C6), 39.8 (C12), 30.7 (C8), 30.0 (C2), 28.0 (C7), 17.8 (C16).

FTIR (AT-IR): 2925, 2855, 1687, 1620, 1456, 1376, 1262, 1175, 1098, 924 cm$^{-1}$.

HRMS (EI+, m/z): calc'd for $C_{13}H_{17}ClO$ [M]$^+$ 224.0968, found: 224.0940.

$[\alpha]_D^{23}$: 46.8° (c=0.115, CHCl$_3$).

E. Preparation of Allylic Alcohol (S2):

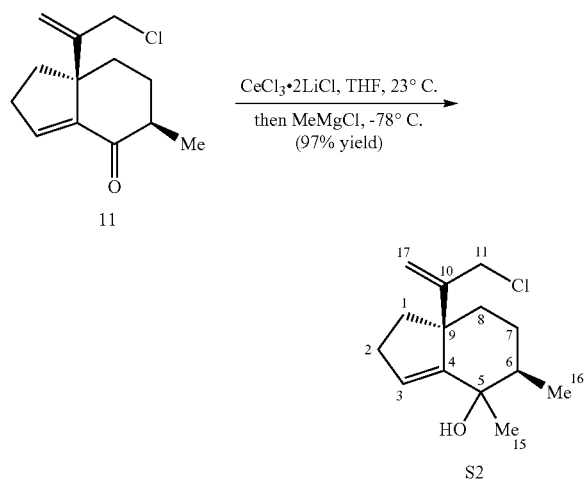

A flame-dried, 50 mL round bottom flask equipped with a stir bar was charged with enone 11 (1.101 g, 4.9 mmol, 1 equiv). The atmosphere was exchanged with argon three times before adding a solution of CeCl$_3$·2LiCl$_3$ (0.3 M in THF, 16.3 mL, 1 equiv; Krasovskiy, *Angew. Chem. Int. Ed.* 2006, 45, 497-500). Upon addition of CeCl$_3$·2LiCl, a bright yellow solution was obtained and stirred for 1 h at ambient temperature. The reaction mixture was then cooled to −78° C. and stirred for 15 min. The solution then became pale yellow slurry and stirring became difficult. A solution of methylmagnesium chloride (3.0 M in THF (Aldrich), 3.3 mL, 9.8 mmol, 2 equiv) was added dropwise over 30 min. The slurry was perturbed by hand until magnetic stirring resumed. The reaction was stirred at −78° C. until TLC analysis indicated complete consumption of starting material (about 15 min).

The gray solution was quenched at −78° C. via slow addition of 1 M HCl (15 mL) using a vent needle to relieve excess pressure. Thereafter, the solution was warmed to ambient temperature while the slurry slowly quenched. The mixture was then transferred to a separatory funnel and diluted with H$_2$O (20 mL) and Et$_2$O (50 mL). The layers separated, and the aqueous layer was extracted with Et$_2$O (3×20 mL). The combined organic layers was washed with brine (40 mL) and dried over MgSO$_4$. The suspension was filtered and concentrated under reduced pressure to afford a yellow oil.

Purification was achieved via flash column chromatography on SiO$_2$ [100 g SiO$_2$, 45 mL fractions, 200 mL forerun, Et$_2$O/hexanes=15% (1.2 L), 30% (250 mL), 40% (1 L)] to afford the less polar diastereomer (fractions 3-10) followed by the more polar diastereomer (fractions 17-33). The volatiles were concentrated under reduced pressure to afford an inconsequential mixture of diastereomers S2 (1.15 g, 4.78 mmol, 97% combined yield). An analytically pure sample of the less polar diastereomer was obtained and a representative spectrum of the mixture as used in the next step is also provided.

TLC (20% Et$_2$O/hexanes): $R_f$=0.46 and 0.09 (p-anisaldehyde).

$^1$H NMR (400 MHz, CDCl$_3$): δ 5.79 (t, J=2.4 Hz, 1H, C3), 5.44-5.41 (m, 1H, C17), 5.27 (s, 1H, C17), 4.24 (dd, J=13.1, 0.6 Hz, 1H, C11), 4.08 (dd, J=13.1, 1.0 Hz, 1H, C11), 2.46-2.33 (m, 3H, C2, C8), 2.05 (ddd, J=13.4, 7.9, 3.4 Hz, 1H, C1), 1.76 (dt, J=13.3, 9.0 Hz, 1H, C1), 1.57 (s, 1H, OH), 1.46-1.38 (m, 3H, C6, C7, C8), 1.37 (s, 3H, C15), 0.92 (d, J=6.4 Hz, 3H, C16).

$^{13}$C NMR (101 MHz, CDCl$_3$): δ 150.1 (C4), 149.7 (C10), 126.5 (C3), 113.8 (C17), 72.1 (C5), 54.5 (C9), 45.7 (C11), 43.1 (C6), 41.4 (C1), 38.2 (C8), 30.3 (C2), 28.3 (C7), 24.4 (C15), 14.8 (C16).

FTIR (AT-IR): 3315, 2872, 2360, 1596, 1489, 1275, 1031, 1001, 899, 697 cm$^{-1}$.

HRMS (FAB+, m/z): calc'd for $C_{14}H_{20}ClO$ [M+H]$^+$−H$_2$ 239.1203, found: 239.1176.

$[\alpha]_D^{23}$: +27.0° (c=0.210, CHCl$_3$).

F. Preparation of Hydrindenone (12):

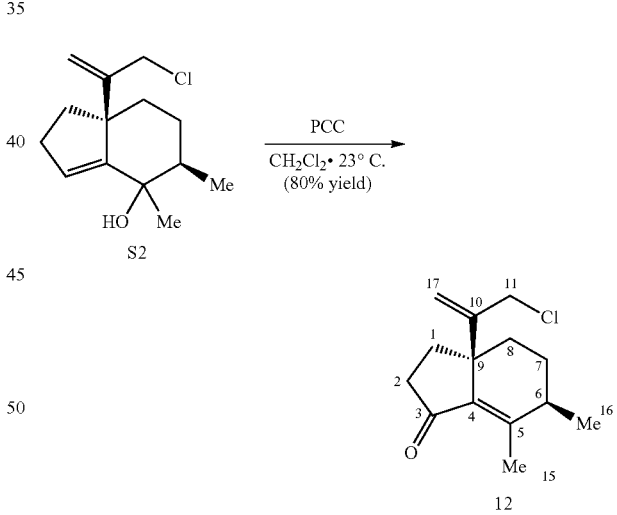

This procedure was adapted from the work of Dauben (*J. Org. Chem.* 1977, 42, 682-685). To a 100 mL round bottom flask equipped with a stir bar was added allylic alcohol S2 (1.15 g, 4.78 mmol, 1 equiv) and CH$_2$Cl$_2$ (32 mL). Pyridinium chlorochromate (3.09 g, 14.24 mmol. 3 equiv) was added in one portion and the reaction was stirred at ambient temperature for 12 h or until complete by aliquot NMR.

Upon complete consumption of starting material, the reaction mixture was transferred to a 500 mL separatory funnel. In the reaction flask remained a black resin, which was diluted with 20 mL Et$_2$O and 60 mL of 5% NaOH. The biphasic mixture was stirred until all the black resin had gone into solution, where it was then transferred into the separatory funnel. The organic layer was separated, and the aqueous layer was extracted with Et$_2$O (3×20 mL). The combined organic layers were then washed with 1 M HCl (2×15 mL) which gave a pale yellow organic layer. The phases were again separated, and washed with sat. aq. NaHCO$_3$. The combined organic layers were dried over MgSO$_4$, filtered, and concentrated under reduced pressure.

Purification was achieved via flash column chromatography with SiO$_2$ [50 g SiO$_2$, 10% Et$_2$O/hexanes] to afford enone 12 (902 mg, 3.78 mmol, 80% yield) as viscous, clear oil.

TLC (20% Et$_2$O/hexanes): R$_f$=0.24 (UV, p-anisaldehyde).

$^1$H NMR (400 MHz, CDCl$_3$): δ 5.49 (s, 1H, C17), 4.93 (d, J=0.8 Hz, 1H, C17), 4.10 (d, J=0.9 Hz, 2H, C11), 2.34-2.04 (m, 5H, C1, C2, C6, C8, C15), 1.75-1.66 (m, 1H, C7), 1.63-1.54 (m, 1H, C1), 1.39-1.15 (m, 2H, C7, C8), 1.06 (d, J=7.1 Hz, 3H, C16).

$^{13}$C NMR (101 MHz, CDCl$_3$): δ 207.4 (C3=O), 152.3 (C4), 147.4 (C5), 135.6 (C10), 121.8 (C17), 50.6 (C9), 43.9 (C11), 37.7 (C6), 35.6 (C2), 33.2 (C8), 32.5 (C1), 28.2 (C7), 19.1 (C16), 16.9 (C15).

FTIR (AT-IR): 2932, 1707, 1630, 1444, 1267, 1211, 1077, 926, 801, 754, 622 cm$^{-1}$.

HRMS (TOF, ES+): calc'd for C$_{14}$H$_{19}$ClONa [M+Na]$^+$ 261.1022, found 261.1006.

[α]$_D^{23}$: −252.8° (c=0.66, CHCl$_3$).

G. Preparation of Enal (5):

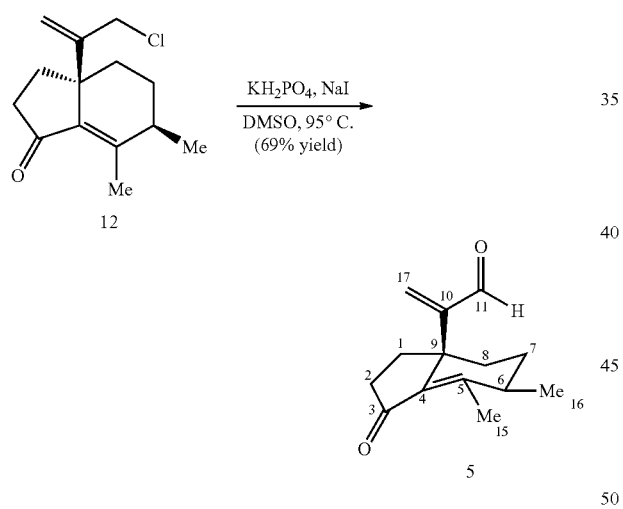

This procedure was adapted from the work of Kumar and coworkers. 2 A 20 mL scintillation vial equipped with a stir bar was charged with hydrindenone 12 (250 mg, 1.047 mmol, 1 equiv), K$_2$HPO$_4$·3H$_2$O (595 mg, 2.62 mmol, 2.5 equiv), NaI (65 mg, 0.419 mmol, 0.4 equiv) and DMSO (10 mL). The vial was sealed with a teflon cap and the heterogeneous mixture was heated to 95° C. with vigorous stirring (1000 rpm). After 7.5 h, aliquot NMR analysis indicated complete consumption of starting material. The heterogeneous mixture was allowed to cool to ambient temperature and sat. aq. NaHCO$_3$ (5 mL) was added. The layers were separated and the aqueous layer was extracted with Et$_2$O (4×15 mL). The combined organic layers were washed with H$_2$O (10 mL), and dried over MgSO$_4$. The suspension was filtered and concentrated under reduced pressure to afford a yellow oil.

Purification was achieved via flash column chromatography on SiO$_2$ [75 g SiO$_2$, Et$_2$O/hexanes=20%] to afford enal 5 (157 mg, 0.719 mmol, 69% yield) as a white solid.

TLC (30% Et$_2$O/hexanes): R$_f$=0.30 (UV, p-anisaldehyde).

$^1$H NMR (400 MHz, CDCl$_3$): δ 9.57 (s, 3H, C11), 6.17 (s, 1H, C17), 6.06 (s, 1H, C17), 2.58 (ddd, J=12.9, 7.9, 1.2 Hz, 1H, C2), 2.48 (dt, J=13.1, 3.4 Hz, 1H, C8), 2.17 (m, 1H, C6), 2.16 (s, 3H, C15), 2.12 (ddd, J=18.5, 8.6, 1.1 Hz, 1H, C1), 2.06 (ddd, J=18.5, 12.6, 7.9 Hz, 1H, C1), 1.70 (m, 1H, C7), 1.64 (dd, J=12.6, 8.7, Hz, 1H, C2), 1.34 (td, J=14.0, 2.7 Hz, 1H, C8), 1.04 (s, 3H, C16), 0.97 (m, 1H, C7).

$^{13}$C NMR (101 MHz, CDCl$_3$): δ 207.9 (C3=O), 193.8 (C11=O), 153.5 (C5), 152.8 (C10), 140.5 (C17), 135.1 (C4), 48.1 (C9), 37.5 (C6), 35.9 (C1), 32.3 (C8), 31.8 (C2), 28.5 (C7), 19.3 (C16) 17.0 (C15).

FTIR (AT-IR): 2950, 2931, 1705, 1629, 1080, 907, 878, 764, 702, 647 cm$^{-1}$.

HRMS (FAB+, m/z): calc'd for C$_{14}$H$_{19}$O$_2$ [M+H]$^+$ 219.1385, found 219.1387.

[α]$_D^{23}$: −215° (c=1.01, CHCl$_3$).

Example 2: Synthesis of (+)-Pleuromutilin (1)

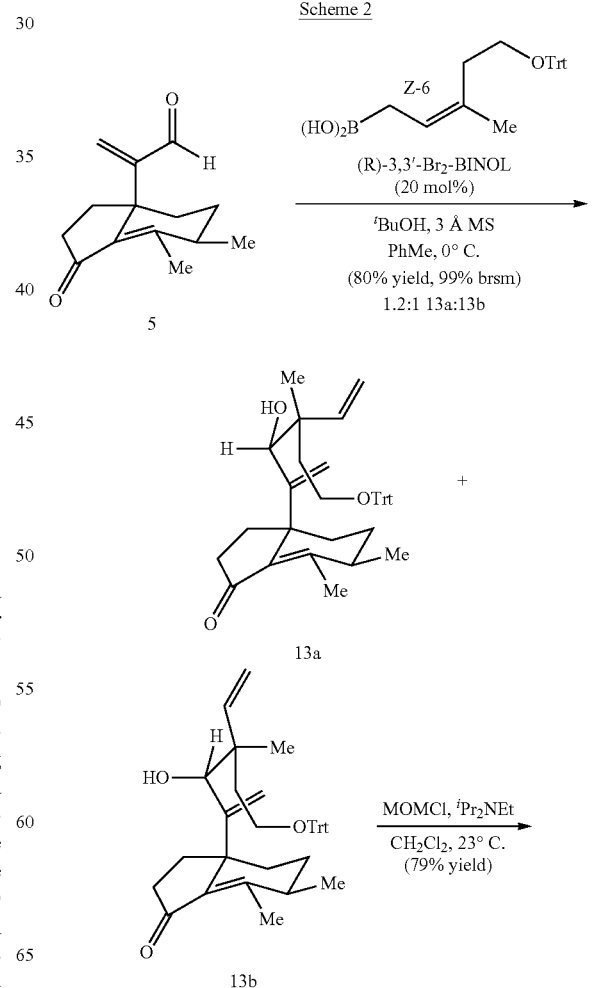

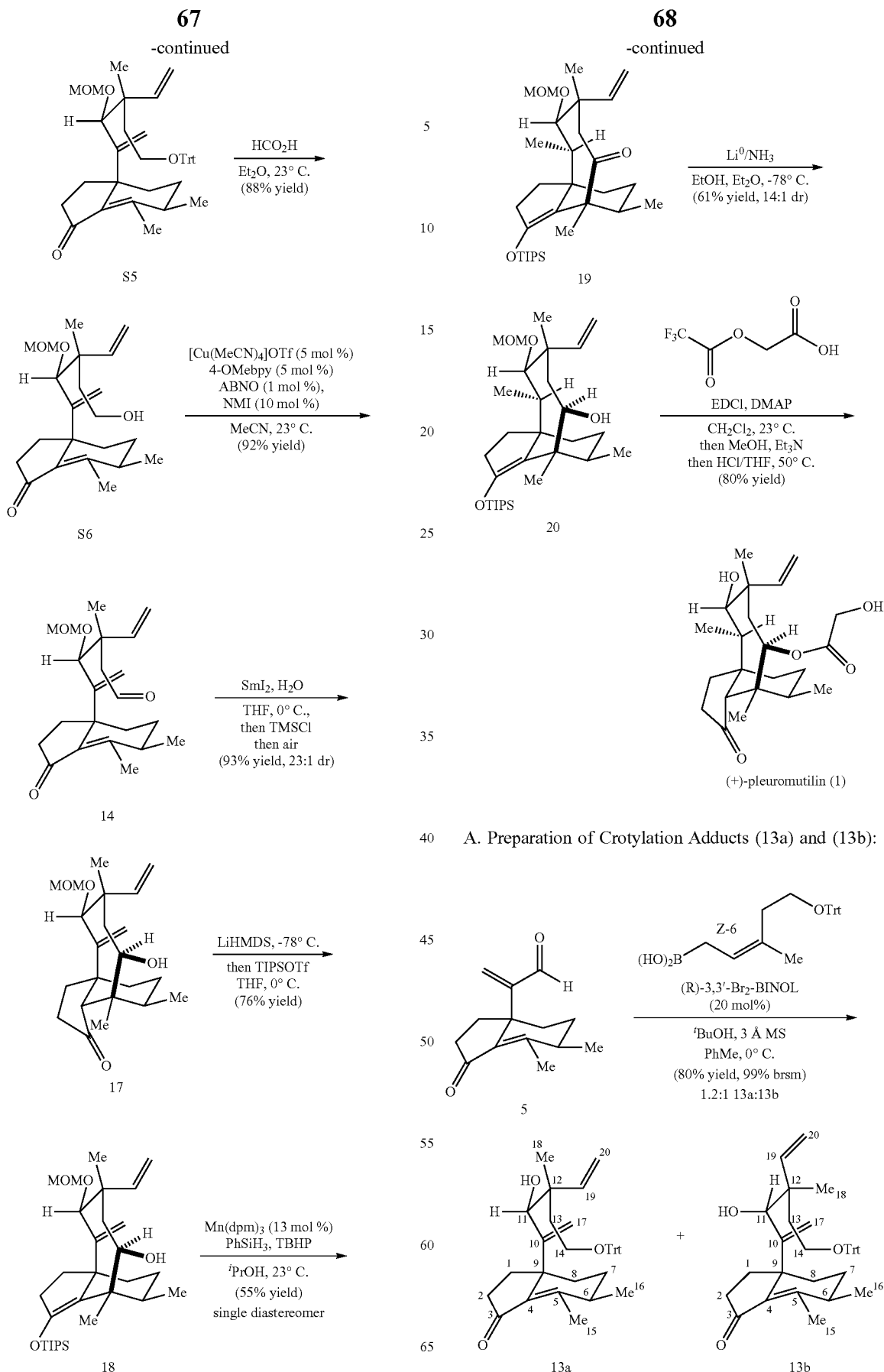
A. Preparation of Crotylation Adducts (13a) and (13b):

This procedure was adapted from the work of Szabó (*J. Am. Chem. Soc.* 2015, 137, 11262-11265). In a nitrogen-filled glovebox, a flame dried, 100 mL Schlenk flask equipped with a stir bar was charged with freshly activated 3 Å molecular sieves (pellets) (1.79 g), allylboronic acid Z-6 (25.3 mL of a 0.18 M solution, 4.47 mmol, 1 equiv), (R)-3,3'-Br$_2$-BINOL (397 mg, 0.894 mmol, 20 mol %), freshly distilled tBuOH (1.28 mL, 13.4 mmol, 3 equiv), and a solution of the enal hydrindanone 5 (976 mg, 4.47 mmol, 1 equiv) in dry, degassed PhMe (4.5 mL). The resulting heterogeneous mixture was sealed, removed from the glovebox, cooled to −30° C. for 5 min, then placed in a preequilibrated 0° C. bath and stirred. After 40 h, the reaction was quenched with MeOH (5 mL), stirred for 5 min, filtered, and concentrated under reduced pressure to afford a viscous residue.

Purification was achieved via flash column chromatography on SiO$_2$ [100 g SiO$_2$, Acetone/hexanes=4%→15%] to afford remaining enal (fractions 22-31), the desired diastereomer 13a (fractions 37-70), and 13b and residual (R)-3,3'-Br$_2$-BINOL (fractions 71-85). The volatiles were concentrated under reduced pressure to afford remaining enal (237 mg, 1.09 mmol, 24% recovered contaminated with ~5% protodeboronated nucleophile), the desired diastereomer 13a (1.03 g, 1.84 mmol, 41% yield), and the more polar diastereomer 13b/BINOL mixture respectively.

The 13b/BINOL mixture was subjected to flash column chromatography on SiO$_2$ [100 g SiO$_2$, Et$_2$O/hexanes=40%] to afford (R)-3,3'-Br$_2$-BINOL (fractions 1-3) and the more polar diastereomer 13b (fractions 23-38). Obtained (R)-3,3'-Br$_2$-BINOL (343 mg, 0.772 mmol, 86% recovered) and the more polar diastereomer 13b (972 mg, 1.73 mmol, 39% yield). Both diastereomers were isolated as puffy white foams.

Experimental Note:

It is critical that all operations be carried out in a rigorously oxygen-free environment. Failure to do so will result in rapid decomposition of the allylboronic acid.

Desired Diastereomer (13a)

TLC (desired diastereomer) (20% Acetone/hexanes): R$_f$=0.38 (UV, p-anisaldehyde).

$^1$H NMR (400 MHz, CDCl$_3$): δ 7.46-7.38 (m, 6H, Ph$_3$CO), 7.34-7.19 (m, 9H, Ph$_3$CO), 5.81 (dd, J=17.6, 10.9 Hz, 1H, C19), 5.41 (s, 1H, C17), 5.00 (dd, J=10.9, 1.2 Hz, 1H, C20), 4.95 (dd, J=17.7, 1.2 Hz, 1H, C20), 4.81 (d, J=1.1 Hz, 1H, C17), 3.89 (d, J=8.3 Hz, 1H, C11), 3.20 (t, J=6.7 Hz, 2H, C14), 2.34 (d, J=8.3 Hz, 1H, OH), 2.22 (app dt, J=10.0, 1.6 Hz, 1H, C8), 2.17 (m, 1H, C6), 2.17 (m, 1H, C2), 2.16 (s, 3H, C15), 2.09 (m, 1H, C1), 2.05 (m, 1H, C2), 1.86 (dt, J=13.5, 6.5 Hz, 1H, C13), 1.30 (td, J=13.5, 1.9 Hz, 1H, C7), 1.63 (m, 1H, C13), 1.54 (m, 1H, C1), 1.30 (td, J=13.5, 1.9 Hz, 1H, C7), (1.22, m, 1H, C8), 1.07 (s, 3H, C18), 1.05 (d, J=7.0 Hz, 3H, C16).

$^{13}$C NMR (101 MHz, CDCl$_3$): δ 208.1 (C3=O), 153.4 (C10), 152.4 (C5), 144.0 (Ph$_3$CO), 142.8 (C19), 135.7 (C4) 128.6 (Ph$_3$CO), 127.8 (Ph$_3$CO), 127.0 (Ph$_3$CO), 118.4 (C17), 114.7 (C20), 87.4 (Ph$_3$CO), 74.6 (C11), 60.8 (C14), 52.0 (C9), 44.6 (C12), 38.8 (C13), 38.0 (C6), 35.6 (C2), 33.2 (C8), 32.3 (C1), 28.2 (C7), 20.5 (C18), 19.1 (C16), 17.0 (C15).

FTIR (AT-IR): 3540, 2901, 2380, 2365, 1699, 1627, 1448, 1274, 1064, 1031, 749 cm$^{-1}$.

HRMS (TOF, ES+): calc'd for C$_{39}$H$_{44}$O$_3$Na [M+Na]$^+$ 583.3188, found 583.3198.

[α]$_D^{23}$: −104° (c=0.326, CHCl$_3$).

Melting point: 57.3-58.7° C.

11,12-Bis-Epi Crotylation Adduct (13b)

TLC (13b) (20% Acetone/hexanes): R$_f$=0.30 (UV, p-anisaldehyde).

$^1$H NMR (400 MHz, CDCl$_3$): δ 7.44-7.38 (m, 6H, Ph$_3$CO), 7.34-7.19 (m, 9H, Ph$_3$CO), 5.86 (dd, J=17.6, 10.9 Hz, 1H, C19), 5.48 (s, 1H, C17), 5.02 (dd, J=10.9, 1.2 Hz, 1H, C20), 4.96 (dd, J=17.7, 1.2 Hz, 1H, C20), 4.86 (d, J=1.1 Hz, 1H, C17), 3.82 (d, J=9.4 Hz, 1H, C11), 3.19 (m, 2H, C14), 2.50 (dd, J=12.3, 7.9 Hz, 1H, C2), 2.39 (d, J=8.3 Hz, 1H, OH), 2.28 (ddd, J=18.4, 12.8, 8.0 Hz, 1H, C1), 2.17 (m, 1H, C6), 2.16 (s, 3H, C15), 2.08 (d, J=7.9 Hz, 1H, C1), 2.01 (dd, J=16.5, 7.0 Hz, 1H, C13), 1.97 (dd, J=14.0, 6.8 Hz, 1H, C8), 1.63 (m, 1H, C7), 1.58 (q, J=6.6 Hz, C13), 1.46 (m, 1H, C2), 1.29 (m, 1H, C8), 1.26 (m, 1H, C7), 1.10 (d, J=7.0 Hz, 3H, C16), 1.06 (s, 3H, C18).

$^{13}$C NMR (101 MHz, CDCl$_3$): δ 208.4 (C3=O), 153.2 (C10), 151.1 (C5), 144.0 (Ph$_3$CO), 143.1 (C19), 136.4 (C4) 128.6 (Ph$_3$CO), 127.8 (Ph$_3$CO), 127.0 (Ph$_3$CO), 118.6 (C17), 114.6 (C20), 87.3 (Ph$_3$CO), 75.2 (C11), 60.9 (C14), 52.1 (C9), 44.3 (C12), 38.7 (C13), 37.8 (C6), 35.7 (C1), 32.7 (C8), 32.5 (C2), 28.3 (C7), 21.3 (C18), 19.2 (C16), 16.8 (C15).

FTIR (AT-IR): 3409, 2930, 2359, 2246, 1700, 1628, 1490, 1448, 1271, 1030, 759 cm$^{-1}$.

HRMS (TOF, ES+): calc'd for C$_{39}$H$_{44}$O$_3$Na [M+Na]$^+$ 583.3188, found 583.3184.

[α]$_D^{23}$: −55° (c=1.04, CHCl$_3$).

Melting point: 66.5-68.4° C.

B. Preparation of MOM Protected Crotylation Adduct (S5):

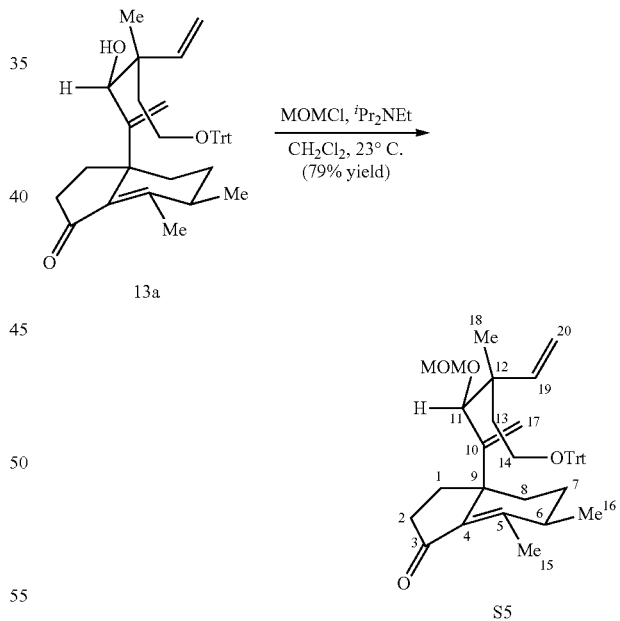

A flame-dried, 25 mL round bottom flask equipped with a stir bar was charged with alcohol 13a (300 mg, 0.535 mmol, 1 equiv), CH$_2$Cl$_2$ (8.7 mL), and freshly distilled iPr$_2$NEt (2.42 mL, 13.9 mmol, 26 equiv). To the homogeneous solution was added chloromethyl methyl ether (1.02 mL, 7.80 mmol, 25 equiv) dropwise over 10 min, taking care to vent HCl fumes formed via the use of a needle. The reaction was stirred at ambient temperature for 36 h. The resulting viscous, orange mixture was quenched via addition of sat. aq. NaHCO$_3$ (20 mL) and stirred at ambient temperature for 30 min. The aqueous layer was extracted with CH$_2$Cl$_2$ (3×10 mL). The combined organic layers were washed with H$_2$O (1×10 mL), brine (1×10 mL), dried over Na$_2$SO$_4$, and concentrated via distillation to afford a viscous, dark orange residue.

Purification was achieved via flash column chromatography on SiO$_2$ [35 g Sift, Et$_2$O/hexanes=16%→35%] to afford MOM ether S5 (281 mg, 0.465 mmol, 79% yield) as a puffy white solid. Starting material 13a was also isolated (38.0 mg, 0.0678 mmol, 13% recovered).

TLC (40% Et$_2$O/hexanes): R$_f$=0.71 (UV, p-anisaldehyde).

$^1$H NMR (400 MHz, CDCl$_3$): δ 7.46-7.38 (m, 6H, Ph$_3$CO), 7.32-7.19 (m, 9H, Ph$_3$CO), 5.77 (dd, J=16.9, 9.9 Hz, 1H, C19), 5.42 (d, J=1.1 Hz, 1H, C17), 4.93 (br m, 1H, C17), 4.84 (dd, J=9.9, 2.4 Hz, 1H, C20), 4.80 (dd, J=16.9, 2.4 Hz, 1H, C20), 4.52 (d, J=6.7 Hz, 1H, OCH2OMe), 4.46 (d, J=6.7 Hz, 1H, OCH2OMe), 3.87 (br s, 1H, C11), 3.37 (s, 3H, OCH2OCH3), 3.10 (m, m, 2H, C14), 2.17 (app dt, J=12.0, 7.9 Hz, 1H, C2), 2.15 (m, 1H, C1), 2.11 (m, 1H, C6), 2.10 (s, 3H, C15), 2.08 (m, 1H, C8), 1.98 (m, 1H, C13), 1.93 (m, 1H, C2), 1.86 (m, 1H, C13), 1.62 (m, 1H, C7), 1.44 (m, 1H, C1), 1.25 (m, 1H, C7), 1.23 (m, 1H, C8), 1.05 (d, J=7.0 Hz, 3H, C16), 0.99 (s, 3H, C18).

$^{13}$C NMR (101 MHz, CDCl$_3$): δ 208.4 (C3=O), 151.1 (C5), 149.7 (C10), 144.4 (Ph$_3$CO), 142.6 (C19), 136.4 (C4), 128.7 (Ph$_3$CO), 127.7 (Ph$_3$CO), 126.8 (Ph$_3$CO), 122.3 (C17), 113.9 (C20), 95.1 (OCH2OCH3), 86.7 (Ph$_3$CO), 80.2 (C11), 60.7 (C14), 56.4 (OCH2OCH3), 50.8 (C9), 45.2 (C12), 38.3 (C13), 37.5 (C6), 35.9 (C2), 33.2 (C8), 32.7 (C1), 28.2 (C7), 19.1 (C16), 17.9 (C18), 17.0 (C15).

FTIR (AT-IR): 2930, 1703, 1627, 1448, 1213, 1034, 919, 735 cm$^{-1}$.

HRMS (TOF, ES+): calc'd for C$_{41}$H$_{48}$O$_4$Na [M+Na]$^+$ 627.3450, found 627.3419.

[α]$_D^{23}$: −39° (c=1.06, CHCl$_3$).

Melting point: 62.0-63.3° C.

C. Preparation of Alcohol (S6):

formic acid (98%, 4.8 mL) and Et$_2$O (4.8 mL) was rapidly added, and within 5 min, the reaction was judged to be complete by TLC analysis. We found it critical to stop this reaction immediately after full conversion was achieved. Prolonged times afforded copious quantities of formate ester product. The reaction was diluted with Et$_2$O (10 mL) and quenched via slow addition of NaHCO$_3$ (100 mL). The aqueous layer was extracted with Et$_2$O (4×25 mL) and washed with H$_2$O (1×10 mL). The combined organic layers were washed with brine (1×5 mL), dried over Na$_2$SO$_4$, and concentrated under reduced pressure to afford a viscous yellow residue.

Purification was achieved via flash column chromatography on SiO$_2$ [15 g Sift, Et$_2$O/hexanes=70%] to afford alcohol S6 (225 mg, 0.621 mmol, 88% yield) as a viscous, colorless oil.

TLC (70% Et$_2$O/hexanes): R$_f$=0.20 (UV, p-anisaldehyde).

$^1$H NMR (400 MHz, CDCl$_3$): δ 5.99 (dd, J=16.9, 9.9 Hz, 1H, C19), 5.49 (d, J=1.1 Hz, 1H, C17), 5.05 (dd, J=9.9, 2.4 Hz, 1H, C20), 5.01 (br m, 1H, C17), 4.99 (dd, J=16.9, 2.4 Hz, 1H, C20), 4.58 (d, J=6.7 Hz, 1H, OCH2OMe), 4.50 (d, J=6.7 Hz, 1H, OCH2OMe), 4.01 (br s, 1H, C11), 3.66 (m, 2H, C14), 3.41 (s, 3H, OCH2OCH3), 2.24 (m, 1H, C2), 2.22 (m, 1H, C1), 2.13 (m, 1H, C6), 2.11 (m, 1H, C8), 2.10 (s, 3H, C15), 1.99 (m, 1H, C2), 1.95 (m, 1H, C13), 1.88 (m, 1H, C13), 1.63 (m, 1H, C7), 1.50 (m, 1H, C1), 1.27 (m, 1H, C8), 1.25 (m, 1H, C7), 1.12 (s, 3H, C18), 1.05 (d, J=7.0 Hz, 3H, C16).

$^{13}$C NMR (101 MHz, CDCl$_3$): δ 208.3 (C3=O), 151.2 (C5), 149.7 (C10), 143.1 (C19), 136.4 (C4), 122.5 (C17), 114.1 (C20), 95.0 (OCH2OCH3), 80.0 (C11), 59.8 (C14), 56.4 (OCH2OCH3), 50.7 (C9), 45.3 (C12), 41.5 (C13), 37.5 (C6), 35.9 (C2), 33.2 (C8), 32.8 (C1), 28.2 (C7), 19.1 (C16), 17.7 (C18), 17.0 (C15).

FTIR (AT-IR): 3397, 2930, 1701, 1625, 1456, 1371, 1212, 1145, 1035, 917, 734 cm$^{-1}$. HRMS (TOF, ES+): calc'd for C$_{22}$H$_{34}$O$_4$Na [M+Na]$^+$ 385.2355, found 385.2371.

[α]$_D^{23}$: −53° (c=0.475, CHCl$_3$).

D. Preparation of Aldehyde (14):

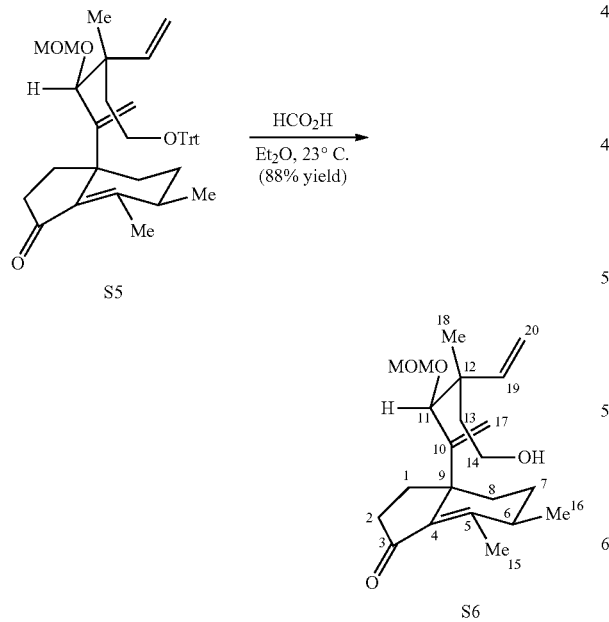

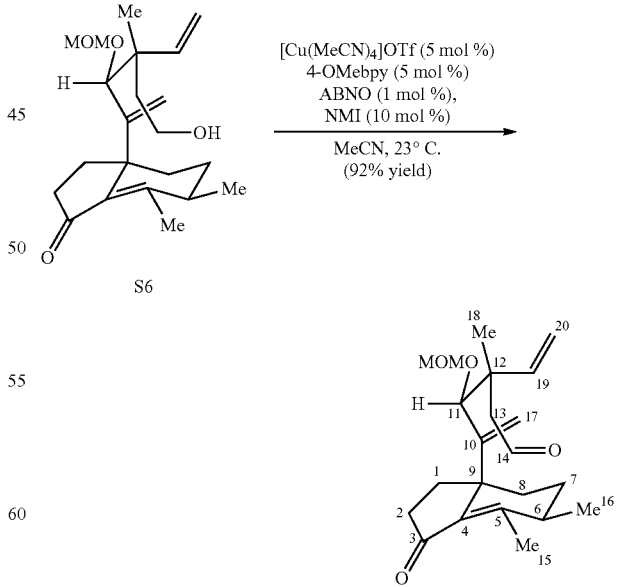

A flame-dried, 250 mL round bottom flask equipped with a stir bar was charged with MOM ether S5 (431 mg, 0.713 mmol, 1 equiv). Thereafter, a freshly prepared solution of See, Stahl, *J. Am. Chem. Soc.* 2013, 135, 15742-15745. A flame-dried, 2 dram vial equipped with a stir bar was charged with alcohol S6 (165 mg, 0.455 mmol, 1 equiv) and MeCN (2.0 mL). Thereafter, added 860 µL of the [Cu]/bpy stock solution, 860 µL of the NMI stock solution, and 860 µL of the ABNO stock solution, in that order. The orange reaction was stirred at 960 rpm open to the atmosphere for 90 min. Subsequently, the resulting light blue solution was diluted with Et$_2$O (10 mL), passed through a short pad of SiO$_2$ using Et$_2$O as the eluent and concentrated under reduced pressure to afford a pale yellow oil.

Purification was achieved via flash column chromatography on SiO$_2$ [8 g SiO$_2$, Et$_2$O/hexanes=30%→60%] to afford aldehyde 14 (151 mg, 0.419 mmol, 92% yield) as a viscous, colorless oil that solidified to a white solid upon standing in the freezer. Preparation of stock solutions: [Cu(MeCN)$_4$]OTf (30.0 mg) and 4,4'-dimethoxy-2,2'-bipyridyl (4-OMebpy) (17.0 mg) were suspended in MeCN (3.0 mL) and stirred for 5 min resulting in a homogeneous, green solution. ABNO (2.5 mg) was dissolved in MeCN (3.0 mL). N-methylimidazole (13.4 mg) was dissolved in MeCN (3.0 mL).

TLC (80% Et$_2$O/hexanes): R$_f$=0.65 (UV, p-anisaldehyde).

$^1$H NMR (400 MHz, CDCl$_3$): δ 9.74 (t, J=2.8 Hz, 1H, C14), 6.07 (dd, J=16.9, 9.9 Hz, 1H, C19), 5.48 (d, J=0.7 Hz, 1H, C17), 5.13 (dd, J=9.9, 2.4 Hz, 1H, C20), 5.09 (dd, J=16.9, 2.4 Hz, 1H, C20), 5.05 (br m, 1H, C17), 4.54 (d, J=6.7 Hz, 1H, OCH2OMe), 4.42 (d, J=6.7 Hz, 1H, OCH2OMe), 4.12 (br s, 1H, C11), 3.36 (s, 3H, OCH2OCH3), 2.56 (m, 2H, C13), 2.26 (m, 1H, C1), 2.19 (m, 1H, C8), 2.17 (m, 1H, C2), 2.14 (m, 1H, C6), 2.11 (s, 3H, C15), 2.00 (dd, J=17.0, 7.6 Hz, 1H, C2), 1.65 (m, 1H, C7), 1.52 (m, 1H, C1), 1.27 (s, 3H, C18), 1.25 (m, 1H, C8), 1.23 (m, 1H, C7), 1.07 (d, J=7.0 Hz, 3H, C16).

$^{13}$C NMR (101 MHz, CDCl$_3$): δ 208.1 (C3=O), 202.2 (C14=O), 151.4 (C5), 149.0 (C10), 142.4 (C19), 136.2 (C4), 122.7 (C17), 114.5 (C20), 94.2 (OCH2OCH3), 78.2 (C11), 56.6 (OCH2OCH3), 52.4 (C13), 50.5 (C9), 45.5 (C12), 37.4 (C6), 35.9 (C2), 33.1 (C8), 32.7 (C1), 28.2 (C7), 19.1 (C16), 18.9 (C18), 17.0 (C15).

FTIR (AT-IR): 2931, 1704, 1627, 1456, 1212, 1146, 1032, 919, 708 cm$^{-1}$.

HRMS (TOF, ES+): calc'd for C$_{22}$H$_{32}$O$_4$ [M+Na]$^+$ 383.2198, found 383.2189.

[α]$_D^{23}$: −56° (c=0.475, CHCl$_3$).

E. Preparation of Tricycle (17):

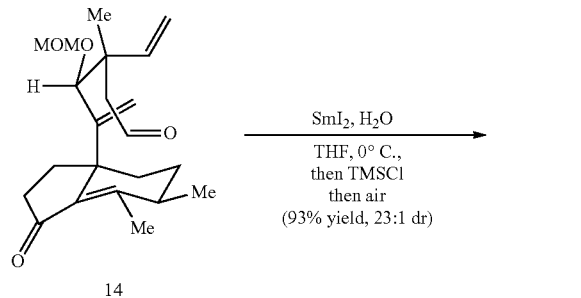

14

A 100 mL Schlenk flask equipped with a stir bar was charged with aldehyde 14 (108 mg, 0.300 mmol, 1 equiv), deionized H$_2$O (32 µL, 1.80 mmol, 6 equiv), and THF (15.0 mL) and submitted to five freeze-pump-thaw cycles. The solution was cooled to 0° C. and stirred at this temperature for 15 min. Thereafter, SmI$_2$/THF (9.0 mL, 0.900 mmol, 3 equiv) was added dropwise over 8 min. The deep blue color of SmI$_2$ was immediately quenched upon addition of each drop. The first drop afforded a yellow solution, fading to pale yellow and almost clear by the time 1.6 equiv SmI$_2$ had been added. When 2.2 equiv SmI$_2$ had been added, the blue color became increasingly persistent and upon addition of 2.6 equiv SmI$_2$, the reaction was dark blue/green. After stirring an additional 10 min at 0° C., TMSCl/THF (1.5 mL, 1.50 mmol, 5 equiv TMSCl) was added dropwise over 2 min, and the reaction was stirred an additional 10 min. Throughout this time, the deep blue color was quenched to yellow. Thereafter, the reaction was removed from the ice bath and stirred open to the atmosphere for 5 min.

The resulting pale yellow solution was diluted with Et$_2$O (75 mL), and washed with H$_2$O (2×15 mL). The aqueous layer was back-extracted with Et$_2$O (2×15 mL), and the combined organic layers were dried over Na$_2$SO$_4$, filtered, and concentrated under reduced pressure to afford a dark orange oil.

Purification was achieved via flash column chromatography on SiO$_2$ [12 g SiO$_2$, Et$_2$O/hexanes=30%] to afford tricycle 17 (100 mg, 0.276 mmol, 92% yield) as a crystalline white solid.

Preparation of SmI$_2$: A 100 mL Schlenk flask containing a stir bar was charged with freshly filed Sm metal (650 mg). The system was flame-dried under high vacuum then cooled to ambient temperature before adding freshly purified 1,2-diiodoethane (700 mg). 1,2-diiodoethane (1.6 g) was dissolved in Et$_2$O (50 mL) and washed with sat. aq. Na$_2$S$_2$O$_3$ (3×10 mL) and deionized water (2×10 mL), dried over Na$_2$SO$_4$, filtered, and dried to 1.41 g of a white solid. The atmosphere was exchanged three times for argon. Subsequently, the flask was charged with anhydrous THF (25 mL) that had been submitted to five freeze-pump-thaw cycles. Note: The THF used for the synthesis of SmI$_2$ must contain <50 ppm H$_2$O; THF containing greater quantities of water resulted in excessive induction times for the synthesis of SmI$_2$. Further, residual oxygen results in formation of oxidative fragmentation products in the radical cyclization. The suspension was stirred for 2 min and the flask was cautiously and briefly (5 s) placed under partial high vacuum, then purged with argon. This process was repeated two additional times to remove ethylene gas formed from insertion of Sm metal into 1,2-diiodoethane. The resulting heterogeneous suspension was rapidly (930 rpm) stirred; after 5 min, the reaction turned dark green, and within 10 min, a dark blue color was observed. After stirring under argon for 3 h at ambient temperature, the system was cautiously and briefly placed under high vacuum, then purged with argon. This process was repeated two additional times, then stirring was halted. The mixture was allowed to settle for 15 min prior to use.

Stock solution of TMSCl: TMSCl was freshly distilled from CaH$_2$ (5% w/w) under argon, collecting a 15% forerun then taking the middle fraction. A solution of TMSCl (350 µL) in THF (5.0 mL) was submitted to five freeze-pump thaw cycles.

TLC (50% Et$_2$O/hexanes): R$_f$=0.55 (p-anisaldehyde).

$^1$H NMR (400 MHz, CDCl$_3$): δ 6.35 (dd, J=17.8, 11.3 Hz, 1H, C19), 5.33 (dd, J=17.8, 1.4 Hz, 1H, C20), 5.34 (s, 1H, C17), 5.28 (s, 1H, C17), 5.19 (dd, J=11.2, 1.4 Hz, 1H, C20),

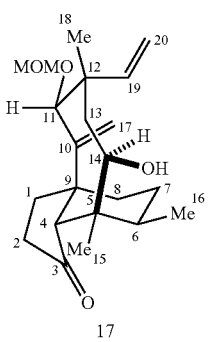

17

4.54 (d, J=7.1 Hz, 1H, OCH2OMe), 4.40 (d, J=6.7 Hz, 1H, OCH2OMe), 4.13 (d, J=5.9 Hz, 1H, C14), 3.95 (s, 1H, C11), 3.38 (s, 3H, OCH2OCH3), 2.33 (m, 1H, C2), 2.29 (m, 1H, C2), 2.24 (m, 1H, C4), 2.06 (m, 1H, C1), 2.03 (m, 1H, C8), 1.92 (dd, J=16.1, 6.5 Hz, 1H, C13), 1.70 (m, 1H, C6), 1.60 (dt, J=13.3, 3.4 Hz, 1H, C7), 1.50 (dd, J=16.1, 0.9 Hz, 1H, C13), 1.39 (ddt, J=13.3, 6.5, 3.4 Hz, 1H, C7), 1.33 (m, 1H, C1), 1.30 (s, 3H, C15), 1.28 (m, 1H, C8), 1.24 (s, 3H, C18), 0.96 (d, J=7.0 Hz, 3H, C16).

$^{13}$C NMR (101 MHz, CDCl$_3$): δ 216.8 (C3=O), 148.3 (C10), 139.9 (C19), 114.2 (C20), 112.2 (C17), 92.1 (OCH2OCH3), 77.2 (C11), 67.2 (C14), 59.6 (C4), 56.0 (OCH2OCH3), 46.5 (C9), 45.2 (C13), 44.7 (C12), 42.1 (C5), 37.3 (C6), 34.9 (C2), 31.0 (C8), 29.7 (C1), 28.8 (C18), 26.8 (C7), 18.2 (C16), 13.4 (C15).

FTIR (AT-IR): 3508 (br), 2926, 1735, 1628, 1458, 1264, 1144, 1093, 1024, 907, 738 cm$^{-1}$.

HRMS (TOF, ES+): calc'd for C$_{22}$H$_{35}$O$_4$ [M+H]$^+$ 363.2535, found 363.2536.

[α]$_D^{23}$: +155° (c=0.330, CHCl$_3$).

Melting point: 142.0-143.4° C.

F. Preparation of Silyl Enol Ether (18):

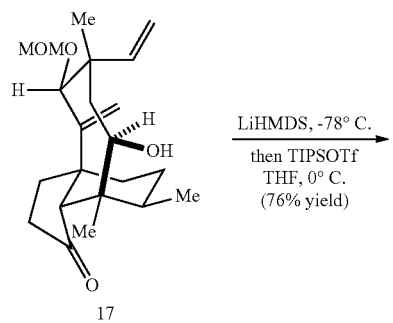

A flame-dried 25 mL round bottom flask equipped with a stir bar was charged with tricycle 17 (129 mg, 0.356 mmol, 1 equiv) and anhydrous THF (7.1 mL) under an atmosphere of argon. The mixture was cooled to −78° C. and stirred for 5 min prior to dropwise addition of LiHMDS in THF (1.07 mL of a 1.0 M solution, 1.07 mmol, 3 equiv) over 5 min. The resulting yellow solution was stirred at −78° C. for 5 min and was then placed in an ice bath and stirred for 5 min. Subsequently, TIPSOTf (191 µL, 0.712 mmol, 2 equiv) was added rapidly. After 3 min, the reaction was quenched at 0° C. via rapid addition of sat. aq. NaHCO$_3$ (3 mL) and vigorously stirred at 0° C. for 10 min. Thereafter, the mixture was extracted into Et$_2$O (3×20 mL) and the combined organic layers were washed with sat. aq. NaHCO$_3$ (3×10 mL) (note: failure to quench residual TIPSOTf in this manner resulted in extensive decomposition of product upon concentration). The combined organic layers were dried over Na$_2$SO$_4$, filtered, and concentrated under reduced pressure to afford a pale yellow oil.

Purification was achieved via flash column chromatography on SiO$_2$ [15 g SiO$_2$, Et$_2$O/hexanes=8%] to afford silyl enol ether 18 (141 mg, 0.272 mmol, 76% yield) as a puffy, viscous, colorless oil that formed a white solid upon standing in the freezer overnight.

TLC (15% Et$_2$O/hexanes): R$_f$=0.48 (p-anisaldehyde).

$^1$H NMR (400 MHz, CDCl$_3$): δ 6.39 (dd, J=17.8, 11.3 Hz, 1H, C19), 5.28 (dd, J=17.8, 1.4 Hz, 1H, C20), 5.17 (dd, J=11.2, 1.4 Hz, 1H, C20), 5.13 (s, 1H, C17), 5.05 (s, 1H, C17), 4.68 (d, J=7.1 Hz, 1H, OCH2OMe), 4.40 (d, J=6.7 Hz, 1H, OCH2OMe), 4.06 (m, 1H, C14), 3.64 (s, 1H, C11), 3.34 (s, 3H, OCH2OCH3), 2.53 (ddd, J=15.6, 10.2, 7.5 Hz, 1H, C2), 2.37 (dd, J=15.6, 11.0, 3.8 Hz, 1H, C2), 2.32 (dd, J=10.9, 3.6 Hz, 1H, C8), 2.11 (dd, J=15.0, 6.0 Hz, 1H, C13), 1.78 (ddd, J=13.9, 10.2, 3.8 Hz, 1H, C1), 1.64 (m, 1H, C7), 1.51 (m, 1H, C6), 1.46 (ddd, J=13.9, 6.3, 3.8 Hz, 1H, C1), 1.41 (m, 1H, C13), 1.40 (m, 1H, C7), 1.39 (m, 1H, C8), (s, 3H, C15), 1.17 (s, 3H, C18), 1.15 (m, 3H, OSi(CH(CH3)2)3), 1.12 (m, 18H, OSi(CH(CH3)2)3), 0.97 (d, J=7.0 Hz, 3H, C16).

$^{13}$C NMR (101 MHz, CDCl$_3$): δ 151.8 (C10), 147.8 (C3), 140.7 (C19), 119.2 (C4), 113.9 (C20), 108.9 (C17), 92.2 (OCH2OCH3), 79.0 (C11), 67.6 (C14), 55.6 (OCH2OCH3), 51.5 (C9), 46.9 (C13), 46.6 (C5), 44.8 (C12), 44.1 (C6), 38.8 (C8), 34.9 (C1), 34.4 (C2), 28.9 (C18), 28.7 (C7), 18.19 (OSi(CH(CH3)2)3), 18.15 (OSi(CH(CH3)2)3), 18.1 (C16), 16.4 (C15), 13.6 (OSi(CH(CH3)2)3).

FTIR (AT-IR): 3495 (br), 2941, 2866, 2359, 2323, 1627, 1462, 1327, 1040, 1002, 882 cm$^{-1}$.

HRMS (TOF, ES+): calc'd for C$_{31}$H$_{54}$O$_4$SiNa [M+Na]$^+$ 541.3689, found 541.3711.

[α]$_D^{23}$: +42.2° (c=0.490, CHCl$_3$).

Melting point: 99.8-101.1° C.

G. Preparation of Ketone (19):

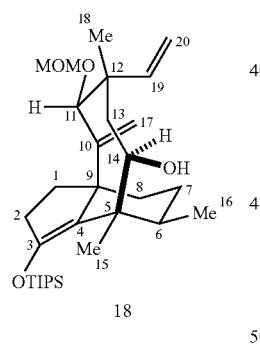

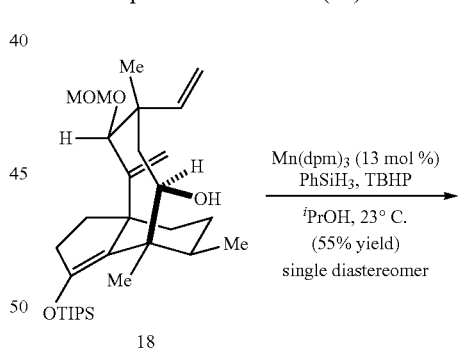

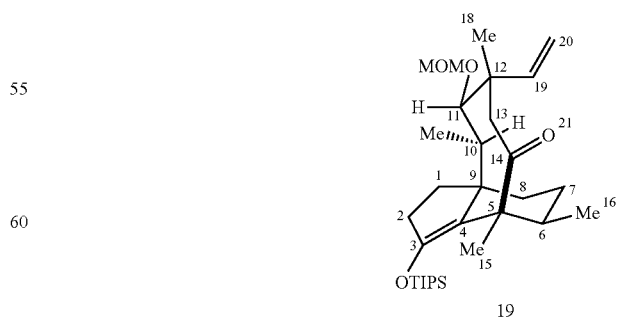

This procedure was adapted from the work of Shenvi (*J. Am. Chem. Soc.* 2014, 136, 1300). A flame-dried 25 mL Schlenk tube was charged with silyl enol ether 18 (116 mg, 0.224 mmol, 1 equiv) and adventitious water was removed via azeotropic drying with PhH (3×1 mL) under high vacuum. An oven-dried stir bar was added, and the atmosphere was exchanged three times for argon. Thereafter, iPrOH (3.4 mL), PhSiH₃ (36.3 mg, 0.336 mmol, 41.4 μL, 1.5 equiv), and tert-butyl hydroperoxide (89.5 μL of a 5.0 M solution in nonane, 0.448 mmol, 2 equiv) were added. The mixture was subjected to three freeze-pump-thaw cycles. Another Schlenk tube was charged with tris(2,2,6,6-tetramethyl-3,5-heptanedionato)manganese(III) (17.5 mg), and the atmosphere was exchanged three times for argon before adding iPrOH (1.4 mL). This solution was subjected to three freeze-pump-thaw cycles then purged with argon. A portion of this stock solution (1.1 mL, equating to 13.5 mg Mn(dpm)₃, 0.0224 mmol, 10 mol %) was added to the substrate solution, and the reaction was stirred at ambient temperature. The reaction began as a dark orange solution but became light yellow within 10 min. After 30 min, an additional portion (300 μL) of the Mn(dpm)₃ stock solution was added.

After 1 h, the reaction was passed through a plug of SiO₂ (eluting with Et₂O/hexanes=10%), and concentrated under reduced pressure to afford a dark orange oil that was immediately purified via flash column chromatography on SiO₂ [15 g Et₂O/hexanes=7%→11%] to afford ketone 19 (63.9 mg, 0.123 mmol, 55% yield) as a viscous, colorless oil.

In addition, the following were isolated: C19-C20 reduced product (9.9 mg, 0.0190 mmol, 8% yield) (15% Et₂O/hexanes, $R_f$=0.70 [p-anisaldehyde, stains green]), fully reduced product (4.4 mg, 0.00842 mmol, 4% yield, 1:1 dr) (15% Et₂O/hexanes, $R_f$=0.53 [p-anisaldehyde, stains dark blue]), and remaining starting material (26.6 mg, 0.0513 mmol, 23% recovered).

This reaction exhibits a pronounced sensitivity to both residual oxygen and water. In addition, we found it critical to perform this reaction at 23° C., as higher temperatures promoted over-reduction and lower temperatures slowed catalysis. iPrOH was stored over activated 4 Å molecular sieves (pellets) overnight then was distilled from CaH₂ (10% w/v) in a flame-dried, argon-filled apparatus immediately prior to use.

TLC (15% Et₂O/hexanes): $R_f$=0.60 (p-anisaldehyde).

¹H NMR (500 MHz, CDCl₃): δ 6.15 (dd, J=17.6, 11.1 Hz, 1H, C19), 5.28 (dd, J=17.6, 1.6 Hz, 1H, C20), 5.23 (dd, J=11.1, 1.6 Hz, 1H, C20), 4.69 (d, J=7.0 Hz, 1H, OCH2OMe), 4.62 (d, J=7.0 Hz, 1H, OCH2OMe), 3.40 (s, 3H, OCH2OCH3), 3.29 (d, J=4.6 Hz, 1H, C11), 2.80 (d, J=11.4 Hz, 1H, C13), 2.47 (m, 2H, C2), 2.04 (ddd, J=13.8, 10.2, 5.1 Hz, 1H, C1), 1.98 (dt, J=13.1, 3.0 Hz, 1H, C8), 1.95 (d, J=11.4 Hz, 1H, C13), 1.91 (dq, J=7.1, 4.6 Hz, 1H, C10), 1.65 (qd, J=13.8, 3.4 Hz, 1H, C7), 1.57 (s, 3H, C15), 1.43 (m, 1H, C6), 1.34 (m, 1H, C7), 1.31 (m, 1H, C1), 1.26 (m, 1H, C8), 1.24 (d, J=7.0 Hz, 3H, C16), 1.18 (m, 3H, OSi(CH(CH3)2)3), 1.13 (m, 18H, OSi(CH(CH3)2)3), 1.10 (s, 3H, C18), 0.83 (d, J=7.1 Hz, 3H, C17).

¹³C NMR (125 MHz, CDCl₃): δ 215.1 (C14=O), 148.2 (C3), 139.0 (C19), 117.8 (C4), 115.5 (C20), 99.3 (OCH2OCH3), 85.2 (C11), 56.4 (OCH2OCH3), 54.8 (C5), 51.5 (C9), 49.3 (C13), 48.3 (C12), 43.8 (C6), 39.4 (C8), 37.1 (C10), 34.0 (C2), 27.8 (C7), 27.5 (C1), 27.3 (C18), 22.2 (C15), 18.15 (OSi(CH(CH3)2)3), 18.11 (OSi(CH(CH3)2)3), 16.5 (C16), 13.6 (OSi(CH(CH3)2)3), 11.5 (C17).

FTIR (AT-IR): 2944, 2867, 1698, 1650, 1463, 1331, 1206, 1038, 1004 cm⁻¹.

HRMS (TOF, ES+): calc'd for C₃₁H₅₄O₄SiNa [M+Na]⁺ 541.3689, found 541.3701.

$[\alpha]_D^{23}$: −204.8° (c=1.48, CHCl₃).

H. Preparation of Alcohol (20):

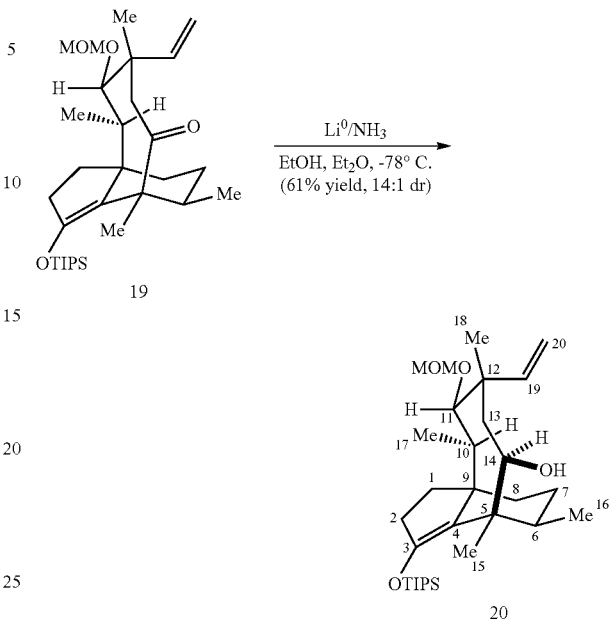

A 250 mL 3-necked flask equipped with a stir bar was equipped with a cold finger connected to a two-way valve, and the entire apparatus was flame-dried under high vacuum. After cooling to ambient temperature, the atmosphere was exchanged three times for argon, and anhydrous EtOH (13.3 mL) and Et₂O (7.3 mL) were added. The mixture was cooled to −78° C., and ammonia (53 mL) was condensed into the vessel. Subsequently, a solution of ketone 19 (41.4 mg, 0.0798 mmol, 1 equiv) in Et₂O (8.3 mL) was added. After allowing the system to equilibrate for 5 min, Li⁰ wire (124 mg, 17.9 mmol, 224 equiv) that had been freshly washed with hexanes and cut into ~5 mg pieces was added. Within 3 min, a deep blue color developed, and after 30 min, the reaction was colorless.

The apparatus was removed from the cooling bath, and ammonia was boiled off over 2 h. The resulting slurry was extracted into Et₂O (100 mL), washed with sat. aq. NaHCO₃ (1×15 mL), dried over Na₂SO₄, filtered, and concentrated under reduced pressure to afford an oil. Purification was achieved via flash column chromatography on SiO₂ [3 g SiO₂, Et₂O/hexanes=7%] to afford alcohol 20 (25.2 mg, 0.0487 mmol, 61% yield) as a viscous, colorless oil.

TLC (15% Et₂O/hexanes): $R_f$=0.41 (p-anisaldehyde).

¹H NMR (400 MHz, CDCl₃): δ 6.07 (ddd, J=17.9, 11.2 Hz, 0.7 Hz, 1H, C19), 5.28 (dd, J=17.9, 1.6 Hz, 1H, C20), 5.23 (dd, J=11.2, 1.6 Hz, 1H, C20), 4.64 (d, J=6.7 Hz, 1H, OCH2OMe), 4.62 (d, J=6.7 Hz, 1H, OCH2OMe), 4.16 (dd, J=7.1, 2.6 Hz, 1H, C14), 3.40 (s, 3H, OCH2OCH3), 3.01 (d, J=5.6 Hz, 1H, C11), 2.46-2.34 (m, 2H, C2), 2.04 (ddd, J=14.9, 7.8, 0.8 Hz, 1H, C13), 1.99 (m, 1H, C10), 1.96 (dt, J=9.4, 3.4 Hz, 1H, C1), 1.60 (d, J=14.9 Hz, 1H, C13), 1.46 (m, 1H, C7), 1.41 (m, 1H, C6), 1.40 (s, 3H, C15), 1.35 (m, 1H, C7), 1.23 (m, 1H, C8), 1.21 (m, 1H, C8), 1.17 (m, 1H, C1), 1.15 (m, 3H, OSi(CH(CH3)2)3), 1.13 (m, 18H, OSi(CH(CH3)2)3), 1.01 (s, 3H, C18), 0.99 (d, J=6.3 Hz, 3H, C16), 0.85 (d, J=7.1 Hz, 3H, C17).

¹³C NMR (101 MHz, CDCl₃): δ 147.0 (C3=O), 141.3 (C19), 120.5 (C4), 114.4 (C20), 99.2 (OCH2OCH3), 84.6 (C11), 68.6 (C14), 56.5 (OCH2OCH3), 50.7 (C9), 46.5

(C12), 46.1 (C13), 46.0 (C5), 43.3 (C6), 39.3 (C1), 38.2 (C10), 34.3 (C2), 30.0 (C18), 28.5 (C8), 28.3 (C7), 18.3 (C15), 18.24 (OSi(CH(CH3)2)3), 18.18 (OSi(CH(CH3)2) 3), 17.8 (C16), 13.8 (OSi(CH(CH3)2)3), 11.8 (C17).

FTIR (AT-IR): 3493 (br), 2944, 2866, 2359, 2341, 1637, 1461, 1218, 1038, 1002 cm$^{-1}$.

HRMS (TOF, ES+): calc'd for $C_{31}H_{55}O_4Si$ $[(M+H)-H_2]^+$ 519.3870, found 519.3873.

$[\alpha]_D^{23}$: −52.3° (c=0.342, $CHCl_3$).

I. Preparation of (+)-Pleuromutilin (1):

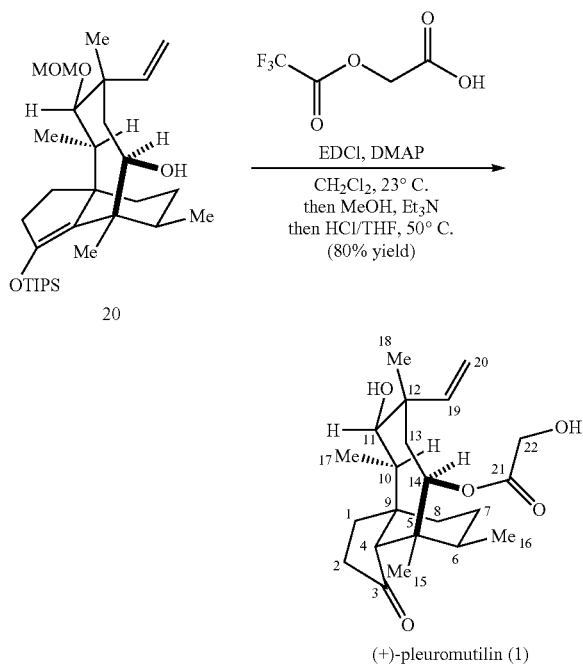

(+)-pleuromutilin (1)

This procedure was adapted from the work of Procter (*Chem. Eur. J.* 2013, 19, 6718). A flame-dried 2 dram vial equipped with a stir bar was charged with alcohol 20 (20.2 mg, 0.0388 mmol, 1 equiv), EDCI.HCl (44.6 mg, 0.233 mmol, 6 equiv), and DMAP (28.4 mg, 0.233 mmol, 6 equiv), and the atmosphere was exchanged three times for argon.

Subsequently, the vessel was charged with anhydrous $CH_2Cl_2$ (1.9 mL) and 2-(2,2,2-trifluoroacetoxy)acetic acid (40.0 mg, 0.230 mmol, 6 equiv), and the reaction was stirred at ambient temperature. After 10 min, a light yellow color developed, and after 30 min, the reaction was complete by TLC analysis (30% $Et_2O$/hexanes, $R_f$=0.77 [p-anisaldehyde, stains dark blue/purple], $R_f$(starting material)=0.70). Thereafter, a solution of anhydrous MeOH (31 μL, 0.776 mmol, 20 equiv) in freshly distilled $Et_3N$ (107 μL, 0.768 mmol, 20 equiv) was added, and the reaction immediately turned bright yellow. After 5 min, the reaction was judged was complete by TLC analysis (30% $Et_2O$/hexanes, $R_f$=0.35 [p-anisaldehyde, stains dark blue/purple]). A solution of HCl in THF (1.16 mL of a 2.0 M solution, 1.92 mmol) was added, and the reaction was heated to 50° C. After 30 min, an additional portion of HCl in THF (500 μL) was added. At this time, hydrolysis of the methoxymethyl group was judged complete by TLC analysis (70% $Et_2O$/hexanes, $R_f$=0.42 [p-anisaldehyde, stains dark blue/black]), and after 2 h global hydrolysis was complete.

The reaction was cooled to 0° C. and was cautiously quenched with sat. aq. $NaHCO_3$ (3 mL). After warming to ambient temperature, the crude mixture was extracted into $Et_2O$ (3×5 mL), dried over $Na_2SO_4$, filtered, and concentrated under reduced pressure to afford an orange oil. Purification was achieved via flash column chromatography on $SiO_2$ [1.5 g $SiO_2$, $Et_2O$/hexanes=50%→70%] to afford (+)-pleuromutilin 1 (11.8 mg, 0.0312 mmol, 80% yield) as a white solid.

TLC (70% $Et_2O$/hexanes): $R_f$=0.22 (p-anisaldehyde).

$^1$H NMR (500 MHz, $CDCl_3$): δ 6.50 (dd, J=17.4, 11.0 Hz, 1H, C19), 5.85 (d, J=8.6 Hz, 1H, C14), 5.37 (dd, J=11.0, 1.3 Hz, 1H, C20), 5.22 (dd, J=17.4, 1.4 Hz, 1H, C20), 4.05 (qd, J=17.1, 5.4 Hz, 2H, C22), 3.34 (dd, J=10.8, 6.6 Hz, 1H, C11), 2.35 (t, J=5.5 Hz, 1H, C22-OR), 2.33 (m, 1H, C10), 2.25 (m, 1H, C2), 2.22 (m, 1H, C2), 2.11 (br s, 1H, C4), 2.10 (dd, J=16.0, 8.7 Hz, 1H, C13), 1.79 (dq, J=14.5, 3.1 Hz, 1H, C8), 1.68 (m, 1H, C6), 1.66 (m, 1H, C1), 1.55 (dd, J=13.8, 2.7 Hz, 1H, C7), 1.51 (m, 1H, C1), 1.46 (br m, 1H, C12-OR), 1.44 (s, 3H, C15), 1.40 (ddd, J=13.8, 6.0, 2.7 Hz, 1H, C7), 1.33 (d, J=16.0 Hz, 1H, C13), 1.19 (s, 3H, C18), 1.15 (td, J=14.3, 4.4 Hz, 1H, C8), 0.91 (d, J=7.1 Hz, 3H, C17), 0.72 (d, J=7.1 Hz, 3H, C16).

$^{13}$C NMR (126 MHz, $CDCl_3$): δ 216.8 (C3=O), 172.1 (C21=O), 138.8 (C19), 117.4 (C20), 74.5 (C11), 69.8 (C14), 61.3 (C22), 58.0 (C4), 45.4 (C9), 44.7 (C13), 44.0 (C12), 41.8 (C5), 36.6 (C6), 36.0 (C10), 34.4 (C2), 30.4 (C8), 26.8 (C7), 26.3 (C18), 24.8 (C1), 16.6 (C16), 14.7 (C15), 11.5 (C17).

FTIR (AT-IR): 3437 (br), 2931, 1728, 1454, 1374, 1267, 1215, 1153, 1094, 1015, 915, 858, 734 cm$^{-1}$.

HRMS (TOF, ES+): calc'd for $C_{22}H_{34}O_5Na$ $[M+Na]^+$ 401.2304, found 401.2296.

$[\alpha]_D^{23}$: +33.4° (c=0.252, $CHCl_3$).

$[\alpha]_D^{23}$: +33° (c=0.25, $CHCl_3$).

Comparison of $^1$H NMR Data for (+)-Pleuromutilin (1)

| Proton Number | Natural (+)-Pleuromutilin[§]<br>$^1$H NMR, 500 MHz, $CDCl_3$<br>$^1$H [δ, multi, J (Hz)] | This Work,<br>Synthetic (+)-Pleuromutilin<br>$^1$H NMR, 500 MHz, $CDCl_3$<br>$^1$H [δ, multi, J (Hz)] |
|---|---|---|
| 1α | 1.41-1.53 (m) | 1.41-1.52 (m) |
| 1β | 1.61-1.73 (m) | 1.61-1.73 (m) |
| 2α | 2.16-2.30 (m) | 2.16-2.30 (m) |
| 2β | 2.16-2.30 (m) | 2.16-2.30 (m) |
| 3 | | |
| 4 | 2.11 (s) | 2.11 (s) |
| 5 | | |
| 6 | 1.61-1.73 (m) | 1.61-1.73 (m) |
| 7α | 1.55 (dd, J = 13.8, 2.7 Hz) | 1.55 (dd, J = 13.8, 2.7 Hz) |
| 7β | 1.40 (ddd, J = 13.8, 6.0, 2.7 Hz) | 1.40 (ddd, J = 13.8, 6.0, 2.7 Hz) |
| 8α | 1.79 (dq, J = 14.5, 3.1 Hz) | 1.79 (dq, J = 14.5, 3.1 Hz) |
| 8β | 1.15 (td, J = 14.3, 4.4 Hz) | 1.15 (td, J = 14.3, 4.4 Hz) |
| 9 | | |
| 10 | 2.29-2.40 (m) | 2.29-2.40 (m) |
| 11 | 3.34 (dd, J = 10.8, 6.6 Hz) | 3.34 (dd, J = 10.8, 6.6 Hz) |
| 12 | | |

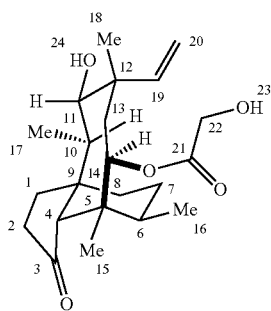

| Proton Number | Natural (+)-Pleuromutilin[§]<br>$^1$H NMR, 500 MHz, CDCl$_3$<br>$^1$H [δ, multi, J (Hz)] | This Work,<br>Synthetic (+)-Pleuromutilin<br>$^1$H NMR, 500 MHz, CDCl$_3$<br>$^1$H [δ, multi, J (Hz)] |
|---|---|---|
| 13α | 2.10 (dd, J = 16.0, 8.7 Hz) | 2.10 (dd, J = 16.0, 8.7 Hz) |
| 13β | 1.33 (d, J = 16.0 Hz) | 1.33 (d, J = 16.0 Hz) |
| 14 | 5.85 (d, J = 8.6 Hz) | 5.85 (d, J = 8.6 Hz) |
| 15 | 1.44 (s) | 1.44 (s) |
| 16 | 0.71 (d, J = 7.1 Hz) | 0.71 (d, J = 7.1 Hz) |
| 17 | 0.90 (d, J = 7.1 Hz) | 0.90 (d, J = 7.1 Hz) |
| 18 | 1.18 (s) | 1.18 (s) |
| 19 | 6.50 (dd, J = 17.4, 11.0 Hz) | 6.50 (dd, J = 17.4, 11.0 Hz) |
| 20α | 5.37 (dd, J = 11.0, 1.4 Hz) | 5.37 (dd, J = 11.0, 1.3 Hz) |
| 20β | 5.22 (d, J = 17.4, 1.4 Hz) | 5.22 (dd, J = 17.4, 1.4 Hz) |
| 21 | | |
| 22 | 4.05 (qd, J = 17.1, 5.4 Hz) | 4.05 (qd, J = 17.1, 5.4 Hz) |
| 23 | 2.30-2.40 (br)* | 2.30-2.40 (br)* |
| 24 | 1.44-1.52 (br)*s | 1.44-1.52 (br)* |

*Signals disappeared upon D2O quench

[§] Spectrum acquired using a sample of natural (+)-pleuromutilin purchased from Sigma-Aldrich (SML0285-5MG, Lot #032M4709V)

Comparison of $^{13}$C NMR Data for (+)-Pleuromutilin (1)

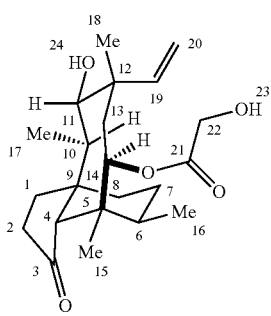 [SMILES: C=CC1(C)C[C@@H](OC(=O)CO)[C@]2(C)C(C)CCC3(CCC(=O)C32)[C@@H](C)C1O]

| Carbon Number | Schulz and Berner Report[10], Natural (+)-Pleuromutilin<br>$^{13}$C NMR, 90 MHz, CDCl$_3$<br>$^{13}$C (δ) ppm | This Work, Synthetic (+)-Pleuromutilin<br>$^{13}$C NMR, 126 MHz, CDCl$_3$<br>$^{13}$C (δ) ppm | Chemical Shift Difference |
|---|---|---|---|
| 1 | 24.9 | 24.8 | 0.1 |
| 2 | 34.5 | 34.4 | 0.1 |
| 3 | 216.8 | 216.8 | 0 |
| 4 | 58.2 | 58.0 | 0.2 |
| 5 | 41.9 | 41.8 | 0.1 |
| 6 | 36.7 | 36.6 | 0.1 |
| 7 | 26.9 | 26.8 | 0.1 |
| 8 | 30.4 | 30.4 | 0 |
| 9 | 45.5 | 45.4 | 0.1 |
| 10 | 36.1 | 36.0 | 0.1 |
| 11 | 74.7 | 74.5 | 0.2 |

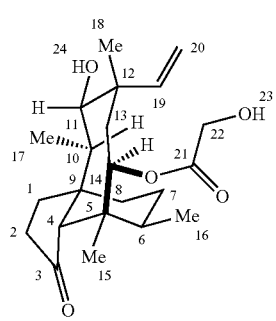 [SMILES: C=CC1(C)C[C@@H](OC(=O)CO)[C@]2(C)C(C)CCC3(CCC(=O)C32)[C@@H](C)C1O]

| Carbon Number | Schulz and Berner Report[10], Natural (+)-Pleuromutilin<br>$^{13}$C NMR, 90 MHz, CDCl$_3$<br>$^{13}$C (δ) ppm | This Work, Synthetic (+)-Pleuromutilin<br>$^{13}$C NMR, 126 MHz, CDCl$_3$<br>$^{13}$C (δ) ppm | Chemical Shift Difference |
|---|---|---|---|
| 12 | 44.1 | 44.0 | 0.1 |
| 13 | 44.9 | 44.7 | 0.2 |
| 14 | 69.9 | 69.8 | 0.1 |
| 15 | 14.8 | 14.7 | 0 |
| 16 | 16.6 | 16.6 | 0 |
| 17 | 11.5 | 11.5 | 0 |
| 18 | 26.5 | 26.3 | 0.2 |
| 19 | 138.9 | 138.8 | 0.1 |
| 20 | 117.3 | 117.4 | 0.1 |
| 21 | 172.2 | 172.1 | 0.1 |
| 22 | 61.4 | 61.3 | 0.1 |

Example 3: Synthesis of (+)-12-Epi-Pleuromutilin

Scheme 3

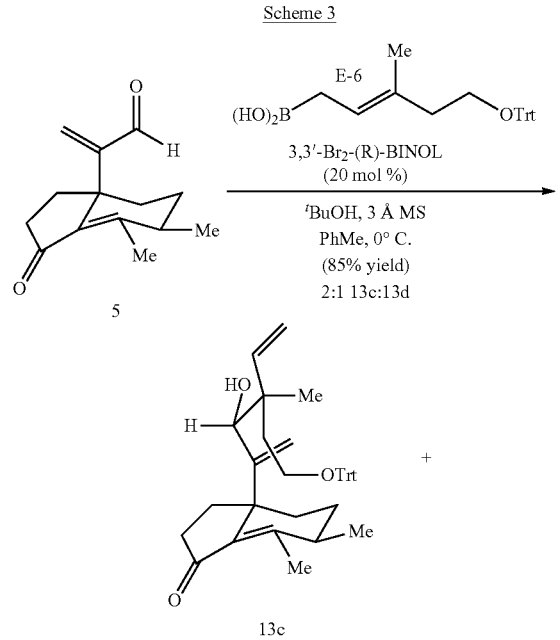

-continued

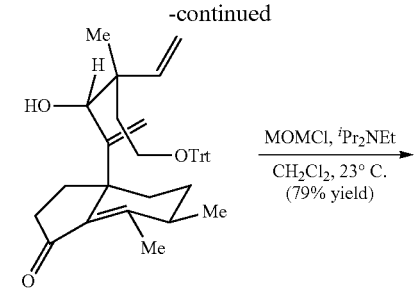

13d

MOMCl, $^i$Pr$_2$NEt
CH$_2$Cl$_2$, 23° C.
(79% yield)

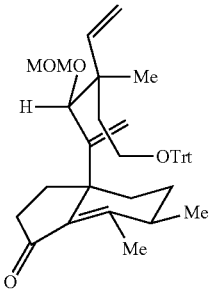

12-epi-S5

HCO$_2$H
Et$_2$O, 23° C.
(87% yield)

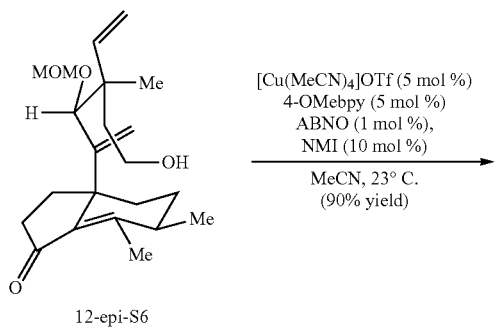

12-epi-S6

[Cu(MeCN)$_4$]OTf (5 mol %)
4-OMebpy (5 mol %)
ABNO (1 mol %),
NMI (10 mol %)
MeCN, 23° C.
(90% yield)

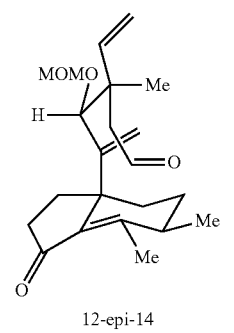

12-epi-14

SmI$_2$, H$_2$O
THF, 0° C.,
then TMSCl
then H$_2$O
(77% yield, 17:1 dr)

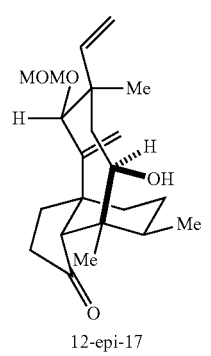

12-epi-17

LiHMDS, -78° C.
then TIPSOTf
THF, 0° C.
(quantitative)

-continued

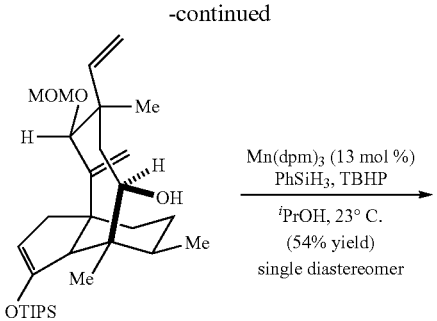

12-epi-18

Mn(dpm)$_3$ (13 mol %)
PhSiH$_3$, TBHP
$^i$PrOH, 23° C.
(54% yield)
single diastereomer

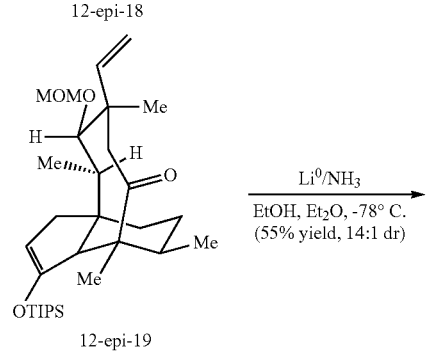

12-epi-19

Li$^0$/NH$_3$
EtOH, Et$_2$O, -78° C.
(55% yield, 14:1 dr)

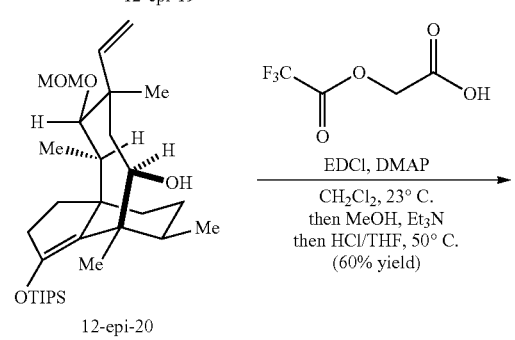

12-epi-20

EDCl, DMAP
CH$_2$Cl$_2$, 23° C.
then MeOH, Et$_3$N
then HCl/THF, 50° C.
(60% yield)

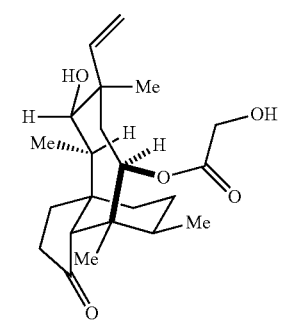

(+)-12-epi-pleuromutilin (12-epi-1)

A. Preparation of 12-epi (13c) and 11-epi (13d) crotylation adducts:

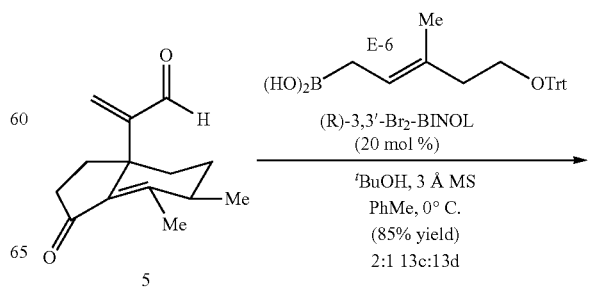

(R)-3,3'-Br$_2$-BINOL
(20 mol %)
$^t$BuOH, 3 Å MS
PhMe, 0° C.
(85% yield)
2:1 13c:13d

5

-continued

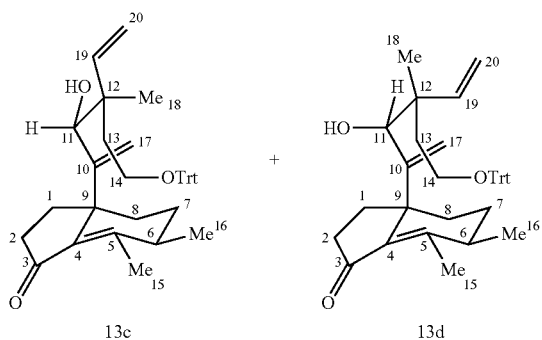

This procedure was adapted from the work of Szabó described above. In a nitrogen-filled glovebox, a flame dried, 50 mL Schlenk flask equipped with a stir bar was charged with freshly activated 3 Å molecular sieves (pellets) (613 mg), allylboronic acid E-6 (11.5 mL of a 0.15 M solution, 1.68 mmol, 1 equiv, see S40), (R)-3,3'-Br$_2$-BINOL (149 mg, 0.336 mmol, 20 mol %), freshly distilled tBuOH (483 μL, 5.09 mmol, 3 equiv), and a solution of the enal hydrindanone 5 (367 mg, 1.68 mmol, 1 equiv) in dry, degassed PhMe (1.68 mL). The resulting heterogeneous mixture was sealed, removed from the glovebox, then placed in a pre-equilibrated 0° C. bath and stirred.

After 40 h, the reaction was quenched with MeOH (5 mL), stirred for 5 min, filtered, and concentrated under reduced pressure to afford a viscous residue. Purification was achieved via flash column chromatography on SiO$_2$ [100 g SiO$_2$, Acetone/hexanes=4%→15%] to afford 13c and a mixture of 13d and residual (R)-3,3'-Br$_2$-BINOL (fractions 71-85). The volatiles were concentrated under reduced pressure to afford 13c (566 mg, 1.01 mmol, 60% yield) as a puffy white solid and the 13d/BINOL mixture, respectively. The 13d/BINOL mixture was subjected to flash column chromatography on SiO$_2$ [100 g SiO$_2$, Et$_2$O/hexanes=40%] to afford (R)-3,3'-Br$_2$-BINOL and 13d (237 mg, 0.423 mmol, 25% yield) as a puffy white solid.

Experimental Note:

It is critical that all operations be carried out in a rigorously oxygen-free environment. Failure to do so will result in rapid decomposition of the allylboronic acid.

12-Epi Crotylation Adduct (13c)

TLC (20% acetone/hexanes): R$_f$=0.54 (UV, p-anisaldehyde).

$^1$H NMR (400 MHz, CDCl$_3$): δ 7.43 (dd, J=8.4, 1.3 Hz, 6H, OCPh3), 7.34-7.19 (m, 9H, OCPh3), 6.15 (dd, J=17.8, 10.9 Hz, 1H, C19), 5.59 (s, 1H, C17), 5.04 (dd, J=10.9, 1.2 Hz, 1H, C20), 4.92 (dd, J=17.8, 1.3 Hz, 1H, C20), 4.76 (s, 1H, C17), 4.01 (d, J=6.7 Hz, 1H, C11), 3.21 (dt, J=10.0, 6.3 Hz, 1H, C14), 3.11 (ddd, J=9.9, 7.4, 5.4 Hz, 1H, C14), 2.54 (d, J=7.0 Hz, 1H, OH), 2.22-2.05 (m, 8H, C1, C2, C6, C8), 1.92 (dd, J=13.5, 6.2 Hz, 1H, C13), 1.80 (dd, J=12.9, 6.9 Hz, 1H, C13), 1.64 (dtd, J=15.5, 6.1, 5.1, 3.5 Hz, 1H, C7), 1.57-1.46 (m, 1H, C1), 1.36-1.13 (m, 3H, C7, C8), 1.05 (d, J=7.1 Hz, 3H, C16), 0.88 (s, 3H, C18).

$^{13}$C NMR (101 MHz, CDCl$_3$): δ 208.0 (C3=O), 152.8 (C10), 152.5 (C5), 143.9 (OCPh3), 142.8 (C19), 135.7 (C4), 128.6 (OCPh3), 127.8 (OCPh3), 127.0 (OCPh3), 118.4 (C17), 113.9 (C20), 87.4 (OCPh3), 74.4 (C11), 60.7 (C14), 52.0 (C9), 44.5 (C12), 40.0 (C13), 38.0 (C6), 35.5 (C2), 33.2 (C8), 32.4 (C1), 28.4 (C7), 19.9 (C18), 19.1 (C16), 17.0 (C15).

FTIR (thin film, NaCl): 3416, 2930, 1702, 1627, 1448, 1213, 1032, 758, 632 cm$^{-1}$.

HRMS (TOF, ES+): calc'd for C$_{39}$H$_{44}$O$_3$Na [M+Na]$^+$ 583.3188, found 583.3174.

[α]$_D^{23}$: −72.0° (c=0.41, CHCl$_3$).

11-Epi Crotylation Adduct (13d)

TLC (40% Et$_2$O/hexanes): R$_f$=0.14 (UV, p-anisaldehyde).

$^1$H NMR (400 MHz, CDCl$_3$): δ 7.46-7.39 (m, 6H, OCPh3), 7.33-7.20 (m, 9H, OCPh3), 6.15 (dd, J=17.8, 10.9 Hz, 1H, C19), 5.62 (s, 1H, C17), 5.04 (dd, J=10.9, 1.3 Hz, 1H, C20), 4.95 (dd, J=17.8, 1.4 Hz, 1H, C20), 4.77 (s, 1H, C17), 3.95 (d, J=7.3 Hz, 1H, C11), 3.26-3.16 (m, 1H, C14), 3.15-3.05 (m, 1H, C14), 2.62 (d, J=7.4 Hz, 1H, OH), 2.47 (dd, J=12.2, 7.9 Hz, 1H, C2), 2.32-2.17 (m, 1H, C8), 2.15 (d, J=5.9 Hz, 1H, C6), 2.12 (s, 3H, C15), 2.04 (dd, J=18.4, 7.6 Hz, 1H, C8), 1.95 (dd, J=12.5, 7.2 Hz, 1H, C13), 1.89 (d, J=13.2 Hz, 1H, C1), 1.85-1.76 (m, 1H, C13), 1.65-1.56 (m, 1H, C7), 1.42 (td, J=12.5, 7.9 Hz, 1H, C2), 1.33-1.11 (m, 3H, C1, C7), 1.06 (d, J=7.1 Hz, 3H, C16), 0.89 (s, 3H, C18).

$^{13}$C NMR (101 MHz, CDCl$_3$): δ 208.4 (C3=O), 152.2 (C10), 151.0 (C5), 143.9 (OCPh3), 142.9 (C19), 136.3 (C4), 128.6 (OCPh3), 127.8 (OCPh3), 127.0 (OCPh3), 118.7 (C17), 113.9 (C20), 87.5 (OCPh3), 74.7 (C11), 60.7 (C14), 52.0 (C9), 44.3 (C12), 40.2 (C13), 37.5 (C6), 35.8 (C8), 32.7 (C1), 32.5 (C2), 28.2 (C7), 20.4 (C18), 19.2 (C16), 16.8 (C15).

FTIR (thin film, NaCl): 3451, 2930, 1702, 1630, 1449, 1214, 1066, 923, 759, 705 cm$^{-1}$.

HRMS (TOF, ES+): calc'd for C$_{39}$H$_{44}$O$_3$Na [M+Na]$^+$ 583.3188, found 583.3178.

[α]$_D^{23}$: −53.4° (c=0.585, CHCl$_3$).

B. Preparation of MOM Protected Crotylation Adduct (12-Epi-S5):

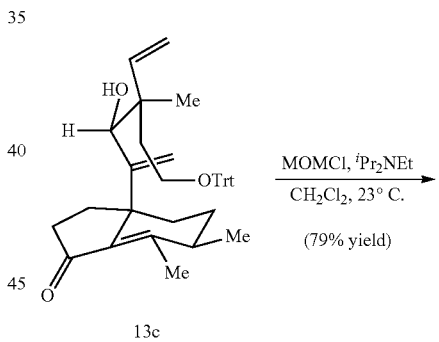

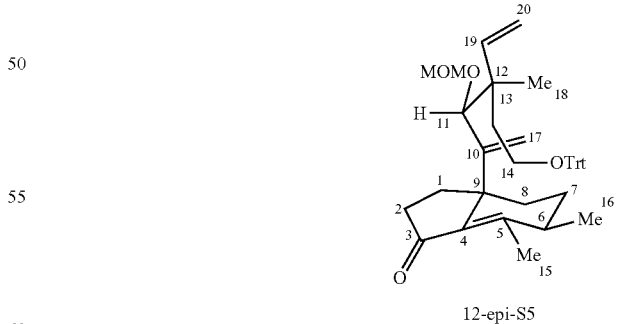

A flame-dried, 50 mL round bottom flask equipped with a stir bar was charged with alcohol 13c (535 mg, 0.954 mmol, 1 equiv), CH$_2$Cl$_2$ (4.8 mL), and freshly distilled iPr$_2$NEt (4.3 mL, 24.7 mmol, 26 equiv). To the homogeneous solution was added chloromethyl methyl ether (1.8 mL, 23.8 mmol, 25 equiv) dropwise over 10 min, taking care to vent HCl fumes formed via the use of a needle. The reaction was stirred at ambient temperature for 20 h. The resulting viscous, orange mixture was quenched via addition of sat. aq. NaHCO$_3$ (20 mL) and stirred at ambient temperature for 30 min. The aqueous layer was extracted with CH$_2$Cl$_2$ (3×10 mL) and washed with H$_2$O (1×10 mL). The combined organic layers were washed with brine (1×10 mL), dried over Na$_2$SO$_4$, and concentrated via distillation to afford a viscous, dark orange residue.

Purification was achieved via flash column chromatography on SiO$_2$ [50 g SiO$_2$, Et$_2$O/hexanes=20%] to afford MOM ether 12-epi-S5 (455 mg, 0.75 mmol, 79% yield) as a puffy white solid.

TLC (40% Et$_2$O/hexanes): R$_f$=0.56 (UV, p-anisaldehyde).

$^1$H NMR (400 MHz, CDCl$_3$): δ 7.42 (m, 6H, OCPh3), 7.32-7.17 (m, 9H, OCPh3), 5.88 (dd, J=17.7, 10.9 Hz, 1H, C19), 5.49 (s, 1H, C17), 4.93 (dd, J=10.9, 1.2 Hz, 1H, C20), 4.86 (s, 1H, C17), 4.79 (dd, J=17.7, 1.2 Hz, 1H, C20), 4.59 (d, J=6.7 Hz, 1H, OCH2OCH3), 4.55 (d, J=6.7 Hz, 1H, OCH2OCH3), 3.84 (s, 1H, C11), 3.38 (s, 3H, OCH2OCH3), 3.14-3.00 (m, 2H, C14), 2.22-2.04 (m, 8H, C1, C2, C6, C7, C15), 1.98-1.81 (m, 2H, C13), 1.67-1.57 (m, 1H, C8), 1.56-1.40 (m, 1H, C1), 1.28-1.20 (m, 2H, C7, C8), 1.06 (d, J=7.1 Hz, 3H, C16), 0.93 (s, 3H, C18).

$^{13}$C NMR (101 MHz, CDCl$_3$): δ 208.1 (C3=O), 151.8 (C5), 149.8 (C10), 144.4 (OCPh3), 143.2 (C19), 136.2 (C4), 128.7 (OCPh3), 127.7 (OCPh3), 126.8 (OCPh3), 121.4 (C17), 113.8 (C20), 96.4 (OCH2OCH3), 86.8 (OCPh3), 82.1 (C11), 60.7 (C14), 56.4 (OCH2OCH3), 51.0 (C9), 45.3 (C12), 37.7 (C6), 36.9 (C13), 35.9 (C2), 33.4 (C7), 32.5 (C1), 28.2 (C8), 19.7 (C19), 19.1 (C16), 17.1 (C15).

FTIR (thin film, NaCl): 3418, 2931, 2071, 1704, 1628, 1449, 1214, 1036, 920, 760 cm$^{-1}$.

HRMS (TOF, ES+): calc'd for C$_{41}$H$_{48}$O$_4$Na [M+Na]$^+$ 627.3450, found 627.3444.

[α]$_D^{23}$: −52.6° (c=0.965, CHCl$_3$).

C. Preparation of Alcohol (12-Epi-S6):

0.549 mmol, 1 equiv). Thereafter, a freshly prepared solution of formic acid (98%, 3.4 mL) and Et$_2$O (3.4 mL) was rapidly added, and within 5 min, the reaction was judged to be complete by TLC analysis. We found it critical to stop this reaction immediately after full conversion was achieved. Prolonged times afforded copious quantities of formate ester product. The reaction was diluted with Et$_2$O (15 mL) and quenched via slow addition of NaHCO$_3$ (100 mL). The aqueous layer was extracted with Et$_2$O (4×25 mL) and washed with H$_2$O (1×10 mL).

The combined organic layers were washed with brine (1×25 mL), dried over Na$_2$SO$_4$, and concentrated under reduced pressure to afford a viscous yellow residue. Purification was achieved via flash column chromatography on Sift [7 g SiO$_2$, Et$_2$O/hexanes=70%] to afford alcohol 12-epi-S6 (173 mg, 0.477 mmol, 87% yield) as a viscous, colorless oil.

TLC (40% Et$_2$O/hexanes): R$_f$=0.13 (UV, p-anisaldehyde).

$^1$H NMR (400 MHz, CDCl$_3$): δ 6.07 (dd, J=17.8, 10.9 Hz, 1H, C19), 5.58 (s, 1H, C17), 5.11 (dd, J=10.9, 1.1 Hz, 1H, C20), 5.03 (dd, J=17.8, 1.2 Hz, 1H, C20), 4.92 (s, 1H, C17), 4.65 (d, J=6.8 Hz, 1H, OCH2OCH3), 4.59 (d, J=6.8 Hz, 1H, OCH2OCH3), 3.94 (s, 1H, C11), 3.66 (td, J=6.9, 3.0 Hz, 2H, C14), 3.42 (s, 3H, OCH2OCH3), 2.30-2.11 (m, 8H, C1, C2, C6, C8, C15), 1.89 (td, J=6.8, 4.1 Hz, 2H, C13), 1.66-1.54 (m, 2H, C1, C7), 1.31-1.23 (m, 2H, C7, C8), 1.11 (s, 3H), 1.07 (d, J=7.0 Hz, 3H).

$^{13}$C NMR (101 MHz, CDCl$_3$): δ 207.9 (C3=O), 151.9 (C5), 149.8 (C10), 143.7 (C19), 136.1 (C4), 121.7 (C17), 114.0 (C20), 96.2 (OCH2OCH3), 82.1 (C11), 59.7 (C14), 56.4 (OCH2OCH3), 50.9 (C9), 45.4 (C12), 39.9 (C13), 37.7 (C7), 35.8 (C2), 33.4 (C8), 32.5 (C1), 28.1 (C7), 19.8 (C18), 19.0 (C16), 17.0 (C15).

FTIR (thin film, NaCl): 3417, 2931, 1704, 1627, 1455, 1212, 1152, 1036, 918, 731 cm$^{-1}$.

HRMS (TOF, ES+): calc'd for C$_{22}$H$_{34}$O$_4$Na [M+Na]$^+$ 385.2355, found 385.2344.

[α]$_D^{23}$: −43.8° (c=0.230, CHCl$_3$).

D. Preparation of Aldehyde (12-Epi-14):

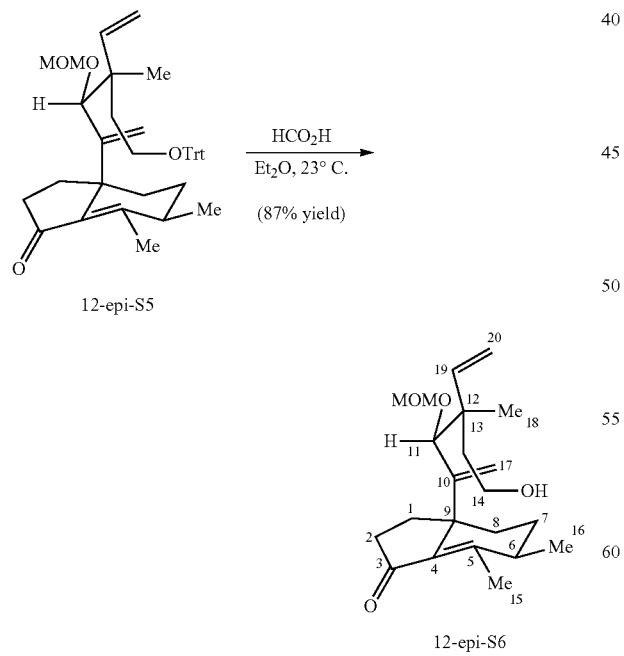

12-epi-S5

12-epi-S6

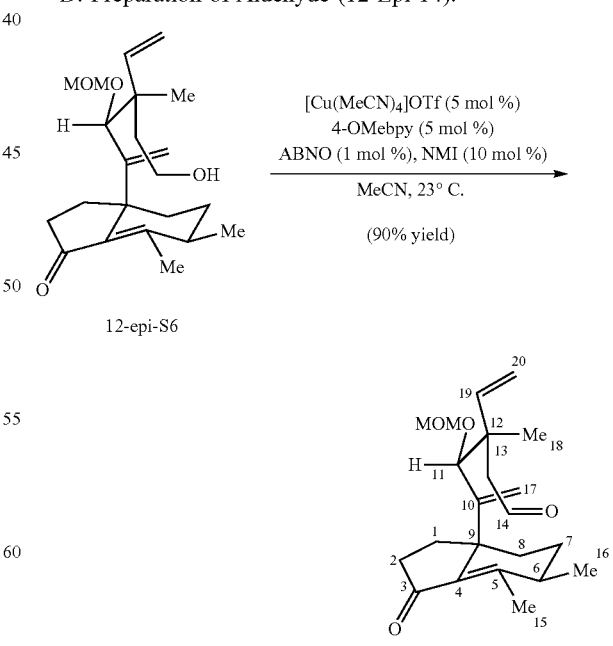

12-epi-S6

12-epi-14

A flame-dried, 250 mL round bottom flask equipped with a stir bar was charged with MOM ether 12-epi-S5 (332 mg, A flame-dried, 2 dram vial equipped with a stir bar was charged with alcohol 12-epi-S6 (164 mg, 0.452 mmol, 1 equiv) and MeCN (2.0 mL). Thereafter, added 860 µL of the [Cu]/bpy stock solution, 860 µL of the NMI stock solution, and 860 µL of the ABNO stock solution, in that order. The orange reaction was stirred at 960 rpm open to the atmosphere for 90 min. Subsequently, the resulting light blue solution was diluted with Et$_2$O (3 mL), passed through a short pad of SiO$_2$ using Et$_2$O as the eluent, and concentrated under reduced pressure to afford a pale yellow oil.

Purification was achieved via flash column chromatography on SiO$_2$ [8 g SiO$_2$, Et$_2$O/hexanes=30%→60%] to afford aldehyde 12-epi-14 (148 mg, 0.411 mmol, 90% yield) as a viscous, colorless oil that solidified to a white solid upon standing in the freezer.

TLC (70% Et$_2$O/hexanes): R$_f$=0.57 (UV, p-anisaldehyde).

$^1$H NMR (400 MHz, CDCl$_3$): δ 9.73 (dd, J=4.1, 1.8 Hz, 1H, C14), 6.08 (dd, J=17.7, 10.9 Hz, 1H, C19), 5.51 (s, 1H, C17), 5.16 (dd, J=10.9, 0.7 Hz, 1H, C20), 5.10 (dd, J=17.7, 0.7 Hz, 1H, C20), 4.99-4.97 (m, 1H, C17), 4.58 (d, J=6.9 Hz, 1H, OCH2OCH3), 4.51 (d, J=6.9 Hz, 1H, OCH2OCH3), 4.00 (d, J=1.2 Hz, 1H, C11), 3.40 (s, 3H, OCH2OCH3), 2.66 (dd, J=15.1, 4.1 Hz, 1H, C13), 2.49 (dd, J=15.1, 1.7 Hz, 1H, C13), 2.29-2.05 (m, 8H, C1, C2, C6, C8, C15), 1.68-1.49 (m, 2H, C1, C7), 1.32 (s, 3H, C18), 1.30-1.21 (m, 2H, C7, C8), 1.06 (d, J=7.1 Hz, 3H, C16).

$^{13}$C NMR (101 MHz, CDCl$_3$): δ 207.8 (C14=O), 202.6 (C3=O), 141.8 (C5), 122.0 (C10), 114.8 (C19), 95.3 (OCH2OCH3), 80.4 (C11), 56.5 (OCH2OCH3), 50.7 (C9), 50.2 (C13), 45.7 (C12), 37.6 (C6), 35.9 (C2), 33.4 (C8), 32.5 (C1), 28.1 (C7), 21.8 (C18), 19.1 (C16), 17.1 (C15).

FTIR (thin film, NaCl): 2932, 1714, 1628, 1456, 1413, 1373, 1212, 1151, 1035, 921 cm$^{-1}$.

HRMS (TOF, ES+): calc'd for C$_{22}$H$_{32}$O$_4$Na [M+Na]$^+$ 383.2198, found 383.2182.

[α]$_D^{23}$: −67.3° (c=0.095, CHCl$_3$).

E. Preparation of Tricycle (12-Epi-17)

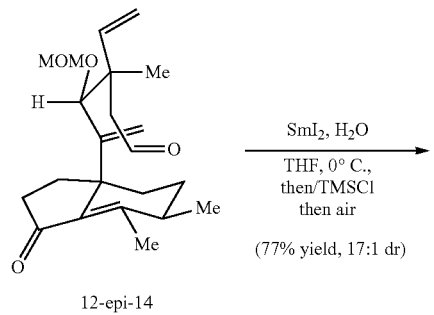

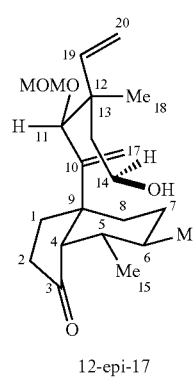

12-epi-17

A 25 mL Schlenk tube equipped with a stir bar was charged with a solution of aldehyde 12-epi-14 (75 mg, 0.208 mmol, 1 equiv) in 10.3 mL of THF that had been submitted to five freeze-pump-thaw cycles and H$_2$O/THF (1.88 mL).

The solution was cooled to 0° C. and stirred at this temperature for 5 min. Thereafter, SmI$_2$/THF (6.3 mL, 0.63 mmol, 3 equiv) was added dropwise over 8 min. The deep blue color of SmI$_2$ was immediately quenched upon addition of each drop. The first drop afforded a yellow solution, fading to a pale yellow and almost clear by the time 1.6 equiv SmI$_2$ had been added. When 2.2 equiv SmI$_2$ had been added, the blue color became increasingly persistent and upon addition of 2.6 equiv SmI$_2$, the reaction was dark blue/green. After stirring an additional 10 min at 0° C., TMSCl/THF (1.9 mL, 1.05 mmol, 5 equiv TMSCl) was added dropwise over 2 min, and the reaction was stirred an additional 10 min. Throughout this time, the deep blue color was quenched to yellow. Thereafter, the reaction was removed from the ice bath and stirred open to the atmosphere for 5 min.

The resulting pale yellow solution was diluted with Et$_2$O (50 mL), and washed with H$_2$O (2×10 mL). The aqueous layer was back-extracted with Et$_2$O (2×10 mL), and the combined organic layers were dried over Na$_2$SO$_4$, filtered, and concentrated under reduced pressure to afford a dark orange oil. Purification was achieved via flash column chromatography on SiO$_2$ [10 g SiO$_2$, Et$_2$O/hexanes=30%] to afford tricycle 12-epi-17 (62 mg, 0.172 mmol, 77% yield) as a white solid.

Stock solution of H$_2$O/THF: A solution of H$_2$O (60 µL) in THF (5.0 mL) was submitted to five freeze-pump-thaw cycles.

TLC (50% Et$_2$O/hexanes): R$_f$=0.50 (p-anisaldehyde).

$^1$H NMR (400 MHz, CDCl$_3$): δ 5.98 (dd, J=17.5, 10.8 Hz, 1H, C19), 5.42 (d, J=0.9 Hz, 1H, C17), 5.32 (t, J=0.7 Hz, 1H, C17), 5.09 (dd, J=17.5, 1.0 Hz, 1H, C20), 5.03 (dd, J=10.8, 1.0 Hz, 1H, C20), 4.54 (d, J=7.1 Hz, 1H, OCH2OCH3), 4.34 (dd, J=7.1, 0.5 Hz, 1H, OCH2OCH3), 4.12 (d, J=6.2 Hz, 1H, C14), 4.00 (s, 1H, C11), 3.34 (s, 3H, OCH2OCH3), 2.39-2.16 (m, 3H, C2, C4), 2.13-1.96 (m, 3H, C1, C8, C13), 1.72 (dtt, J=15.9, 6.2, 2.9 Hz, 1H, C6), 1.63 (dd, J=13.1, 3.3 Hz, 1H, C7), 1.46-1.37 (m, 1H, C7), 1.29 (s, 4H, C1, C15), 1.24 (d, J=0.8 Hz, 3H, C18), 1.08 (dd, J=15.8, 1.2 Hz, 1H, C8), 0.98 (d, J=6.8 Hz, 3H, C16).

$^{13}$C NMR (101 MHz, CDCl$_3$): δ 216.6 (C3=O), 148.1 (C19), 147.9 (C10), 112.8 (C17), 111.3 (C20), 92.3 (OCH2OCH3), 76.2 (C11), 67.0 (C14), 59.5 (C4), 55.9 (OCH2OCH3), 46.5 (C9), 45.7 (C8), 43.6 (C12), 42.1 (C5), 37.4 (C6), 34.9 (C2), 31.2 (C13), 29.8 (C1), 26.8 (C7), 18.2 (C16), 15.1 (C18), 13.4 (C15).

FTIR (thin film, NaCl): 3521, 2937, 1738, 1456, 1376, 1147, 1095, 1032, 967 cm$^{-1}$.

HRMS (FAB+) calc'd for C$_{22}$H$_{35}$O$_4$ [M+H]$^+$ 363.2535, found 363.2556.

[α]$_D^{23}$: +161.6° (c=0.09, CHCl$_3$).

F. Preparation of Silyl Enol Ether (12-Epi-18):

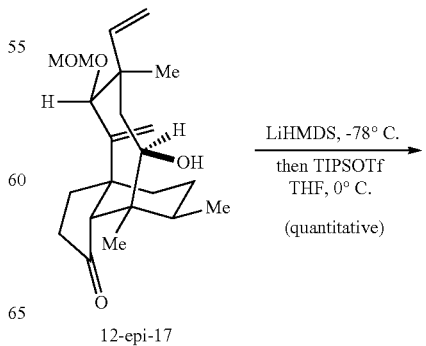

12-epi-17

91
-continued

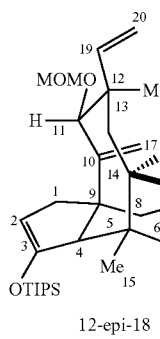

12-epi-18

A flame-dried 1 dram vial equipped with a stir bar was charged with tricycle 12-epi-17 (13.1 mg, 0.036 mmol, 1 equiv) and anhydrous THF (720 μL) under an atmosphere of argon. The mixture was cooled to −78° C. and stirred for 5 min prior to dropwise addition of LiHMDS in THF (108 μL of a 1.0 M solution, 0.108 mmol, 3 equiv) over 5 min. The resulting yellow solution was stirred at −78° C. for 5 min and was then placed in an ice bath and stirred for 5 min. Subsequently, TIPSOTf (22 μL, 0.072 mmol, 2 equiv) was added rapidly. After 3 min, the reaction was quenched at 0° C. via rapid addition of sat. aq. NaHCO$_3$ (1 mL) and vigorously stirred at 0° C. for 10 min. Thereafter, the mixture was extracted into Et$_2$O (3×1 mL) and the combined organic layers were washed with sat. aq. NaHCO$_3$ (3×1 mL) (note: failure to quench residual TIPSOTf in this manner resulted in extensive decomposition of product upon concentration). The combined organic layers were dried over Na$_2$SO$_4$, filtered, and concentrated under reduced pressure to afford a pale yellow oil.

Purification was achieved via flash column chromatography on SiO$_2$ [3 g SiO$_2$, Et$_2$O/hexanes=8%] to afford silyl enol ether 12-epi-18 (19.1 mg, 0.036 mmol, quantitative yield) as a puffy, viscous, colorless oil that formed a white solid upon standing in the freezer overnight.

TLC (30% Et$_2$O/hexanes): R$_f$=0.56 (p-anisaldehyde).

$^1$H NMR (400 MHz, CDCl$_3$): δ 6.02 (dd, J=17.5, 10.8 Hz, 1H, C19), 5.39 (s, 1H, C17), 5.23 (s, 1H, C17), 5.09 (dd, J=17.5, 1.1 Hz, 1H, C20), 5.01 (dd, J=10.8, 1.1 Hz, 1H, C20), 4.50 (d, J=6.9 Hz, 1H, OCH2OCH3), 4.42 (q, J=2.8 Hz, 2H, C2), 4.33 (d, J=6.9 Hz, 1H, OCH2OCH3), 4.24-4.15 (m, 2H, C11, C14), 3.33 (s, 3H, OCH2OCH3), 2.81 (s, 1H, C4), 2.33 (ddd, J=14.2, 3.2, 1.7 Hz, 1H, C1), 2.21-1.95 (m, 3H, C8, C13), 1.77 (ddq, J=14.3, 7.1, 3.8 Hz, 1H, C6), 1.65-1.53 (m, 1H, C7), 1.45-1.32 (m, 2H, C1, C7), 1.32-1.18 (m, 6H, C18, OSi(CH(CH3)2)3), 1.15 (s, 3H, C15), 1.12 (dd, J=7.2, 5.1 Hz, 18H, OSi(CH(CH3)2)3), 1.04-0.95 (m, 4H, C13, C16).

$^{13}$C NMR (101 MHz, CDCl$_3$) δ 157.5 (C3), 149.5 (C10), 148.6 (C19), 112.0 (C17), 110.9 (C20), 98.6 (C2), 92.7 (OCH2OCH3), 77.2 (C11), 67.7 (C14), 55.9 (OCH2OCH3), 53.2 (C4), 48.9 (C9), 46.3 (C13), 43.8 (C12), 41.3 (C5), 40.9 (C1), 38.4 (C6), 30.1 (C8), 27.2 (C7), 18.3 (C16), 18.1 (OSi(CH(CH3)2)3), 17.7 (OSi(CH(CH3)2)3), 15.6 (C18), 15.3 (C15), 12.9 (OSi(CH(CH3)2)3).

FTIR (thin film, NaCl): 2928, 1636, 1465, 1298, 1140, 1026, 906, 689 cm$^{-1}$.

HRMS (FAB+) calc'd for C$_{31}$H$_{54}$O$_4$Si [M+H]$^+$ 518.3791, found 518.3798.

[α]$_D^{23}$: +31.1° (c=0.15, CHCl$_3$).

92
G. Preparation of Ketone (12-Epi-19):

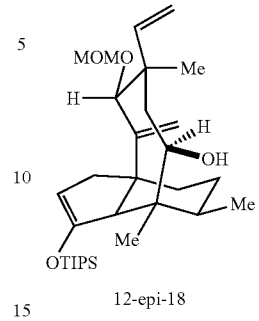

12-epi-18

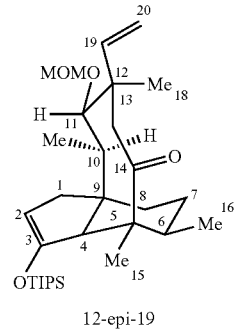

12-epi-19

This procedure was adapted from the work of Shenvi described above. To a 1 dram vial was added TIPS enol ether 12-epi-18 (25.6 mg, 0.049 mmol, 1 equiv) and adventitious water was removed via azeotropic drying with PhH (3×1 mL) under high vacuum (70 mTorr). An oven dried stir bar was added, and the atmosphere was exchanged three times with argon. Thereafter, 775 μL of a stock solution containing PhSiH$_3$ (9.3 μL, 0.075 mmol, 1.5 equiv) and TBHP (20 μL, 0.100 mmol, 2 equiv) in iPrOH was added, followed by 175 μL of a stock solution containing Mn(dpm)$_3$ (3.0 mg, 0.00506 mmol, 0.1 equiv) in iPrOH. The reaction was stirred for 30 min at ambient temperature and another 50 μL of the Mn(dpm)$_3$ (0.9 mg, 0.00144 mmol, 0.03 equiv) was added. After 1 h, the reaction was passed through a plug of SiO$_2$ (eluting with Et$_2$O/hexanes=10%), and concentrated under reduced pressure to afford a dark orange oil.

Purification was achieved via flash column chromatography on SiO$_2$ [3 g SiO$_2$, Et$_2$O/hexanes=7%→11%] to afford ketone 12-epi-19 (13.7 mg, 0.0251 mmol, 54% yield) as a viscous, colorless oil.

This reaction exhibits a pronounced sensitivity to both residual oxygen and water. In addition, we found it critical to perform this reaction at 23° C., as higher temperatures promoted over-reduction and lower temperatures slowed catalysis. iPrOH was stored over activated 4 Å molecular sieves (pellets) overnight then was distilled from CaH$_2$ (10% w/v) in a flame-dried, argon-filled apparatus immediately prior to use.

Preparation of stock solutions: PhSiH$_3$ (30 μL) and tert-butyl hydroperoxide (65 μL of a 5.0 M solution in nonane) were dissolved in iPrOH (2.5 mL) and the homogeneous solution was submitted to three freeze-pump-thaw cycles. Mn(dpm)$_3$ (17.3 mg) was dissolved in 1 mL iPrOH and the dark brown homogeneous solution was submitted to three freeze-pump-thaw cycles.

TLC (30% Et$_2$O/hexanes): R$_f$=0.72 (p-anisaldehyde).

$^1$H NMR (400 MHz, CDCl$_3$): δ 5.96 (dd, J=17.4, 10.7 Hz, 1H, C19), 5.09-4.97 (m, 2H, C20), 4.55 (d, J=7.0 Hz, 1H,

OCH2OCH3), 4.53 (d, J=7.0 Hz, 1H, OCH2OCH3), 4.44 (s, 1H, C2), 3.81 (d, J=5.8 Hz, 1H, C11), 3.37 (s, 3H, OCH2OCH3), 3.22 (s, 1H, C4), 2.92 (d, J=12.0 Hz, 1H, C13), 2.15 (ddd, J=14.1, 3.2, 1.6 Hz, 1H, C1), 1.95-1.66 (m, 4H, C7, C8, C10, C13), 1.66-1.50 (m, 3H, C1, C6, C7), 1.34 (s, 3H, C15), 1.27-1.22 (m, 4H, C8, OSi(CH(CH3)2)3), 1.19 (s, 3H, C18), 1.17 (d, J=7.0 Hz, 3H, C16), 1.13 (d, J=2.9 Hz, 9H, OSi(CH(CH3)2)3), 1.11 (d, J=2.9 Hz, 9H, OSi(CH(CH3)2)3).

$^{13}$C NMR (101 MHz, CDCl$_3$): δ 214.4 (C14=O), 156.8 (C3), 147.7 (C19), 111.4 (C20), 98.6 (C2), 98.1 (OCH2OCH3), 81.5 (C11), 56.6 (OCH2OCH3), 51.5 (C4), 50.6 (C5), 48.1 (C9), 47.9 (C12), 46.6 (C13), 37.2 (C6), 34.5 (C1), 34.4 (C10), 32.0 (C7), 26.7 (C8), 23.2 (C15), 18.1 (OSi(CH(CH3)2)3), 16.2 (C16), 15.0 (C18), 12.9 (OSi(CH(CH3)2)3), 12.0 (C17).

FTIR (thin film, NaCl): 2946, 2868, 1698, 1634, 1463, 1300, 1129, 1086, 882, 692 cm$^{-1}$.

HRMS (FAB+): calc'd for C$_{31}$H$_{54}$O$_4$Si [M]$^+$ 518.3791, found 518.3797.

$[α]_D^{23}$: −18.5° (c=0.195, CHCl$_3$).

H. Preparation of Alcohol (12-Epi-20)

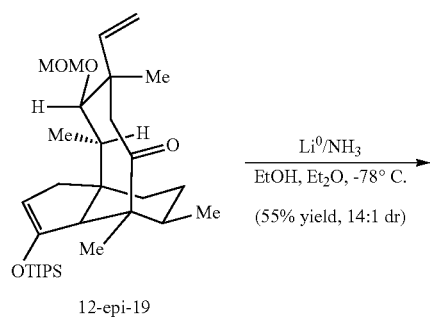

12-epi-19

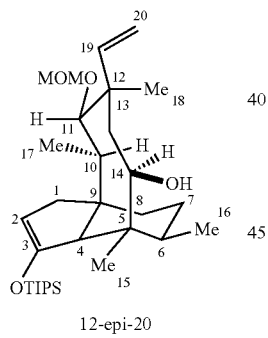

12-epi-20

A 100 mL 3-necked flask equipped with a stir bar was equipped with a cold finger connected to a two-way valve, and the entire apparatus was flame-dried under high vacuum. After cooling to ambient temperature, the atmosphere was exchanged three times for argon, and anhydrous EtOH (7.3 mL) and Et$_2$O (4 mL) were added. The mixture was cooled to −78° C., and ammonia (30 mL) was condensed into the vessel. Subsequently, a solution of ketone 12-epi-19 (23 mg, 0.0443 mmol, 1 equiv) in Et$_2$O (5.3 mL) was added. After allowing the system to equilibrate for 5 min, Li$^0$ wire (69 mg, 9.9 mmol, 223 equiv) that had been freshly washed with hexanes and cut into ~10 mg pieces was added. Within 3 min, a deep blue color developed, and after 30 min, the reaction was colorless.

The apparatus was removed from the cooling bath, and ammonia was boiled off over 1 h. The resulting slurry was extracted into Et$_2$O (50 mL), washed with sat. aq. NaHCO$_3$ (10 mL), dried over Na$_2$SO$_4$, filtered, and concentrated under reduced pressure to afford an oil.

Purification was achieved via flash column chromatography on SiO$_2$ [3 g SiO$_2$, H$_2$O/hexanes=7%] to afford alcohol 12-epi-20 (12.7 mg, 0.0244 mmol, 55% yield) as a viscous, colorless oil.

TLC (15% Et$_2$O/hexanes): R$_f$=0.36 (p-anisaldehyde).

$^1$H NMR (400 MHz, CDCl$_3$): δ 5.76 (dd, J=17.6, 10.8 Hz, 1H, C19), 4.97 (dd, J=17.6, 1.2 Hz, 1H, C20), 4.90 (dd, J=10.8, 1.2 Hz, 1H, C20), 4.50 (d, J=6.9 Hz, 1H, OCH2OCH3), 4.47 (d, J=6.8 Hz, 1H, OCH2OCH3), 4.20 (t, J=7.5, 6.7 Hz, 1H, C14), 3.35 (s, 3H, OCH2OCH3), 3.08 (d, J=5.6 Hz, 1H, C11), 2.47-2.28 (m, 2H, C2), 2.22-2.07 (m, 2H, C10, C13), 1.98 (d, J=15.3 Hz, 2H, C1, C7), 1.40 (m, 5H, C6, C7, C15), 1.26-1.08 (m, 27H, C1, C8, C13, C18, OSi(CH(CH3)2)3), 1.01 (d, J=6.6 Hz, 3H, C16), 0.84 (d, J=7.2 Hz, 3H, C17).

$^{13}$C NMR (101 MHz, CDCl$_3$): δ 149.1 (C19), 147.2 (C3), 120.3 (C4), 110.5 (C20), 99.0 (OCH2OCH3), 83.5 (C11), 68.2 (C14), 56.5 (OCH2OCH3), 50.6 (C9), 47.1 (C13), 46.2 (C5), 44.9 (C12), 43.2 (C6), 39.4 (C1), 36.3 (C10), 34.4 (C2), 28.4 (C7), 28.3 (C8), 18.33 (C15), 18.26 (OSi(CH(CH3)2)3), 18.2 (OSi(CH(CH3)2)3), 17.8 (C16) 14.4 (C18), 13.8 (OSi(CH(CH3)2)3), 11.4 (C17).

FTIR (thin film, NaCl): 2921, 2866, 1635, 1463, 1328, 1218, 1030, 1002, 913, 797 cm$^{-1}$.

HRMS (FAB+): calc'd for C$_{31}$H$_{56}$O$_4$Si [M]$^+$ 520.3948, found 520.3932.

$[α]_D^{23}$: −46.3° (c=0.14, CHCl$_3$).

I. Preparation of (+)-12-Epi-Pleuromutilin (12-Epi-1):

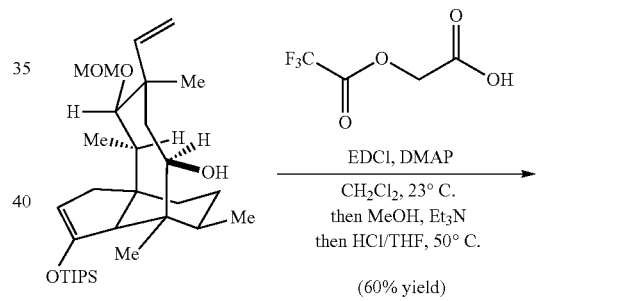

(+)-12-epi-pleuromutilin (12-epi-1)

This procedure was adapted from the work of Procter described above. A flame-dried 2 dram vial equipped with a stir bar was charged with alcohol 12-epi-20 (12.7 mg, 0.0244 mmol, 1 equiv), EDCI.HCl (28.0 mg, 0.146 mmol, 6 equiv), and DMAP (17.8 mg, 0.146 mmol, 6 equiv), and the atmosphere was exchanged three times for argon. Subsequently, the vessel was charged with anhydrous CH$_2$Cl$_2$ (1.2 mL) and 2-(2,2,2-trifluoroacetoxy)acetic acid (25.0 mg, 0.146 mmol, 6 equiv), and the reaction was stirred at ambient temperature. After 10 min, a light yellow color developed, and after 30 min, the reaction was complete by TLC analysis (30% Et$_2$O/hexanes, R$_f$=0.77 [p-anisaldehyde], R$_f$ (starting material)=0.70). Thereafter, a solution of anhydrous MeOH (19 μL, 0.480 mmol, 20 equiv) in freshly distilled Et$_3$N (67 μL, 0.480 mmol, 20 equiv) was added, and the reaction immediately turned bright yellow. After 5 min, the reaction was judged was complete by TLC analysis (30% Et$_2$O/hexanes, R$_f$=0.35 [p-anisaldehyde]). A solution of HCl in THF (600 μL of a 2.0 M solution, 1.2 mmol) was added, and the reaction was heated to 50° C. After 30 min, an additional portion of HCl in THF (260 μL) was added. At this time, hydrolysis of the methoxymethyl group was judged complete by TLC analysis (70% Et$_2$O/hexanes, R$_f$=0.42 [p-anisaldehyde]), and after 2 h global hydrolysis was complete. The reaction was cooled to 0° C. and was cautiously quenched with sat. aq. NaHCO$_3$ (3 mL). After warming to ambient temperature, the crude mixture was extracted into Et$_2$O (3×5 mL), dried over Na$_2$SO$_4$, filtered, and concentrated under reduced pressure to afford an orange oil.

Purification was achieved via flash column chromatography on SiO$_2$ [1.5 g Et$_2$O/hexanes=50%→70%] to afford (+)-12-epi-pleuromutilin 12-epi-1 (5.4 mg, 0.0143 mmol, 60% yield) as a white solid.

TLC (70% Et$_2$O/hexanes): R$_f$=0.26 (p-anisaldehyde).

$^1$H NMR (400 MHz, CDCl$_3$): δ 5.81-5.65 (m, 2H, C14, C19), 5.27-5.17 (m, 2H, C20), 4.07 (dd, J=17.1, 5.6 Hz, 1H, C22), 4.01 (dd, J=17.1, 5.2 Hz, 1H, C22), 3.45 (d, J=6.4 Hz, 1H, C11), 2.45-2.00 (m, 6H, C2, C4, C10, C13, C22OH,), 1.81 (dq, J=13.9, 2.7 Hz, 1H, C8), 1.73-1.58 (m, 2H, C1, C6), 1.58-1.45 (m, 3H, C1, C7, C11OH), 1.44 (s, 3H, C15), 1.42-1.36 (m, 1H, C7), 1.25 (s, 3H, C18), 1.18-1.04 (m, 2H, C8, C13), 0.97 (d, J=7.1 Hz, 3H, C17), 0.70 (d, J=7.0 Hz, 3H, C16).

$^{13}$C NMR (101 MHz, CDCl$_3$): δ 217.0 (C3=O), 172.1 (C21), 146.8 (C19), 115.4 (C20), 71.9 (C11), 70.1 (C14), 61.3 (C22), 58.2 (C4), 45.4 (C9), 45.3 (C12), 43.6 (C13), 41.8 (C5), 36.6 (C6), 34.5 (C2), 34.4 (C10), 30.1 (C8), 26.9 (C7), 25.0 (C1), 16.7 (C16), 14.8 (C15), 14.1 (C18), 10.8 (C17).

FTIR (thin film, NaCl): 3437, 2927, 1728, 1603, 1444, 1382, 1232, 1098, 1011, 755 cm$^{-1}$.

HRMS (FAB+): calc'd for C$_{22}$H$_{33}$O$_5$ [M±H]$^+$−H$_2$ 377.2328, found 377.2329.

[α]$_D^{23}$: +9.12° (c=0.125, CHCl$_3$).

Example 4: Synthesis of Allylboronic Acid (Z-6)

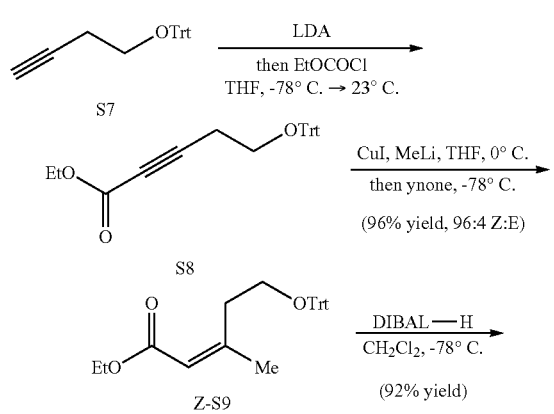

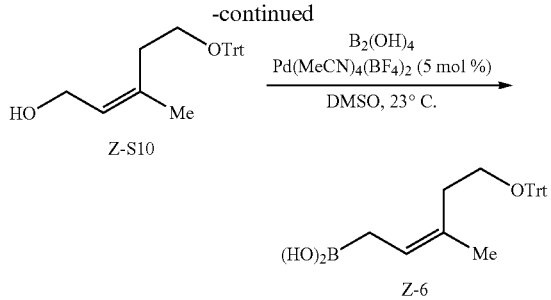

A. Preparation of trityl protected alcohol (S7):

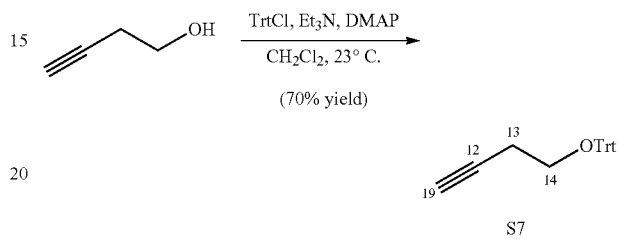

A flame-dried, 250 mL round bottom flask equipped with a stir bar was charged with 3-butyn-1-ol (7.01 g, 100.0 mmol, 7.57 mL, 1 equiv), CH$_2$Cl$_2$ (150 mL, 0.67 M), and DMAP (2.44 g, 20.0 mmol, 20 mol %). To the homogeneous solution was added Et$_3$N (20.2 g, 200.0 mmol, 27.9 mL, 2 equiv) and trityl chloride (27.8 g, 100.0 mmol, 1 equiv). The reaction was stirred at ambient temperature for 18 h. Subsequently, added H$_2$O (225 mL) and extracted into Et$_2$O (3×200 mL). The combined organic layers were washed with brine (2×50 mL), dried over Na$_2$SO$_4$, and concentrated under reduced pressure to afford a white solid.

The solid was dissolved in a minimal volume of CH$_2$Cl$_2$ (30 mL) and purified via flash column chromatography on SiO$_2$ (300 g SiO$_2$, Et$_2$O/hexanes=5%) to afford product S7 (21.9 g, 70.1 mmol, 70% yield) as a white solid. Spectral data were in complete agreement with literature values. See, Mulzer, *J. Org. Chem.* 2004, 69, 891-898.

TLC (20% Et$_2$O/hexanes): R$_f$=0.73 (UV, KMnO$_4$).

B. Preparation of Ynoate (S8):

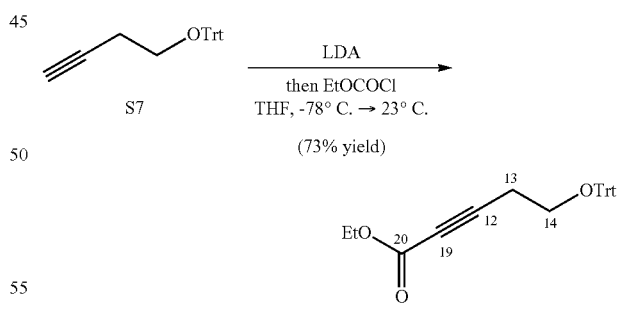

The atmosphere of a flame-dried, 1 L round bottom flask equipped with a stir bar was exchanged three times for nitrogen then charged with anhydrous THF (180 mL) and freshly distilled diisopropylamine (9.58 g, 94.6 mmol, 13.3 mL, 1.35 equiv). The mixture was cooled to −78° C. and nBuLi (35.9 mL of a 2.46 M solution, 88.3 mmol, 1.26 equiv) was added slowly over 15 min. The solution was stirred at −78° C. for 5 min, warmed to 0° C., stirred 10 min, then cooled back to −78° C. Thereafter, a solution of the tritylprotected substrate S7 (21.9 g, 70.1 mmol, 1 equiv) in anhydrous THF (70 mL) was added dropwise over 30 min, and the reaction was stirred for an additional 15 min. Ethyl chloroformate (22.8 g, 210.3 mmol, 20.1 mL, 3 equiv) was then added over 15 min, and the reaction was stirred for an additional 10 min before being warmed to ambient temperature and stirred for 3 h.

The reaction was quenched via addition of saturated aq. NH$_4$Cl (150 mL) and stirred for 10 min. Thereafter, H$_2$O (150 ml) was added, the reaction was extracted into Et$_2$O (2×150 mL), the combined organic layers were dried over Na$_2$SO$_4$, and concentrated under reduced pressure to afford a pale yellow solid. The crude residue was suspended in hexanes (80 mL), heated to a boil, additional hexanes (100 mL) was added, and the heterogeneous suspension was filtered while hot to remove residual ammonium salts. The mixture was re-heated and slowly cooled overnight to afford product S8 (19.6 g, 51.0 mmol, 73% yield) as white crystals.

TLC (20% Et$_2$O/hexanes): R$_f$=0.52 (UV).

$^1$H NMR (400 MHz, CDCl$_3$): δ 7.52-7.42 (m, 6H, Ph$_3$CO), 7.34-7.20 (m, 9H, Ph$_3$CO), 4.25 (q, J=7.2 Hz, 2H, OCH2CH3), 3.31 (t, J=6.9 Hz, 2H, C14), 2.63 (t, J=6.9 Hz, 2H, C13), 1.34 (t, J=7.1 Hz, 3H, OCH2CH3).

$^{13}$C NMR (101 MHz, CDCl$_3$): δ 153.7 (C20=O), 143.7 (Ph$_3$CO), 128.6 (Ph$_3$CO), 127.9 (Ph$_3$CO), 127.1 (Ph$_3$CO), 86.9 (Ph$_3$CO), 86.5 (C12), 74.0 (C19), 61.9 (OCH2CH3), 61.1 (C14), 20.3 (C13), 14.1 (OCH2CH3).

FTIR (AT-IR): 2937, 2882, 2243, 1713, 1471, 1377, 1018 cm$^{-1}$.

HRMS (FAB+, m/z): calc'd for C$_{26}$H$_{24}$O$_3$ [M]$^+$ 384.1726, found 384.1739.

Melting point: 89.4-90.0° C.

C. Preparation of Acrylate (Z-S9):

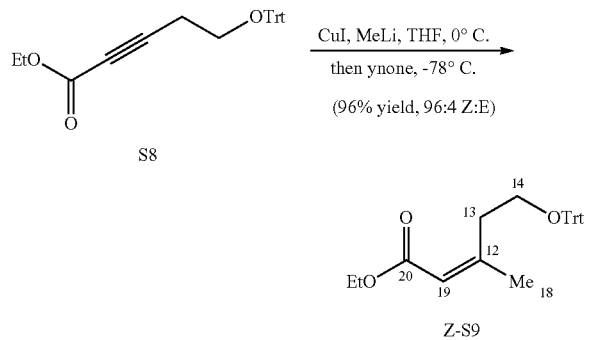

In a nitrogen-filled glovebox, a flame-dried 2 L flask equipped with a large stir bar was charged with CuI (9.68 g, 50.9 mmol, 1 equiv). Anhydrous THF (390 mL) was transferred to the flask via cannula, and the heterogeneous suspension was stirred at 0° C. for 20 min. Thereafter, MeLi (64.8 mL of a 1.57 M solution in Et$_2$O, 101.7 mmol, 2 equiv) was added dropwise over 25 min during which time the reaction went from a heterogeneous brown suspension to a nearly colorless, homogeneous solution. After an additional 5 min of stirring, the mixture was cooled to −78° C. and stirred for 20 min prior to dropwise addition of alkynoate ester S8 (19.6 g, 50.9 mmol, 1 equiv) in anhydrous THF (130 mL) via cannula over 20 min. The reaction was stirred at −78° C. for 2 h then quenched with H$_2$O (25 mL) at −78° C. After 10 min, the solution was warmed to ambient temperature, filtered through a pad of Celite, and the Celite was rinsed with Et$_2$O (3×75 mL). The combined organic layers were washed with H$_2$O (2×50 mL) and brine (1×50 mL), dried over Na$_2$SO$_4$, and concentrated under reduced pressure to afford acrylate Z-S9 (19.5 g, 48.7 mmol, 96% yield, 96:4 Z: E) as a viscous, yellow oil.

TLC (10% Et$_2$O/hexanes): R$_f$=0.55 (UV).

$^1$H NMR (400 MHz, CDCl$_3$): δ 7.48-7.41 (m, 6H, Ph$_3$CO), 7.32-7.19 (m, 9H, Ph$_3$CO), 5.74 (d, J=1.4 Hz, 1H, C19), 4.13 (q, J=7.1 Hz, 2H, OCH2CH3), 3.26 (t, J=6.4 Hz, 2H, C14), 2.97 (t, J=6.4 Hz, 2H, C13), 1.90 (d, J=1.4 Hz, 3H, C18), 1.26 (t, J=7.1 Hz, 3H, OCH2CH3).

$^{13}$C NMR (101 MHz, CDCl$_3$): δ 166.2 (C20=O), 157.9 (C12), 144.2 (Ph$_3$CO), 128.7 (Ph$_3$CO), 127.7 (Ph$_3$CO), 126.8 (Ph$_3$CO), 117.5 (C19), 86.6 (Ph$_3$CO), 62.4 (C14), 59.5 (OCH2CH3), 33.7 (C13), 26.1 (C18), 14.3 (OCH2CH3).

FTIR (AT-IR): 2982, 2915, 2873, 1709, 1652, 1489, 1447, 1265, 1194, 1146, 779 cm$^{-1}$.

HRMS (FAB+, m/z): calc'd for C$_{17}$H$_{27}$O$_3$ [(M+H)−H$_2$]$^+$ 399.1960, found 399.1958.

D. Preparation of (Z)-3-Methyl-5-(Trityloxy)Pent-2-En-1-Ol (Z-S10):

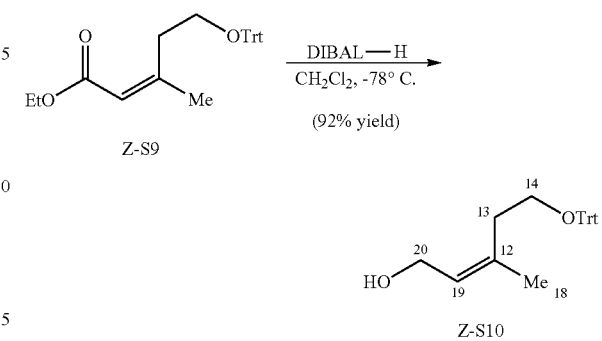

The atmosphere of a flame-dried, 1 L round bottom flask equipped with a stir bar was exchanged three times for argon then charged with acrylate Z-S9 (19.5 g, 48.7 mmol, 1 equiv) and anhydrous CH$_2$Cl$_2$ (162 mL) and cooled to −78° C. Subsequently, a freshly-prepared solution of DIBAL-H (20.8 g, 146.2 mmol, 26.1 mL) in anhydrous hexanes (122 mL) was added via cannula over 25 min. The resulting light yellow reaction was stirred at −78° C. for 2 h. The reaction was quenched at −78° C. via slow addition of H$_2$O (30 mL) followed by 2 M NaOH (30 mL), stirred 10 min at −78° C., and warmed to 0° C. Additional H$_2$O (30 mL) was added, and the suspension was transferred to a 1 L Erlenmeyer flask containing a large stir bar and cooled to 0° C. Subsequently, anhydrous MgSO$_4$ (100 g) was added slowly, and a strongly exothermic reaction was observed. After stirring vigorously for 20 min, the slurry was filtered through Celite, the Celite was washed with Et$_2$O (3×100 mL), and concentrated under reduced pressure to afford a viscous, pale yellow oil.

Purification was achieved via flash column chromatography on SiO$_2$ [300 g SiO$_2$, Et$_2$O/hexanes=30%→50%] to afford allylic alcohol Z-S10 (16.2 g, 45.2 mmol, 92% yield) as a viscous, colorless oil.

TLC (30% Et$_2$O/hexanes): R$_f$=0.30 (KMnO$_4$).

$^1$H NMR (400 MHz, CDCl$_3$): δ 7.48-7.41 (m, 6H, Ph$_3$CO), 7.32-7.19 (m, 9H, Ph$_3$CO), 5.59 (t, J=7.1 Hz, 1H, C19), 4.14 (d, J=7.1 Hz, 2H, C20), 3.20 (t, J=6.4 Hz, 2H, C14), 2.37 (t, J=6.4 Hz, 2H, C13), 1.66 (s, 3H, C18), 1.50 (br m, 1H, OH).

¹³C NMR (101 MHz, CDCl₃): δ 144.0 (Ph₃CO), 137.5 (C12), 128.7 (Ph₃CO), 127.8 (Ph₃CO), 127.0 (Ph₃CO), 126.1 (C19), 87.0 (Ph₃CO), 61.8 (C14), 58.9 (C20), 32.6 (C13), 23.7 (C18).

FTIR (AT-IR): 3361 (br), 3057, 2915, 2875, 1596, 1490, 1448, 1265, 1061, 1001 cm⁻¹.

HRMS (TOF, ES+): calc'd for $C_{25}H_{26}O_2Na$ [M+Na]⁺ 381.1831, found 381.1843.

E. Preparation of Trityl-Protected (Z)-Allylboronic Acid (Z-6):

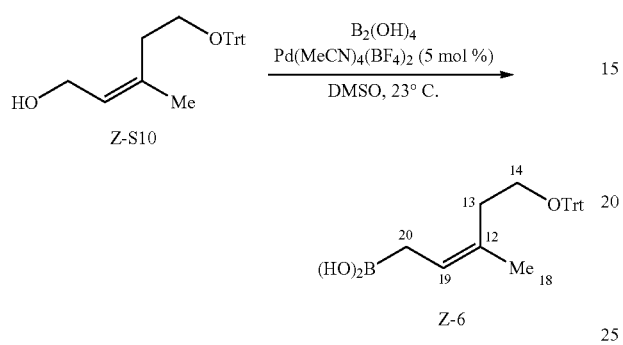

This procedure was adapted from the work of Szabó described above. In a nitrogen-filled glovebox, a flame dried, 100 mL round bottom flask equipped with a stir bar was charged with allylic alcohol Z-S10 (2.67 g, 7.45 mmol, 1 equiv) and anhydrous, degassed DMSO (18.6 mL, 0.4 M). The mixture was stirred until the viscous allylic alcohol dissolved, at which time Pd(MeCN)₄(BF₄)₂ (165 mg, 0.373 mmol, 5 mol %) was added followed by tetrahydroxydiboron (801 mg, 8.94 mmol, 1.2 equiv). The reaction was vigorously stirred and transformed from a dark orange/red solution to dark green to black within 2 min. After stirring for 90 min at ambient temperature, the black mixture was transferred via cannula to a 100 mL Schlenk flask, the atmosphere of which had been exchanged with argon three times. Degassed PhMe (37.0 mL) was added to the black mixture followed by degassed 16% aq.

NaCl (15 mL). The system was sealed off, shaken, and the layers were separated. The organic layer was washed with additional degassed 16% aq. NaCl (3×15 mL) to afford an organic solution with a black particulate suspension. The suspension was allowed to stand for 30 min, during which time the particulates settled. The top solution was transferred via cannula to a 100 mL Schlenk tube, the atmosphere of which had been exchanged with argon three times, and the tube was pumped into the glovebox where naphthalene was added as an internal standard. A ¹H NMR sample was prepared in the glovebox using dry, degassed CDCl₃, and it was determined that [allylboronic acid]=0.18 M. Allylboronic acid Z-6 was immediately used in the next reaction.

Example 5: Synthesis of Allylboronic Acid (E-6)

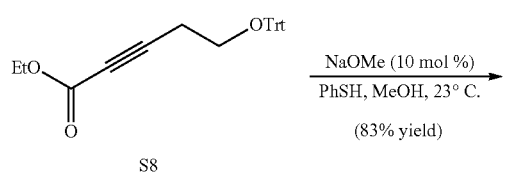

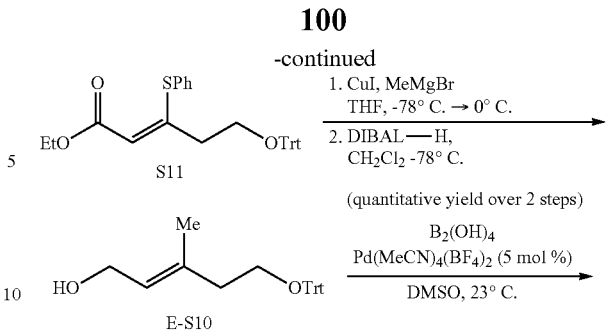

A. Preparation of Thiol Acrylate (S11):

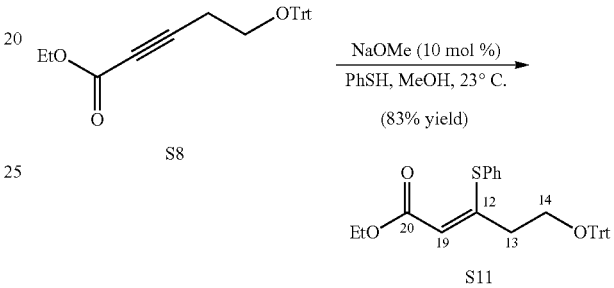

A flame-dried, 250 mL round bottom flask equipped with a stir bar was charged with alkynoate ester S8 (7.79 g, 20.2 mmol, 1 equiv) and freshly distilled MeOH (100 mL). Thereafter, thiophenol (2.3 mL, 22.2 mmol, 1.1 equiv) and a freshly prepared solution of NaOMe (0.1 M, 2.02 mL, 2.02 mmol, 0.1 equiv) were added. The solution was stirred under argon for 12 h or until TLC analysis indicated complete consumption of starting material. The reaction mixture was filtered over a pad of SiO₂ and concentrated under reduced pressure to afford a yellow oil.

Purification was achieved via flash column chromatography on SiO₂ [500 g SiO₂, Et₂O/hexanes=7% Et₂O/hexanes→10%] to afford thiol acrylate S11 (8.3 g, 16.8 mmol, 83% yield) as a white foamy solid.

TLC (40% Et₂O/hexanes): $R_f$=0.56 (UV, p-anisaldehyde).

¹H NMR (400 MHz, CDCl₃): δ 7.39-7.18 (m, 15H, OCPh3, SPh), 5.90 (d, J=0.8 Hz, 1H, C19), 4.21 (q, J=7.1 Hz, 2H, OCH2CH3), 3.00 (t, J=6.7 Hz, 2H, C14), 2.42 (t, J=6.7 Hz, 2H, C13), 1.31 (t, J=7.1 Hz, 3H, OCH2CH3).

¹³C NMR (101 MHz, CDCl₃): δ 166.1 (C20=O), 157.8 (C12), 143.8 (OCPh3), 135.7 (SPh), 130.5 (SPh), 129.2 (SPh), 129.1 (SPh), 128.6 (OCPh3), 127.8 (OCPh3), 126.9 (OCPh3), 113.7 (C19), 86.5 (OCPh3), 62.1 (C14), 60.0 (OCH2CH3), 36.9 (C13), 14.4 (OCH2CH3).

FTIR (AT-IR): 3057, 2975, 2871, 1699, 1590, 1448, 1209, 1115, 1059, 1031 cm⁻¹.

HRMS (TOF, ES+): calc'd for $C_{32}H_{30}O_3NaS$ [M+Na]⁺ 517.1813, found 517.1819.

B. Preparation of (E)-3-Methyl-5-(Trityloxy)Pent-2-En-1-Ol (E-S10):

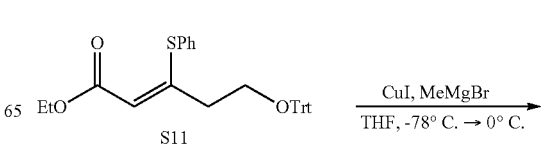

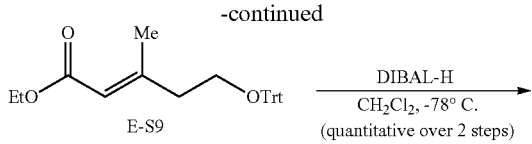

In a nitrogen-filled glovebox, a flame-dried, 500 mL round bottom flask equipped with a stir bar was charged with CuI (4.2 g, 21.8 mmol, 1.3 equiv). Anhydrous THF (168 mL) was added and the heterogeneous suspension was stirred at −78° C. for 10 min. Thereafter, MeMgBr (6.7 mL of a 3.0 M solution in Et₂O, 20.2 mmol, 1.2 equiv) was added dropwise. The reaction was warmed to 0° C. and stirred for 30 min. The solution was cooled back down to −78° C., where thiol acrylate S11 (8.3 g, 16.8 mmol) was added via cannula transfer in anhydrous THF (30 mL). The reaction was stirred for 1 h or until complete by TLC analysis. Upon completion, the reaction was quenched with H₂O (25 mL) at −78° C. and warmed to ambient temperature, and filtered through a pad of Celite. The Celite was rinsed with Et₂O until TLC analysis indicated there was no product remaining. The combined organic layers were washed with H₂O (2×50 mL) and brine (1×50 mL), dried over MgSO₄, and concentrated under reduced pressure to afford product as a viscous, yellow oil. The crude material was subjected to the next reaction without further purification. A representative spectrum of the crude mixture as used in the next step is provided.

TLC (20% Et₂O/hexanes): $R_f$=0.60 (UV, p-anisaldehyde).

A flame-dried, 250 mL round bottom flask equipped with a stir bar was charged with crude acrylate E-59 (16.8 mmol, 1 equiv). Thereafter, anhydrous CH₂Cl₂ (56 mL) was added and the solution was cooled to −78° C. A freshly prepared solution of DIBAL-H in hexanes (12 mL of a 1.2 M solution in hexanes, 67.2 mmol, 4 equiv) was added via cannula transfer. The reaction was stirred at −78° C. for 40 min. The solution was slowly quenched with sat. aq. Rochelle's salt (50 mL) and stirred overnight or until two clear layers formed. The aqueous layer was extracted with CH₂Cl₂ (3×30 mL). The combined organic layers were washed with brine (50 mL) and dried over MgSO₄. The suspension was filtered and concentrated under reduced pressure to afford a pale yellow oil.

Purification was achieved via flash column chromatography on SiO₂ [125 g SiO₂, 30% Et₂O/hexanes→60%] to afford allylic alcohol E-S10 (6.02 g, 16.8 mmol, quantitative yield over 2 steps) as a clear viscous oil.

TLC (60% Et₂O/hexanes): $R_f$=0.42 (UV, p-anisaldehyde).

¹H NMR (400 MHz, CDCl₃): δ 7.40 (dt, J=8.6, 1.9 Hz, 6H, OCPh3), 7.31-7.09 (m, 9H, OCPh3), 5.41 (td, J=6.9, 1.3 Hz, 1H, C19), 4.10 (d, J=7.0 Hz, 2H, C20), 3.13 (t, J=6.8 Hz, 2H, C14), 2.30 (t, J=6.8 Hz, 2H, C13), 1.59 (s, 3H), 1.16 (s, 1H, OH).

¹³C NMR (101 MHz, CDCl₃): δ 144.3 (OCPh3), 137.1 (C12), 128.6 (OCPh3), 127.7 (OCPh3), 126.9 (OCPh3), 125.1 (C19), 86.5 (OCPh3), 62.3 (C14), 59.3 (C20), 39.9 (C13), 16.6 (C18).

FTIR (AT-IR): 3321, 3057, 2871, 1596, 1448, 1218, 1061, 1031, 1001, 704 cm⁻¹

HRMS (TOF, ES+): calc'd for C₂₅H₂₆O₂Na [M+Na]⁺ 381.1831, found 381.1826.

C. Preparation of Trityl-Protected (E)-Allylboronic Acid (E-6):

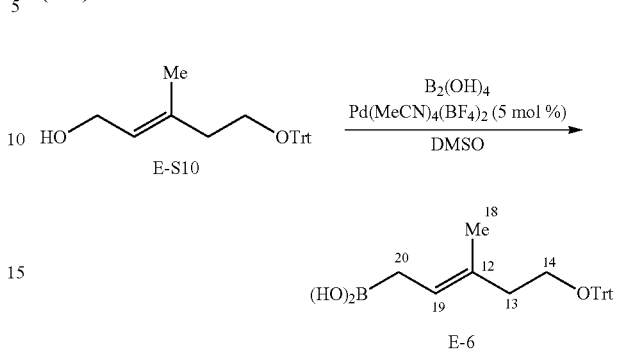

This procedure was adapted from the work of Szabó described above. In a nitrogen-filled glovebox, a flame dried, 25 mL round bottom flask equipped with a stir bar was charged with allylic alcohol E-S10 (896 mg, 2.5 mmol, 1 equiv) and anhydrous, degassed DMSO (6.25 mL). The mixture was stirred until the viscous allyl alcohol dissolved, at which time Pd(MeCN)₄(BF₄)₂ (55.5 mg, 0.125 mmol, 5 mol %) was added followed by tetrahydroxydiboron (269 mg, 3.00 mmol, 1.2 equiv). The reaction was vigorously stirred and transformed from a dark orange/red solution to dark green to black within 2 min. After stirring for 90 min at ambient temperature, the black mixture was transferred via cannula to a 25 mL Schlenk flask, the atmosphere of which had been exchanged with argon three times. Degassed PhMe (12.3 mL) was added to the black mixture followed by degassed 16% aq. NaCl (5 mL). The system was sealed off, shaken, and the layers were separated. The organic layer was washed with additional degassed 16% aq. NaCl (3×5 mL) to afford an organic solution with a black particulate suspension. The suspension was allowed to stand for 30 min, during which time the particulates settled. The top solution was transferred via cannula to a 50 mL Schlenk tube, the atmosphere of which had been exchanged with argon three times, and the tube was pumped into the glovebox where naphthalene was added as an internal standard. A ¹H NMR sample was prepared in the glovebox using dry, degassed CDCl₃, and it was determined that [allylboronic acid]=0.15 M. Allylboronic acid E-6 was immediately used in the next reaction.

Example 6: Transannular [1,5]-HAT Deuterium-Labeling Studies

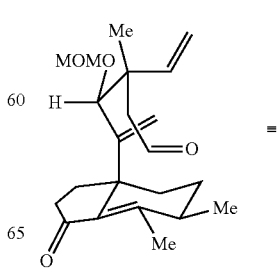

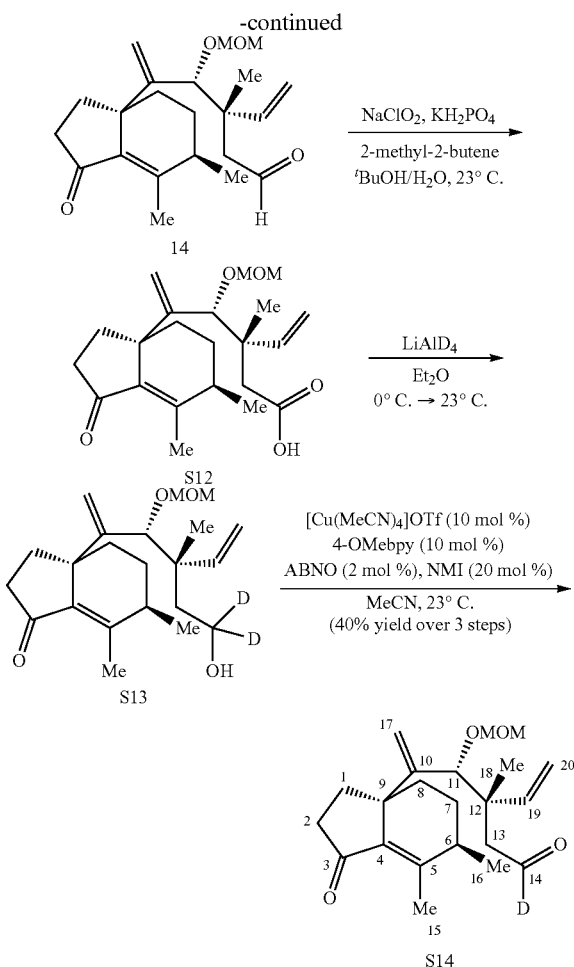

A 25 mL round bottom flask equipped with a stir bar was charged with aldehyde 14 (32.2 mg, 0.0894 mmol, 1 equiv) and tBuOH (4.5 mL) followed by deionized water (3.2 mL) and 2-methyl-2-butene (163 mg, 2.32 mmol, 246 μL, 26 equiv). Thereafter, a solution of $KH_2PO_4$ (42.6 mg, 0.313 mmol, 3.5 equiv) in $H_2O$ (650 μL) was added followed by a solution of $NaClO_2$ (8.9 mg, 0.0983 mmol, 1.1 equiv) in $H_2O$ (650 μL). The mixture was rapidly stirred at ambient temperature for 6 h, at which time the reaction was extracted into $Et_2O$ (4×2 mL). The combined organic layers were dried over $Na_2SO_4$, filtered, and concentrated under reduced pressure to afford 25.8 mg of a clear oil that was used in the next step without further purification.

A flame-dried 2 dram vial equipped with a stir bar was charged with $LiAlD_4$ (11.5 mg, 0.274 mmol, 4 equiv) and the atmosphere was exchanged three times for argon. Subsequently, anhydrous $Et_2O$ (1.7 mL) was added followed by dropwise addition of carboxylic acid S12 in $Et_2O$ (1.7 mL) over 5 min. The resulting light grey suspension was rapidly stirred at ambient temperature for 45 min, at which time $H_2O$ (1 mL) was cautiously added, using a vent needle to aid in expulsion of gas. The slurry was extracted into $Et_2O$ (4×2 mL), the combined organic layers were dried over $Na_2SO_4$, and concentrated under reduced pressure to afford 14.1 mg of a viscous oil that was used in the next step without further purification.

A flame-dried, 2 dram vial equipped with a stir bar was charged with alcohol S13 and MeCN (100 μL). Thereafter, added 140 μL of the [Cu]/bpy stock solution, 140 μL of the NMI stock solution, and 140 μL of the ABNO stock solution, in that order. The orange reaction was stirred at 960 rpm open to the atmosphere. Within 15 min, TLC analysis ($Et_2O$/hexanes=70%, UV and anisaldehyde) indicated complete conversion to aldehyde S14 ($R_f$=0.57, stains deep blue), and after 2 h, complete conversion to the desired enone-aldehyde product ($R_f$=0.66, stains brown) was observed. Subsequently, the resulting light blue solution was diluted with $Et_2O$ (2 mL), passed through a short pad of $SiO_2$ using $Et_2O$ as the eluent, and concentrated under reduced pressure to afford a pale yellow oil.

Purification was achieved via flash column chromatography on Sift [1.5 g $Et_2O$/hexanes=30%→45%] to afford deuterated aldehyde S14 (9.8 mg, 0.027 mmol, 40% yield over 3 steps) as a viscous, colorless oil. It should be noted that this compound was isolated as a 9:1 mixture of C6-epimers, separable after the reductive radical cyclization. NMR indicates 94% deuterium incorporation at C14.

TLC (80% $Et_2O$/hexanes): $R_f$=0.65 (UV).

$^1$H NMR (400 MHz, $CDCl_3$): δ 6.07 (dd, J=16.9, 9.9 Hz, 1H, C19), 5.48 (d, J=0.7 Hz, 1H, C17), 5.13 (dd, J=9.9, 2.4 Hz, 1H, C20), 5.09 (dd, J=16.9, 2.4 Hz, 1H, C20), 5.05 (br m, 1H, C17), 4.54 (d, J=6.7 Hz, 1H, OCH2OMe), 4.42 (d, J=6.7 Hz, 1H, OCH2OMe), 4.12 (br s, 1H, C11), 3.36 (s, 3H, OCH2OCH3), 2.56 (m, 2H, C13), 2.26 (m, 1H, C1), 2.19 (m, 1H, C8), 2.17 (m, 1H, C2), 2.14 (m, 1H, C6), 2.11 (s, 3H, C15), 2.00 (dd, J=17.0, 7.6 Hz, 1H, C2), 1.65 (m, 1H, C7), 1.52 (m, 1H, C1), 1.27 (s, 3H, C18), 1.25 (m, 1H, C8), 1.23 (m, 1H, C7), 1.07 (d, J=7.0 Hz, 3H, C16).

$^{13}$C NMR (101 MHz, $CDCl_3$): δ 208.1 (C3=O), 202.2 (C14=O) (1:1:1 triplet) (coupling of I=. 13C nucleus to quadrupolar 2H nucleus also causes T2 broadening), 151.4 (C5), 149.0 (C10), 142.4 (C19), 136.2 (C4), 122.7 (C17), 114.5 (C20), 94.2 (OCH2OCH3), 78.2 (C11), 56.6 (OCH2OCH3), 52.4 (C13) (reduced intensity due to 2H coupling), 50.5 (C9), 45.5 (C12), 37.4 (C6), 35.9 (C2), 33.1 (C8), 32.7 (C1), 28.2 (C7), 19.1 (C16), 18.9 (C18), 17.0 (C15).

FTIR (AT-IR): 2931, 2359, 2323, 1704, 1628, 1456, 1212, 1148, 1036, 919 cm$^{-1}$.

HRMS (TOF, ES+): calc'd for $C_{22}H_{31}DO_4Na$ [M+Na]$^+$ 384.2261, found 384.2270.

$[α]_D^{23}$: −43.2° (c=0.455, $CHCl_3$).

Example 7: Preparation of Deuterium-Labeled Tricycle (17-d)

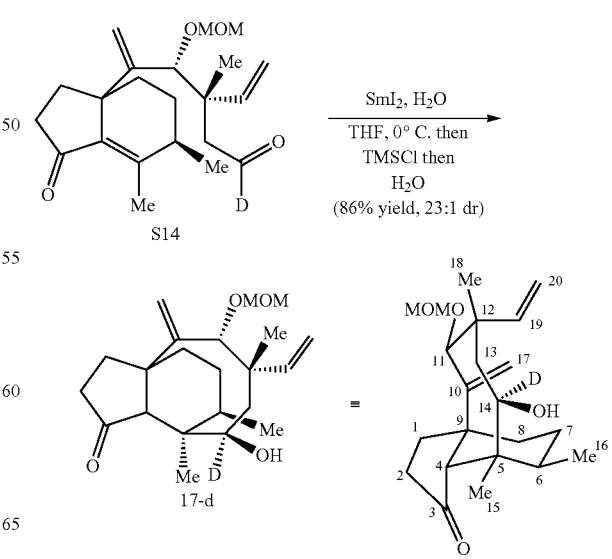

A 25 mL Schlenk flask equipped with a stir bar was charged with deuterated aldehyde S14 (7.3 mg, 0.0202 mmol, 1 equiv), THF (1.0 mL), and a solution of deionized H₂O (2.2 µL, 0.121 mmol, 6 equiv) in THF (184 µL) and submitted to five freeze-pump-thaw cycles. The solution was cooled to 0° C. and stirred at this temperature for 15 min. Thereafter, SmI₂/THF (606 µL, 0.0606 mmol, 3 equiv) was added dropwise over 8 min. After stirring an additional 10 min at 0° C., TMSCl/THF (195 µL, 0.101 mmol, 5 equiv TMSCl) was added dropwise over 2 min, and the reaction was stirred an additional 10 min. Throughout this time, the deep blue color was quenched to yellow. Thereafter, the reaction was removed from the ice bath and stirred open to the atmosphere for 5 min. The resulting pale yellow solution was diluted with Et₂O (5 mL), and washed with H₂O (2×2 mL). The aqueous layer was back extracted with Et₂O (2×2 mL), and the combined organic layers were dried over Na₂SO₄, filtered, and concentrated under reduced pressure to afford a dark orange oil.

Purification was achieved via flash column chromatography on SiO₂ [1.5 g SiO₂, Et₂O/hexanes=30%→40%] to afford deuterated tricycle 17-d (6.3 mg, 0.017 mmol, 84% yield) as a clear residue.

TLC (50% Et₂O/hexanes): $R_f$=0.55 (p-anisaldehyde, KMnO₄).

¹H NMR (400 MHz, CDCl₃): δ 6.35 (dd, J=17.8, 11.3 Hz, 1H, C19), 5.33 (dd, J=17.8, 1.4 Hz, 1H, C20), 5.34 (s, 1H, C17), 5.28 (s, 1H, C17), 5.19 (dd, J=11.2, 1.4 Hz, 1H, C20), 4.54 (d, J=7.1 Hz, 1H, OCH2OMe), 4.40 (d, J=6.7 Hz, 1H, OCH2OMe), 3.95 (s, 1H, C11), 3.38 (s, 3H, OCH2OCH3), 2.33 (m, 1H, C2), 2.29 (m, 1H, C2), 2.24 (m, 1H, C4), 2.06 (m, 1H, C1), 2.03 (m, 1H, C8), 1.92 (dd, J=16.1, 6.5 Hz, 1H, C13), 1.70 (m, 1H, C6), 1.60 (dt, J=13.3, 3.4 Hz, 1H, C7), 1.50 (dd, J=16.1, 0.9 Hz, 1H, C13), 1.39 (ddt, J=13.3, 6.5, 3.4 Hz, 1H, C7), 1.33 (m, 1H, C1), 1.30 (s, 3H, C15), 1.28 (m, 1H, C8), 1.24 (s, 3H, C18), 0.96 (d, J=7.0 Hz, 3H, C16).

¹³C NMR (101 MHz, CDCl₃): δ 216.8 (C3=O), 148.3 (C10), 139.9 (C19), 114.2 (C20), 112.2 (C17), 92.1 (OCH2OCH3), 77.2 (C11), 67.2 (C14) (1:1:1 triplet) (coupling of I=. 13C nucleus to quadrupolar 2H nucleus also causes T2 broadening), 59.6 (C4), 56.0 (OCH2OCH3), 46.5 (C9), 45.2 (C13) (reduced intensity due to 2H coupling), 44.7 (C12), 42.1 (C5), 37.3 (C6), 34.9 (C2), 31.0 (C8), 29.7 (C1), 28.8 (C18), 26.8 (C7), 18.2 (C16), 13.4 (C15).

FTIR (AT-IR): 3508, 2926, 1735, 1628, 1458, 1264, 1144, 1093, 1024, 907, 738 cm⁻¹.

HRMS (TOF, ES+): calc'd for C₂₂H₃₄DO₄ [M+H]+ 364.2598, found 364.2595.

$[\alpha]_D^{23}$: +123.5° (c=0.235, CHCl₃).

Example 8: Redox Relay by Transannular 1,5-HAT is Confirmed by Deuterium-Labeling

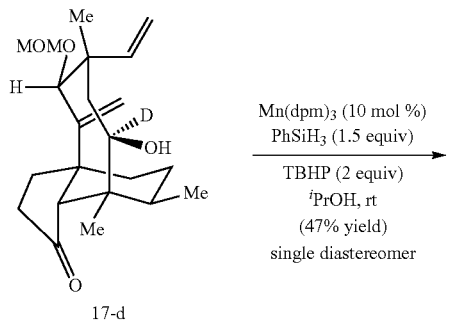

17-d

Mn(dpm)₃ (10 mol %)
PhSiH₃ (1.5 equiv)
TBHP (2 equiv)
ⁱPrOH, rt
(47% yield)
single diastereomer

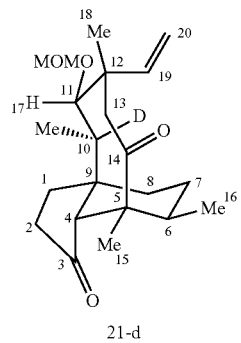

21-d

This procedure was adapted from work by Shenvi described above. A flame-dried 0.5 dram vial was charged with deuterated tricycle 17-d (3.0 mg, 0.00825 mmol, 1 equiv) and adventitious water was removed via azeotropic drying with PhMe (3×200 µL) under high vacuum. An oven-dried stir bar was added, and the atmosphere was exchanged three times for argon. Thereafter, a stock solution of PhSiH₃ (0.89 mg, 0.00825 mmol, 1.0 µL, 1.5 equiv) and tert-butyl hydroperoxide (2.5 µL of a 5.0 M solution in nonane, 0.0124 mmol, 2 equiv) in iPrOH (96 µL) were added. Additional iPrOH (100 µL) was added, and the mixture was sparged with argon for 10 min. Subsequently, tris(2,2,6,6-tetramethyl-3,5-heptanedionato)manganese(III) (0.50 mg, 0.000825 mmol, 10 mol %) was added as a solid, sparging was continued for an additional 20 sec, and the reaction was stirred at ambient temperature. After 10 min, the reaction was diluted with Et₂O/hexanes=50%, passed through a plug of SiO₂ (eluting with Et₂O/hexanes=50%), and concentrated under reduced pressure to afford a dark orange oil.

Purification was achieved via flash column chromatography on SiO₂ [750 mg SiO₂, Et₂O/hexanes=20%→30%] to afford ketone 21-d (1.4 mg, 0.00385 mmol, 47%) as a clear residue. Isolated starting material (1.4 mg, 0.00385 mmol, 47%).

This reaction exhibits a pronounced sensitivity to both residual oxygen and water. In addition, we found it critical to perform this reaction at 23° C., as higher temperatures promoted over-reduction and lower temperatures slowed catalysis. iPrOH was stored over activated 4 Å molecular sieves (pellets) overnight then was distilled from CaH₂ (10% w/v) in a flame-dried, argon-filled apparatus immediately prior to use.

Preparation of Stock Solutions: A stock solution of PhSiH₃ (20 µL) and tert-butyl hydroperoxide (50 µL of a 5.0 M solution in nonane) in iPrOH (1.6 mL) was prepared under an atmosphere of argon, and 100 µL of this stock solution was added to substrate, as described below.

TLC (40% Et₂O/hexanes): $R_f$=0.24 (p-anisaldehyde).

¹H NMR (400 MHz, CDCl₃): δ 6.18 (dd, J=17.8, 11.3 Hz, 1H, C19), 5.36 (dd, J=17.8, 1.5 Hz, 1H, C20), 5.27 (dd, J=11.2, 1.5 Hz, 1H, C20), 4.67 (ABq, J=6.8 Hz, 2H, OCH2OMe), 3.54 (d, J=5.2 Hz, 1H, C11), 3.42 (s, 3H, OCH2OCH3), 2.70 (d, J=12.4 Hz, 1H, C13), 2.57 (d, J=2.3 Hz, 1H, C4), 2.27 (m, 2H, C2), 2.07 (d, J=12.4 Hz, 1H, C13), [1.99 (C10) (dq signal absent)], 1.83 (dd, J=12.9, 9.6 Hz, 1H, C1), 1.74 (dq, J=14.3, 2.9 Hz, 1H, C8), 1.63 (dt, J=12.9, 3.3 Hz, 1H, C7), 1.56 (m, 1H, C6), 1.53 (m, 1H, C1), 1.46 (s, 3H, C15), 1.29 (m, 1H, C7), 1.21 (s, 3H, C18), 1.18 (d, J=6.8 Hz, 3H, C16), 1.17 (m, 1H, C8), 0.89 (d, J=7.2 Hz, 3H, C17).

$^{13}$C NMR (101 MHz, CDCl$_3$): δ 216.9 (C3=O), 212.5 (C14=O), 138.5 (C19), 116.1 (C20), 98.1 (OCH2OCH3), 81.9 (C11) (reduced intensity due to 2H coupling), 57.9 (C4), 56.8 (OCH2OCH3), 50.6 (C5), 48.1 (C12), 47.5 (C13), 45.6 (C9), 36.5 (C6), 35.5 (C10) (signal absent), 34.6 (C2), 31.0 (C8), 27.9 (C18), 26.1 (C7), 24.7 (C1), 21.0 (C15), 16.2 (C16), 11.1 (C17).

FTIR (AT-IR): 2930, 1733, 1698, 1455, 1089, 1035 cm$^{-1}$.
HRMS (TOF, ES+): calc'd for C$_{22}$H$_{34}$DO$_4$ [M+H]$^+$ 364.2598, found 364.2600.
[α]$_D^{23}$: +24.3° (c=0.065, CHCl$_3$).

Example 9: Redox Relay by Transannular 1,5-HAT without Deuterium-Labeling

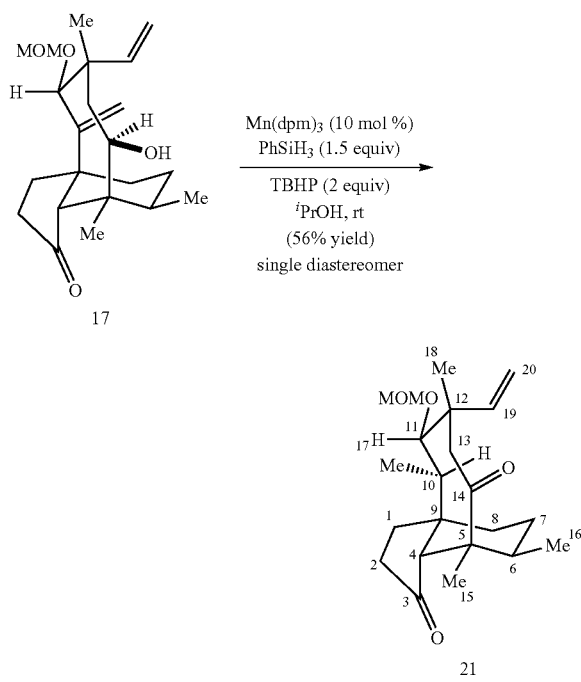

This procedure was adapted from work by Shenvi described above. A flame-dried 1 dram vial was charged with tricycle 17 (30.0 mg, 0.0828 mmol, 1 equiv) and adventitious water was removed via azeotropic drying with PhMe (3×400 μL) under high vacuum. An oven-dried stir bar was added, and the atmosphere was exchanged three times for argon. Thereafter, iPrOH (830 μL), PhSiH$_3$ (13.4 mg, 0.124 mmol, 15.2 μL, 1.5 equiv), and tert-butyl hydroperoxide (33.1 μL, of a 5.0 M solution in nonane, 0.166 mmol, 2 equiv) were added. The heterogeneous mixture was sparged with argon for 10 min. Subsequently, tris(2,2,6,6-tetramethyl-3,5-heptanedionato)manganese(III) (5.0 mg, 0.00828 mmol, 10 mol %) was added as a solid, sparging was continued for an additional 20 sec, and the reaction was stirred at ambient temperature. After 10 min, the reaction was diluted with Et$_2$O/hexanes=50%, passed through a plug of SiO$_2$ (eluting with Et$_2$O/hexanes=50%), and concentrated under reduced pressure to afford a dark orange oil.

Purification was achieved via flash column chromatography on SiO$_2$ [15 g SiO$_2$, Et$_2$O/hexanes=20%→35%] to afford ketone 21 (16.9 mg, 0.047 mmol, 56% yield) as a clear residue. Isolated starting material (12.1 mg, 0.033 mmol, 40%).

This reaction exhibits a pronounced sensitivity to both residual oxygen and water. In addition, we found it critical to perform this reaction at 23° C., as higher temperatures promoted over-reduction and lower temperatures slowed catalysis. iPrOH was stored over activated 4 Å molecular sieves (pellets) overnight then was distilled from CaH$_2$ (10% w/v) in a flame-dried, argon-filled apparatus immediately prior to use.

TLC (40% Et$_2$O/hexanes): R$_f$=0.24 (p-anisaldehyde).
$^1$H NMR (400 MHz, CDCl$_3$): δ 6.18 (dd, J=17.8, 11.3 Hz, 1H, C19), 5.36 (dd, J=17.8, 1.5 Hz, 1H, C20), 5.27 (dd, J=11.2, 1.5 Hz, 1H, C20), 4.67 (ABq, J=6.8 Hz, 2H, OCH2OMe), 3.54 (d, J=5.2 Hz, 1H, C11), 3.42 (s, 3H, OCH2OCH3), 2.70 (d, J=12.4 Hz, 1H, C13), 2.57 (d, J=2.3 Hz, 1H, C4), 2.27 (m, 2H, C2), 2.07 (d, J=12.4 Hz, 1H, C13), 1.99 (dq, J=7.2, 5.2 Hz, 1H, C10), 1.83 (dd, J=12.9, 9.6 Hz, 1H, C1), 1.74 (dq, J=14.3, 2.9 Hz, C8), 1.63 (dt, J=12.9, 3.3 Hz, 1H, C7), 1.56 (m, 1H, C6), 1.53 (m, 1H, C1), 1.46 (s, 3H, C15), 1.29 (m, 1H, C7), 1.21 (s, 3H, C18), 1.18 (d, J=6.8 Hz, 3H, C16), 1.17 (m, 1H, C8), 0.89 (d, J=7.2 Hz, 3H, C17).

$^{13}$C NMR (101 MHz, CDCl$_3$): δ 216.9 (C3=O), 212.5 (C14=O), 138.5 (C19), 116.1 (C20), 98.1 (OCH2OCH3), 81.9 (C11), 57.9 (C4), 56.8 (OCH2OCH3), 50.6 (C5), 48.1 (C12), 47.5 (C13), 45.6 (C9), 36.5 (C6), 35.5 (C10), 34.6 (C2), 31.0 (C8), 27.9 (C18), 26.1 (C7), 24.7 (C1), 21.0 (C15), 16.2 (C16), 11.1 (C17).

FTIR (AT-IR): 2957, 1734, 1698, 1455, 1089, 1035, 916 cm$^{-1}$.
HRMS (TOF, ES+): calc'd C22H$_{34}$O$_4$ [(M+H)–H2]$^+$ 361.2379, found 361.2396.
[α]$_D^{23}$: +34.0° (c=0.951, CHCl$_3$).

Example 10: Synthesis of 11-Epi and 11,12-Bis-Epi Dowd-Beckwith Rearrangement Tricycles (11-Epi-26) and (26)

A. Preparation of MOM Protected 11-Epi Crotylation Adduct (11-Epi-S5):

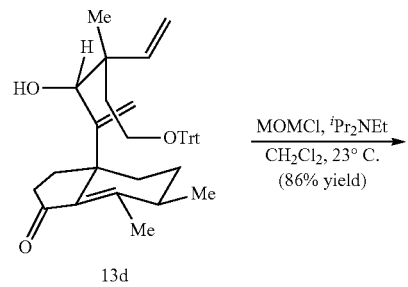

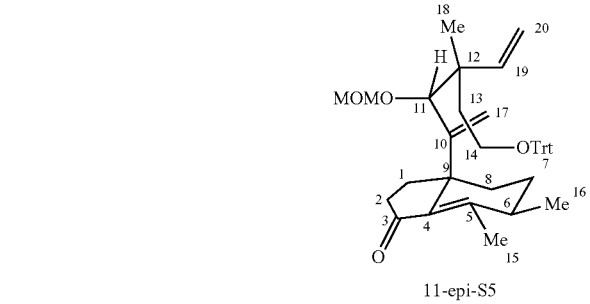

11-epi-S5

A flame-dried, 25 mL round bottom flask equipped with a stir bar was charged with alcohol 13d (200 mg, 0.360 mmol, 1 equiv), CH$_2$Cl$_2$ (1.8 mL), and freshly distilled iPr$_2$NEt (1.63 mL, 9.36 mmol, 26 equiv). To the homogeneous solution was added chloromethyl methyl ether (677 µL, 8.92 mmol, 25 equiv) dropwise over 10 min, taking care to vent HCl fumes formed via the use of a needle. The reaction was stirred at ambient temperature for 20 h. The resulting viscous, orange mixture was quenched via addition of sat. aq. NaHCO$_3$ (10 mL) and stirred at ambient temperature for 30 min. The aqueous layer was extracted with CH$_2$Cl$_2$ (3×10 mL) and washed with H$_2$O (10 mL). The combined organic layers were washed with brine (10 mL), dried over Na$_2$SO$_4$, and concentrated via distillation to afford a viscous, dark orange residue.

Purification was achieved via flash column chromatography on Sift [4 g Sift, Et$_2$O/hexanes=16%→35%] to afford MOM ether 11-epi-S5 (187 mg, 0.0.31 mmol, 86% yield) as a puffy white solid.

TLC (40% Et$_2$O/hexanes): R$_f$=0.4 (UV, p-anisaldehyde).
$^1$H NMR (400 MHz, CDCl$_3$): δ 7.49-7.36 (m, 6H, OCPh3), 7.35-7.17 (m, 9H, OCPh3), 5.85 (dd, J=17.7, 10.8 Hz, 1H, C19), 5.46 (s, 1H, C17), 4.96-4.90 (m, 2H, C17, C20), 4.82 (dd, J=17.7, 1.3 Hz, 1H, C20), 4.57 (d, J=6.9 Hz, 1H, OCH2OCH3), 4.51 (d, J=6.9 Hz, 1H, OCH2OCH3), 3.86 (s, 1H, C11), 3.34 (s, 3H, OCH2OCH3), 3.08 (t, J=7.2 Hz, 2H, C14), 2.41 (dd, J=12.8, 7.8 Hz, 1H, C2), 2.29-2.10 (m, 6H, C1, C6, C15), 2.07-2.02 (m, 1H, C8), 1.89 (dt, J=10.9, 7.3 Hz, 2H, C13), 1.63-1.41 (m, 2H, C2, C7), 1.26-1.15 (m, 2H, C7, C8), 1.09 (d, J=7.0 Hz, 3H, C16), 0.95 (s, 3H, C18).
$^{13}$C NMR (101 MHz, CDCl$_3$): δ 208.5 (C3=O), 150.8 (C5), 149.3 (C10), 144.4 (OCPh3), 143.6 (C19), 137.2 (C4), 128.6 (OCPh3), 127.6 (OCPh3), 126.7 (OCPh3), 122.4 (C17), 113.6 (C20), 95.8 (OCH2OCH3), 86.8 (OCPh3), 82.2 (C11), 60.7 (C14), 56.2 (OCH2OCH3), 51.3 (C9), 45.1 (C12), 37.5 (C6), 37.0 (C13), 35.7 (C1), 33.3 (C8), 32.3 (C2), 28.7 (C7), 20.1 (C18), 19.2 (C16), 17.0 (C15).
FTIR (thin film, NaCl): 2928, 1707, 1631, 1448, 1212, 1151, 1033, 917, 705 cm$^{-1}$.
HRMS (TOF, ES+): calc'd for C$_{41}$H$_{48}$O$_4$Na [M+Na]$^+$ 627.3450, found 627.3453.
[α]$_D^{23}$: −60.1° (c=0.355, CHCl$_3$).

B. Preparation of Alcohol (11-Epi-S6):

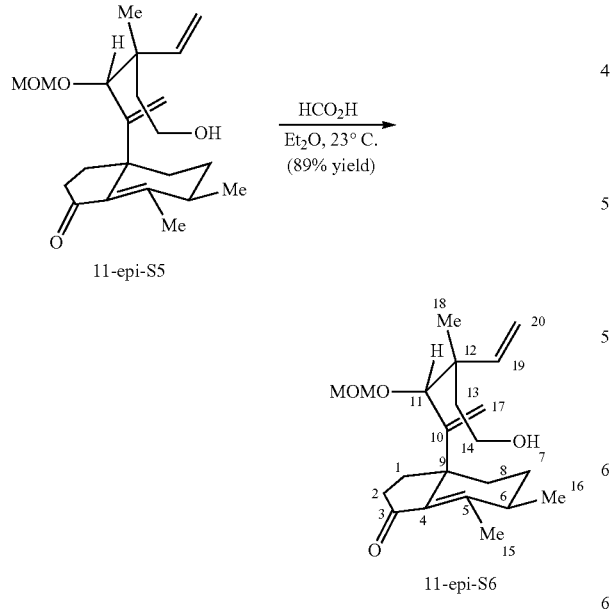

11-epi-S5

11-epi-S6

A 100 mL round bottom flask equipped with a stir bar was charged with MOM ether 11-epi-S5 (150 mg, 0.248 mmol, 1 equiv). Thereafter, a freshly prepared solution of formic acid (98%, 1.56 mL) and Et$_2$O (1.56 mL) was rapidly added, and within 5 min, the reaction was judged to be complete by TLC analysis. We found it critical to stop this reaction immediately after full conversion was achieved. Prolonged times afforded copious quantities of formate ester product. The reaction was diluted with Et$_2$O (5 mL) and quenched via slow addition of NaHCO$_3$ (25 mL). The aqueous layer was extracted with Et$_2$O (4×10 mL) and washed with H$_2$O (10 mL). The combined organic layers were washed with brine (10 mL), dried over Na$_2$SO$_4$, and concentrated under reduced pressure to afford a viscous yellow residue.

Purification was achieved via flash column chromatography on SiO$_2$ [Et$_2$O/hexanes=70%→90%] to afford alcohol 11-epi-S6 (80.0 mg, 0.221 mmol, 89% yield) as a viscous, colorless oil.

TLC (40% Et$_2$O/hexanes): R$_f$=0.09 (UV, p-anisaldehyde).
$^1$H NMR (400 MHz, CDCl$_3$): δ 6.05 (dd, J=17.7, 10.9 Hz, 1H, C19), 5.54 (s, 1H, C17), 5.11 (dd, J=10.9, 1.2 Hz, 1H, C20), 5.04 (dd, J=17.7, 1.2 Hz, 1H, C20), 4.98 (s, 1H, C17), 4.63 (d, J=7.0 Hz, 1H, OCH2OCH3), 4.55 (d, J=7.0 Hz, 1H, OCH2OCH3), 3.94 (s, 1H, C11), 3.67 (tt, J=7.2, 3.8 Hz, 2H, C14), 3.39 (s, 3H, OCH2OCH3), 2.44 (dd, J=13.0, 7.7 Hz, 1H, C2), 2.28-2.05 (m, 7H, C1, C6, C8, C15), 1.88 (t, J=7.0 Hz, 2H, C13), 1.60-1.45 (m, 2H, C2, C7), 1.28-1.18 (m, 2H, C7, C8), 1.12 (s, 3H, C18), 1.08 (d, J=7.0 Hz, 3H, C16).
$^{13}$C NMR (101 MHz, CDCl$_3$): δ 208.4 (C3=O), 151.0 (C5), 149.2 (C10), 144.1 (C19), 137.1 (C4), 122.8 (C17), 114.0 (C20), 95.6 (OCH2OCH3), 82.2 (C11), 59.8 (C14), 56.3 (OCH2OCH3), 51.3 (C9), 45.2 (C12), 39.9 (C13), 37.5 (C6), 35.6 (C1), 33.3 (C8), 32.3 (C2), 28.7 (C7), 20.1 (C18), 19.2 (C16), 17.0 (C15).
FTIR (thin film, NaCl): 3424, 2932, 1707, 1629, 1460, 1212, 1145, 1038, 916, 730 cm$^{-1}$.
HRMS (TOF, ES+): calc'd for C$_{22}$H$_{34}$O$_4$Na [M+Na]$^+$ 385.2355, found 385.2347.
[α]$_D^{23}$: −138.9° (c=0.29, CHCl$_3$).

C. Preparation of Aldehyde (11-Epi-14):

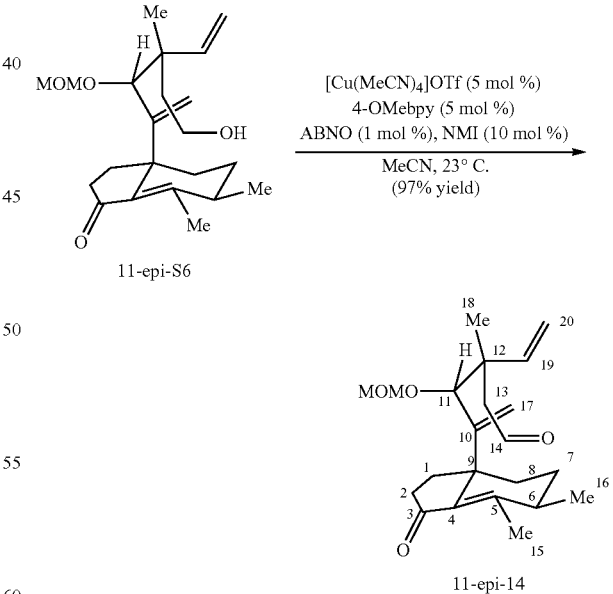

11-epi-S6

11-epi-14

A flame-dried, 2 dram vial equipped with a stir bar was charged with alcohol 11-epi-S6 (69.0 mg, 0.190 mmol, 1 equiv) and MeCN (1.9 mL). Thereafter, added 377 µL of the [Cu]/bpy stock solution, 377 µL of the NMI stock solution, and 377 µL of the ABNO stock solution, in that order. The orange reaction was stirred at 960 rpm open to the atmosphere for 90 min. Subsequently, the resulting light blue solution was diluted with Et₂O (1 mL), passed through a short pad of SiO₂ using Et₂O as the eluent, and concentrated under reduced pressure to afford a pale yellow oil.

Purification was achieved via flash column chromatography on SiO₂ [10 g SiO₂, Et₂O/hexanes=30%→60%] to afford aldehyde 11-epi-14 (66.4 mg, 0.184 mmol, 97% yield) as a viscous, colorless oil that solidified to a white solid upon standing in the freezer.

TLC (40% Et₂O/hexanes): R$_f$=0.59 (UV, p-anisaldehyde).

$^1$H NMR (400 MHz, CDCl₃): δ 9.75 (dd, J=3.7, 2.3 Hz, 1H, C14), 6.11 (dd, J=17.6, 10.9 Hz, 1H, C19), 5.46 (s, 1H, C17), 5.17 (dd, J=10.9, 0.8 Hz, 1H, C20), 5.10 (dd, J=17.7, 0.8 Hz, 1H, C20), 5.03 (s, 1H, C17), 4.57 (d, J=7.1 Hz, 1H, OCH2OCH3), 4.47 (d, J=7.1 Hz, 1H, OCH2OCH3), 4.03 (s, 1H, C11), 3.37 (s, 3H, OCH2OCH3), 2.61 (dd, J=15.0, 3.7 Hz, 1H, C13), 2.55 (dd, J=15.0, 2.3 Hz, 1H, C13), 2.43 (dd, J=13.0, 6.5 Hz, 1H, C2), 2.26-2.03 (m, 7H, C1, C6, C8, C15), 1.64-1.46 (m, 3H, C2, C7), 1.31 (s, 3H, C18), 1.27-1.12 (m, 2H, C7, C8), 1.08 (d, J=7.0 Hz, 3H, C16).

$^{13}$C NMR (101 MHz, CDCl₃): δ 208.2 (C3=O), 202.9 (C14=O), 151.2 (C5), 148.8 (C10), 141.9 (C19), 136.9 (C4), 123.3 (C17), 114.8 (C20), 94.7 (OCH2OCH3), 80.6 (C11), 56.3 (OCH2OCH3), 51.2 (C9), 50.5 (C13), 45.5 (C12), 37.5 (C6), 35.6 (C1), 33.2 (C8), 32.2 (C2), 28.8 (C7), 22.1 (C18), 19.2 (C16), 17.0 (C20).

FTIR (thin film, NaCl): 2931, 1706, 1628, 1457, 1268, 1210, 1144, 1095, 1030, 917 cm$^{-1}$.

HRMS (TOF, ES+): calc'd for C₂₂H₃₂O₄Na [M+Na]⁺ 383.2198, found 383.2202.

[α]$_D^{23}$: −108.9° (c=0.05, CHCl₃).

D. Preparation of 11-Epi Dowd-Beckwith Rearrangement Tricycle (11-Epi-26):

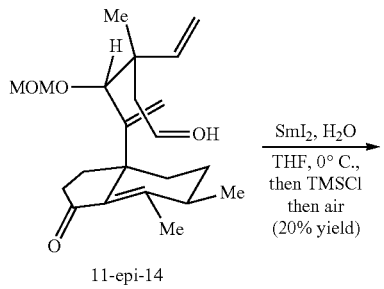

11-epi-14

A 2 dram vial equipped with a stir bar was charged with a solution of aldehyde 11-epi-14 (30 mg, 0.083 mmol, 1 equiv) in 4.1 mL of THF that had been submitted to five freeze-pump-thaw cycles and H₂O/THF (2.3 mL). The solution was cooled to 0° C. and stirred at this temperature for 5 min. Thereafter, SmI₂/THF (2.52 mL, 0.252 mmol, 3 equiv) was added dropwise over 8 min. The deep blue color of SmI₂ was immediately quenched upon addition of each drop. The first drop afforded a yellow solution, fading to a pale yellow and almost clear by the time 1.6 equiv SmI₂ had been added. When 2.2 equiv SmI₂ had been added, the blue color became increasingly persistent and upon addition of 2.6 equiv SmI₂, the reaction was dark blue/green. After stirring an additional 10 min at 0° C., TMSCl/THF (762 μL, 0.415 mmol, 5 equiv TMSCl) was added dropwise over 2 min, and the reaction was stirred an additional 10 min. Throughout this time, the deep blue color was quenched to yellow. Thereafter, the reaction was removed from the ice bath and stirred open to the atmosphere for 5 min. The resulting pale yellow solution was diluted with Et₂O (2 mL), and washed with H₂O (2×1 mL). The aqueous layer was back-extracted with Et₂O (2×1 mL), and the combined organic layers were dried over Na₂SO₄, filtered, and concentrated under reduced pressure to afford a dark orange oil.

Purification was achieved via flash column chromatography on SiO₂ [3 g SiO₂, Et₂O/hexanes=20%] to afford tricycle 11-epi-26 (5.8 mg, 0.0169 mmol, 20% yield) as a white solid.

TLC (50% Et₂O/hexanes): R$_f$=0.77 (p-anisaldehyde).

$^1$H NMR (400 MHz, CDCl₃): 6.06 (dd, J=17.5, 10.7 Hz, 1H, C19), 5.49 (dd, J=9.0, 5.7 Hz, 1H, C14), 5.13 (s, 1H, C17), 5.12 (dd, J=17.5, 1.3 Hz, 1H, C20), 5.06 (s, 1H, C17), 5.02 (dd, J=10.7, 1.3 Hz, 1H, C20), 4.61 (d, J=6.7 Hz, 1H, OCH2OCH3), 4.46 (d, J=6.7 Hz, 1H, OCH2OCH3), 4.34 (s, 1H, C11), 3.33 (s, 3H, OCH2OCH3), 2.51-2.35 (m, 3H, C1, C2), 2.26 (td, J=14.0, 13.6, 5.4 Hz, 1H, C8), 2.15 (dd, J=13.7, 5.7 Hz, 1H, C13), 2.07-1.97 (m, 1H, C6), 1.99-1.88 (m, 1H, C1), 1.79 (dd, J=13.8, 9.0 Hz, 1H, C13), 1.77-1.66 (dq, J=14.1, 4.7 Hz, 1H, C7), 1.43-1.35 (m, 1H, C7), 1.08 (s, 4H, C8, C15), 1.02 (s, 3H, C18), 0.90 (d, J=7.0 Hz, 3H, C16).

$^{13}$C NMR (101 MHz, CDCl₃): δ 219.2 (C3), 155.2 (C10), 145.6 (C19), 141.6 (C4), 120.0 (C14), 111.6 (C20), 107.2 (C17), 93.3 (OCH2OCH3), 77.7 (C11), 56.9 (C5), 55.4 (OCH2OCH3), 45.6 (C9), 44.9 (C12), 38.8 (C6), 38.5 (C2), 37.3 (C8), 36.5 (C13), 29.7 (C1), 27.9 (C7), 19.8 (C15), 18.3 (C18), 13.7 (C16).

FTIR (thin film, NaCl): 2930, 1712, 1632, 1454, 1369, 1213, 1147, 1101, 1042, 908 cm-1.

HRMS (FAB+): calc'd for C₂₂H₃₂O₃ [M]⁺ 344.2352, found 344.2381.

[α]$_D^{23}$: −276.7° (c=0.27, CHCl₃).

E. Preparation of MOM Protected 11,12-Bis-Epi Crotylation Adduct (11,12-Bis-Epi-S5):

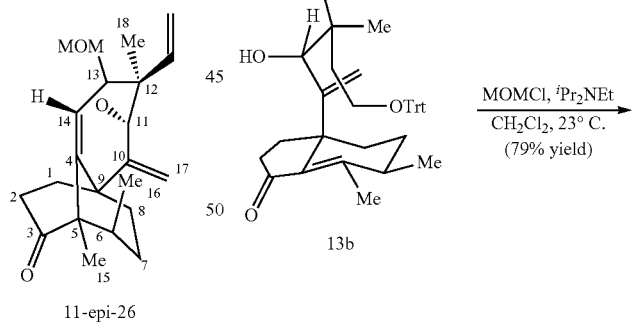

13b

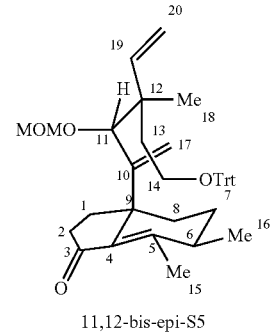

11,12-bis-epi-S5

A flame-dried, 25 mL round bottom flask equipped with a stir bar was charged with alcohol 13b (20 mg, 0.036 mmol, 1 equiv), CH$_2$Cl$_2$ (594 μL), and freshly distilled iPr$_2$NEt (163 μL, 0.936 mmol, 26 equiv). To the homogeneous solution was added chloromethyl methyl ether (68 μL, 0.900 mmol, 25 equiv) dropwise over 10 min, taking care to vent HCl fumes formed via the use of a needle. The reaction was stirred at ambient temperature for 36 h. The resulting viscous, orange mixture was quenched via addition of sat. aq. NaHCO$_3$ (2 mL) and stirred at ambient temperature for 30 min. The aqueous layer was extracted with CH$_2$Cl$_2$ (3×1 mL). The combined organic layers were washed with H$_2$O (1 mL), brine (1 mL), dried over Na$_2$SO$_4$, and concentrated via distillation to afford a viscous, dark orange residue.

Purification was achieved via flash column chromatography on SiO$_2$ [5 g Sift, Et$_2$O/hexanes=16%→35%] to afford MOM ether 11,12-bis-epi-SS (12 mg, 0.020 mmol, 79% yield) as a puffy white solid.

TLC (40% Et$_2$O/hexanes): R$_f$=0.44 (UV, p-anisaldehyde).

$^1$H NMR (400 MHz, CDCl$_3$): δ 7.47-7.38 (m, 6H, Ph$_3$CO), 7.33-7.18 (m, 9H, Ph$_3$CO), 5.74 (dd, J=17.5, 10.8 Hz, 1H, C19), 5.41 (s, 1H, C17), 4.98 (s, 1H, C17), 4.84 (d, J=10.8 Hz, 1H, C20), 4.80 (d, J=17.6 Hz, 1H, C20), 4.50 (d, J=6.9 Hz, 1H, OCH2OCH3), 4.40 (d, J=7.0 Hz, 1H, OCH2OCH3), 3.92 (s, 1H, C11), 3.32 (s, 3H, OCH2OCH3), 3.08 (d, J=22.2 Hz, 2H, C13), 2.38 (s, 1H, C2), 2.11 (d, J=9.5 Hz, 8H, C1, C2, C6, C8, C13, C15), 1.85 (s, 1H, C13), 1.47 (m, 2H, C2, C7), 1.11 (m, 2H, C7, C8), 1.06 (d, J=7.1 Hz, 3H, C16), 0.97 (s, 3H, C18).

$^{13}$C NMR (101 MHz, CDCl$_3$): δ 208.5 (C3=O), 150.98 (C5), 149.2 (C10), 144.4 (OCPh3), 143.1 (C19), 137.3 (C4), 128.6 (OCPh3), 127.6 (OCPh3), 126.8 (OCPh3), 123.2 (C17), 113.4 (C20), 94.6 (OCH2OCH3), 86.6 (OCPh3), 80.3 (C11), 60.7 (C14), 56.3 (OCH2OCH3), 51.0 (C9), 44.8 (C12), 38.1 (C13), 37.4 (C6), 35.6 (CO, 33.2 (C8), 32.1 (C2), 28.6 (C7), 19.1 (C16), 18.0 (C18), 17.0 (C15).

FTIR (thin film, NaCl): 2928, 1708, 1630, 1448, 1211, 1146, 1040, 916 cm$^{-1}$.

HRMS (TOF, ES+): calc'd for C$_{41}$H$_{48}$O$_4$Na [M+Na]+ 627.3450, found 627.3445.

[α]$_D^{23}$: −86.2° (c=0.43, CHCl$_3$).

F. Preparation of Alcohol (11,12-Bis-Epi-S6):

A 2 dram vial equipped with a stir bar was charged with MOM ether 11,12-bis-epi-S5 (12 mg, 0.020 mmol, 1 equiv). Thereafter, a freshly prepared solution of formic acid (98%, 125 μL) and Et$_2$O (125 μL) was rapidly added, and within 5 min, the reaction was judged to be complete by TLC analysis. We found it critical to stop this reaction immediately after full conversion was achieved. Prolonged times afforded copious quantities of formate ester product. The reaction was diluted with Et$_2$O (1 mL) and quenched via slow addition of NaHCO$_3$ (4 mL). The aqueous layer was extracted with Et$_2$O (4×1 mL). The combined organic layers were washed with H$_2$O (1 mL), brine (1 mL), dried over Na$_2$SO$_4$, and concentrated under reduced pressure to afford a viscous yellow residue.

Purification was achieved via flash column chromatography on Sift [Et$_2$O/hexanes=70%→90%] to afford alcohol 11,12-bis-epi-S6 (5.3 mg, 0.015 mmol, 73% yield) as a viscous, colorless oil.

TLC (70% Et$_2$O/hexanes): R$_f$=0.13 (UV, p-anisaldehyde).

$^1$H NMR (400 MHz, CDCl$_3$): δ 5.97 (dd, J=17.5, 10.9 Hz, 1H, C19), 5.48 (s, 1H, C17), 5.07-4.99 (m, 3H, C17, C20), 4.56 (d, J=7.0 Hz, 1H, (OCH2OCH3), 4.45 (d, J=7.0 Hz, 1H, OCH2OCH3), 4.07 (s, 1H, C11), 3.67 (qdd, J=10.9, 7.7, 6.4 Hz, 2H, C14), 3.38 (s, 3H, OCH2OCH3), 2.47 (dd, J=13.0, 7.0 Hz, 1H, C2), 2.27-2.11 (m, 4H, C1, C6, C8), 2.11 (s, 3H, C15), 1.96 (ddd, J=13.6, 7.6, 6.0 Hz, 1H, C13), 1.86 (dt, J=13.7, 7.2 Hz, 1H, C13), 1.56-1.40 (m, 2H, C2, C7), 1.19-1.11 (m, 2H, C7, C8), 1.11 (s, 3H, C18), 1.07 (d, J=7.1 Hz, 3H, C16).

$^{13}$C NMR (101 MHz, CDCl$_3$): δ 208.4 (C3=O), 151.1 (C5), 149.2 (C19), 143.7 (C4), 137.3 (C4), 123.5 (C17), 113.8 (C20), 94.4 (OCH2OCH3), 80.2 (C11), 60.0 (C14), 56.3 (OCH2OCH3), 51.1 (C9), 45.0 (C12), 41.4 (C13), 37.5 (C6), 35.7 (C1), 33.3 (C8), 32.1 (C2), 28.6 (C7), 19.1 (C16), 17.5 (C18), 17.1 (C15).

FTIR (thin film, NaCl): 3407, 2931, 1706, 1628, 1442, 1211, 1146, 1034, 915 cm$^{-1}$.

HRMS (TOF, ES+): calc'd for C$_{22}$H$_{34}$O$_4$Na [M+Na]$^+$ 385.2355, found 385.2353.

[α]$_D^{23}$: −177.9° (c=0.135, CHCl$_3$).

G. Preparation of Aldehyde (22):

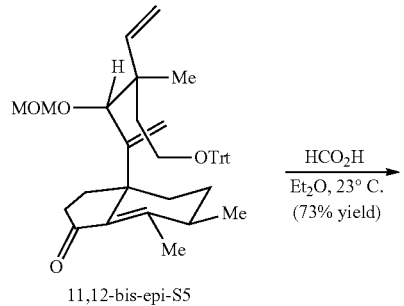
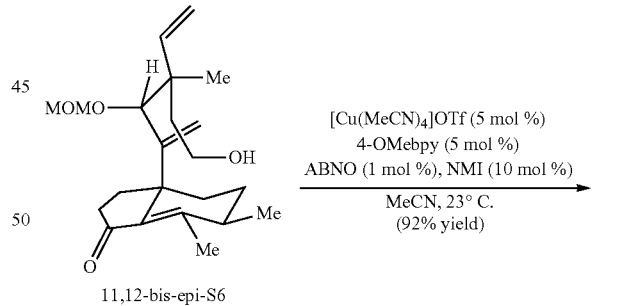

11,12-bis-epi-S5 → 11,12-bis-epi-S6

HCO$_2$H, Et$_2$O, 23° C. (73% yield)

[Cu(MeCN)$_4$]OTf (5 mol %)
4-OMebpy (5 mol %)
ABNO (1 mol %), NMI (10 mol %)
MeCN, 23° C.
(92% yield)

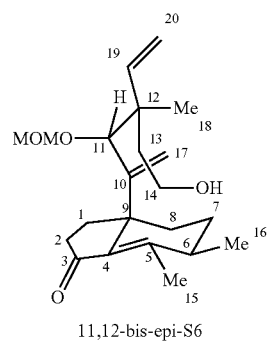
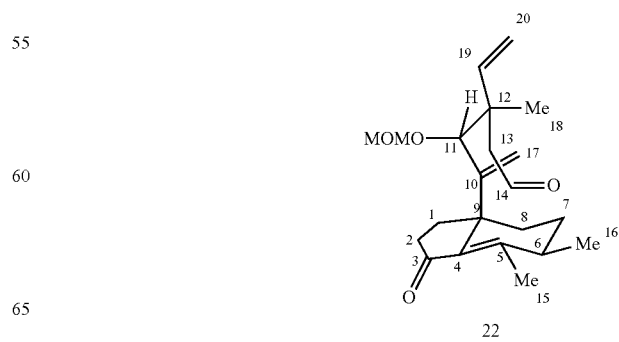

11,12-bis-epi-S6

22

A flame-dried, 2 dram vial equipped with a stir bar was charged with alcohol 11,12-bis-epi-S6 (210 mg, 0.580 mmol, 1 equiv) and MeCN (1.5 mL). Thereafter, added 1.1 mL of the [Cu]/bpy stock solution, 1.1 mL of the NMI stock solution, and 1.1 mL of the ABNO stock solution, in that order. The orange reaction was stirred at 960 rpm open to the atmosphere for 90 min. Subsequently, the resulting light blue solution was diluted with Et$_2$O (5 mL), passed through a short pad of SiO$_2$ using Et$_2$O as the eluent, and concentrated under reduced pressure to afford a pale yellow oil.

Purification was achieved via flash column chromatography on SiO$_2$ [10 g SiO$_2$, Et$_2$O/hexanes=30%→60%] to afford aldehyde 22 (196 mg, 0.544 mmol, 92% yield) as a viscous, colorless oil that solidified to a white solid upon standing in the freezer.

TLC (40% Et$_2$O/hexanes): R$_f$=0.59 (UV, p-anisaldehyde).

$^1$H NMR (400 MHz, CDCl$_3$): δ 9.74 (dd, J=3.5, 2.2 Hz, 1H, C14), 6.02 (dd, J=17.7, 10.7 Hz, 1H, C19), 5.45 (d, J=1.2 Hz, 1H, C17), 5.15-5.02 (m, 3H, C17, C20), 4.52 (d, J=7.1 Hz, 1H, OCH2OCH3), 4.37 (d, J=7.1 Hz, 1H, OCH2OCH3), 4.16 (d, J=1.1 Hz, 1H, C11), 3.33 (s, 3H, OCH2OCH3) 2.57 (dd, J=15.6, 3.5 Hz, 1H, C2, C13), 2.53-2.41 (m, 2H, C2, C13), 2.28-2.11 (m, 4H, C1, C6, C8), 2.11 (s, 3H, C15), 1.59-1.50 (m, 1H, C2), 1.50-1.42 (m, 1H, C7), 1.28 (s, 3H, C18), 1.22-1.08 (m, 2H, C7, C8), 1.07 (d, J=7.1 Hz, 3H, C16).

$^{13}$C NMR (101 MHz, CDCl$_3$): δ 208.3 (C3=O), 202.2 (C14=O), 151.3 (C5), 148.6 (C10), 142.9 (C19), 137.1 (C4), 123.7 (C17), 114.3 (C20), 93.8 (OCH2OCH3), 78.7 (C11), 56.5 (OCH2OCH3), 52.6 (C13), 51.0 (C9), 45.2 (C12), 37.5 (C6), 35.6 (C1), 33.2 (C8), 32.0 (C2), 19.2 (C16), 18.7 (C18), 17.1 (C15).

FTIR (thin film, NaCl): 2930, 1709, 1629, 1443, 1372, 1211, 1147, 1096, 1038, 917 cm$^{-1}$.

HRMS (TOF, ES+): calc'd for C$_{22}$H$_{32}$O$_4$Na [M+Na]$^+$ 383.2198, found 383.2190.

[α]$_D^{23}$: −164.5° (c=0.393, CHCl$_3$).

H. Preparation of 11,12-Bis-Epi Dowd-Beckwith Rearrangement Tricycle (26)

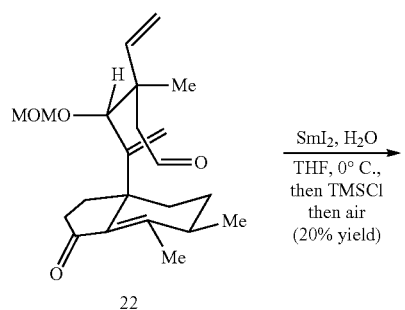

A 2 dram vial equipped with a stir bar was charged with a solution of aldehyde 22 (35 mg, 0.097 mmol, 1 equiv) in 4.8 mL of THF that had been submitted to five freeze-pump-thaw cycles and H$_2$O/THF (2.7 mL). The solution was cooled to 0° C. and stirred at this temperature for 5 min. Thereafter, SmI$_2$/THF (2.9 mL, 0.294 mmol, 3 equiv) was added dropwise over 8 min. The deep blue color of SmI$_2$ was immediately quenched upon addition of each drop. The first drop afforded a yellow solution, fading to a pale yellow and almost clear by the time 1.6 equiv SmI$_2$ had been added. When 2.2 equiv SmI$_2$ had been added, the blue color became increasingly persistent and upon addition of 2.6 equiv SmI$_2$, the reaction was dark blue/green. After stirring an additional 10 min at 0° C., TMSCl/THF (889 μL, 0.490 mmol, 5 equiv TMSCl) was added dropwise over 2 min, and the reaction was stirred an additional 10 min. Throughout this time, the deep blue color was quenched to yellow. Thereafter, the reaction was removed from the ice bath and stirred open to the atmosphere for 5 min. The resulting pale yellow solution was diluted with Et$_2$O (2 mL), and washed with H$_2$O (2×1 mL). The aqueous layer was back-extracted with Et$_2$O (2×1 mL), and the combined organic layers were dried over Na$_2$SO$_4$, filtered, and concentrated under reduced pressure to afford a dark orange oil.

Purification was achieved via flash column chromatography on SiO$_2$ [3 g SiO$_2$, Et$_2$O/hexanes=20%] to afford tricycle 26 (7 mg, 0.020 mmol, 21% yield) as a white solid.

TLC (30% Et$_2$O/hexanes): R$_f$=0.33 (p-anisaldehyde).

$^1$H NMR (400 MHz, CDCl$_3$): δ 6.11 (dd, J=17.6, 10.9 Hz, 1H, C19), 5.53 (dd, J=9.0, 5.5 Hz, 1H, C14), 5.10 (dd, J=11.0, 1.4 Hz, 1H, C20), 5.07 (d, J=0.8 Hz, 1H, C17), 5.03 (d, J=0.8 Hz, 1H, C17), 5.00 (dd, J=17.7, 1.5 Hz, 1H, C20), 4.63 (d, J=6.8 Hz, 1H, OCH2OCH3), 4.49 (d, J=6.7 Hz, 1H, OCH2OCH3), 4.21 (s, 1H, C11), 3.38 (s, 3H, OCH2OCH3), 2.49-2.36 (m, 3H, C1, C2), 2.35-2.18 (m, 2H, C8, C13), 2.02 (tq, J=9.4, 3.6, 2.4 Hz, 1H, C6), 1.92 (ddd, J=11.7, 9.0, 6.1 Hz, 1H, C2), 1.81-1.65 (m, 1H, C7), 1.61 (dd, J=13.6, 9.0 Hz, 1H, C13), 1.45-1.36 (m, 1H, C7), 1.26 (d, J=0.9 Hz, 3H, C18), 1.10 (s, 3H, C15), 1.10-1.01 (m, 1H, C8), 0.92 (d, J=7.0 Hz, 3H, C16).

$^{13}$C NMR (101 MHz, CDCl$_3$): δ 219.1 (C3=O), 155.2 (C10), 142.3 (C19), 141.8 (C10), 119.8 (C17), 112.3 (C20), 106.7 (C14), 93.1 (OCH2OCH3), 79.9 (C11), 56.9 (C5), 55.4 (OCH2OCH3), 45.1 (C9), 45.0 (C12), 38.7 (C6), 38.5 (C1), 37.1 (C8), 35.6 (C13), 29.6 (C2), 27.8 (C7), 23.1 (C18), 19.8 (C15), 13.7 (C16).

FTIR (thin film, NaCl): 2923, 2853, 1711, 1461, 1378, 1261, 1142, 1101, 1040 cm$^{-1}$.

HRMS (TOF, ES+): calc'd for C$_{22}$H$_{33}$O$_3$ [M+H]$^+$ 345.2430, found 345.2409.

[α]$_D^{23}$: −78.7° (c=0.045, CHCl$_3$).

Example 11: X-Ray Structure Determination for Compounds 16, 17, and 26

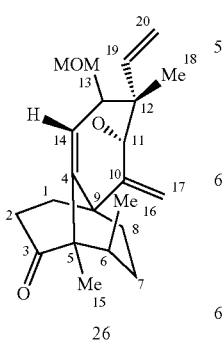

Low-temperature diffraction data (φ- and ω-scans) were collected on a Bruker AXS D8 VENTURE KAPPA diffractometer coupled to a PHOTON 100 CMOS detector with Cu-Kα radiation (λ=1.54178 Å) from a IμS HB micro-focus sealed X-ray tube. All diffractometer manipulations, including data collection, integration, and scaling were carried out using the Bruker APEXII software. See, APEX2, Version 2 User Manual, M86-E01078, Bruker Analytical X-ray Systems, Madison, Wis., June 2006. Absorption corrections were applied using SADABS. See, Sehldrick, "SADABS (version 2008/1): Program for Absorption Correction for Data from Area Detector Frames", University of Göttingen, 2008. The structure was solved by intrinsic phasing using SHELXT14 and refined against F2 on all data by full-matrix least squares with SHELXL-201415 using established refinement techniques. See, Macrae, Appl. Cryst. 2006, 39, 453. All non-hydrogen atoms were refined anisotropically. Unless otherwise noted, all hydrogen atoms were included into the model at geometrically calculated positions and refined using a riding model. The isotropic displacement parameters of all hydrogen atoms were fixed to 1.2 times the U value of the atoms they are linked to (1.5 times for methyl and hydroxyl groups). Crystallographic data for 16, 17, and 26 can be obtained free of charge from The Cambridge Crystallographic Data Centre (CCDC) via www.ccdc.cam.a-c.uk/data request/cif under CCDC deposition numbers 1589653-1589655. Graphical representation of the structure with 50% probability thermal ellipsoids was generated using Mercury visualization software. See, Parsons, Acta. Crystallogr. 2013, B69, 249.

TABLE S5

Crystal and refinement data for compounds 16, 17, and 26.

| | 16 | 17 | 26 |
|---|---|---|---|
| CCDC Number | 1589655 | 1589654 | 1589653 |
| Empirical formula | $C_{22}H_{34}O_6$ | $C_{22}H_{34}O_4$ | $C_{22}H_{32}O_3$ |
| Formula weight | 394.49 | 362.49 | 344.47 |
| T (° K) | 100 | 100 | 100 |
| Crystal system | Orthorhombic | Orthorhombic | Orthorhombic |
| Space group | P212121 | P212121 | P212121 |
| A (Å) | 7.2336(4) | 8.8601(3) | 7.4344(9) |
| B | 16.5583(8) | 11.6560(4) | 11.7916(15) |
| C | 34.6198(18) | 37.8871(14) | 21.810(3) |
| α, ° | 90 | 90 | 90 |
| β, ° | 90 | 90 | 90 |
| γ, ° | 90 | 90 | 90 |
| Volume (Å3) | 4146.6(4) | 3912.7(2) | 1912.0(4) |
| Z | 8 | 8 | 4 |
| dcalc (g/cm$^3$) | 1.264 | 1.231 | 1.197 |
| Abs. coeff. (mm$^{-1}$) | 0.738 | 0.658 | 0.609 |
| θ range (°) | 2.552 to 79.430 | 3.968 to 79.461 | 4.054 to 78.898 |
| Abs. correction | Semi-empirical | Semi-empirical | Semi-empirical |
| GOF | 1.066 | 1.097 | 1.064 |
| $^a$R1,$^a$wR2,$^b$[I > 2σ(I)] | 0.0345, 0.0897 | 0.0339, 0.0877 | 0.0291, 0.0764 |
| Flack parameter | 0.04(3) | 0.06(2) | 0.00(4) |
| Extinction coefficient | n/a | 0.00096(12) | 0.0103(7) |

$^a R_1 = \Sigma ||F_o| - |F_c||/\Sigma |F_o|$.
$^b wR_2 = [\Sigma[w(F_o^2 - F_c^2)_2]/\Sigma[w(F_o^2)_2]]^{1/2}$.

A. Special Refinement Details for 16

Compound 16 crystallizes in the orthorhombic space group P212121 with two molecules in the asymmetric unit. The coordinates for the hydrogen atoms bound to O2A, O4A, O2B, and O4B were located in the difference Fourier synthesis and refined using a riding model. No hydrogen bond acceptor was found for O2B. Absolute configuration was determined by anomalous dispersion (Flack=0.04(3)).

B. Special Refinement Details for 17

Compound 17 crystallizes in the orthorhombic space group P212121 with two molecules in the asymmetric unit. The coordinates for the hydrogen atoms bound to O2A and O2B were located in the difference Fourier synthesis and refined using a riding model. Absolute configuration was determined by anomalous dispersion (Flack=0.06(2)).

C. Special Refinement Details for 26

Compound 26 crystallizes in the orthorhombic space group P212121 with one molecule in the asymmetric unit. Absolute configuration was determined by anomalous dispersion (Flack=0.00(4)).

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document, including Farney, Feng, Schafers, and Reisman, "A Total Synthesis of (+)-Pleuromutilin," *J. Am. Chem. Soc.,* 2018, 140(4):1267-1270, are hereby incorporated herein by reference, each in its entirety, for all purposes.

What is claimed is:
1. A process comprising:
contacting a compound of Formula I

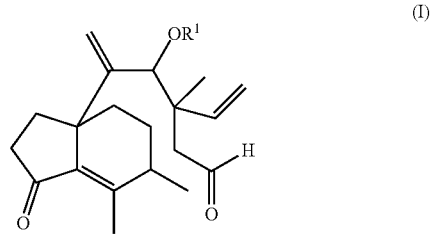

(I)

with samarium(II) iodide
in an organic solvent;

for a time and under conditions effective to produce a compound of Formula II

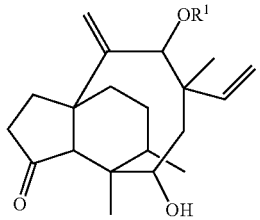
(II)

wherein R¹ is H or an oxygen protecting group.

2. The process of claim 1, wherein the organic solvent is a polar organic solvent.

3. The process of claim 1, wherein the organic solvent is an ethereal solvent.

4. The process of claim 1, wherein the organic solvent is tetrahydrofuran.

5. The process of claim 1, wherein the conditions are anaerobic.

6. The process of claim 1, wherein the organic solvent further comprises water.

7. The process of claim 1, comprising about 2.5 to about 3.5 moles of samarium(II) iodide per 1 mole of the compound of Formula I.

8. The process of claim 1, wherein the oxygen protecting group is methoxymethyl, tetrahydropyranyl, t-butyl, allyl, benzyl, silyl, acetyl, pivaloyl, trityl, or benzoyl.

9. The process of claim 1, wherein the oxygen protecting group is methoxymethyl ether.

10. The process of claim 1, further comprising preparing the compound of Formula I by
contacting a compound of Formula III with an oxygen protecting group reagent:

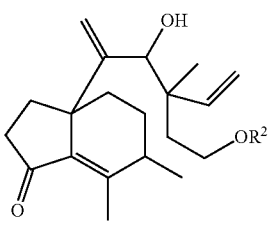
(III)

wherein R² is an oxygen protecting group that is an orthogonal protecting group, as compared to R¹;
to form a compound of Formula IA

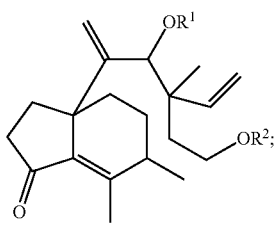
(IA)

subjecting the compound of Formula IA to conditions effective to produce a compound of Formula IB

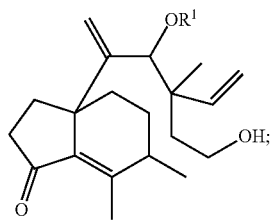
(IB)

and
oxidizing the compound of Formula IB under conditions sufficient to produce the compound of Formula I.

11. The process of claim 10, wherein R² is triphenyl methyl.

12. The process of claim 10, wherein the conditions effective to produce the compound of Formula IB comprise formic acid.

13. The process of claim 10, wherein the oxidizing conditions comprise a copper catalyst.

14. The process of claim 13, wherein the copper catalyst is [Cu(MeCN)₄]OTf or CuCu(OTf)₂.

15. The process of claim 10, wherein the compound of Formula III is prepared by:
contacting a compound of Formula A

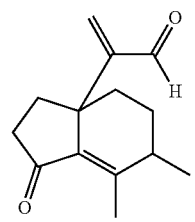
(A)

with a compound of Formula IVa or IVb

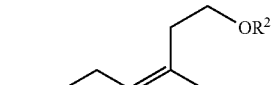
(IVa)

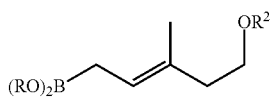
(IVb)

wherein:
each R is, independently, H or C₁₋₆alkyl or R, together with the atoms to which they are attached, forms a cyclic boronic ester moiety.

16. The process of claim 15, wherein the contacting is performed in an organic solvent under conditions sufficient to produce the compound of Formula III.

17. The process of claim 16, wherein the organic solvent is toluene.

18. The process of claim 16, wherein the temperature is about −10 to about 10° C.

19. The process of claim 15, wherein the diastereomeric excess of the compound of Formula III is at least 20%.

20. The process of claim 1, further comprising:

subjecting the compound of Formula II to conditions effective to produce a compound of Formula V or VA:

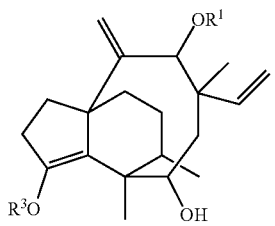

(V)

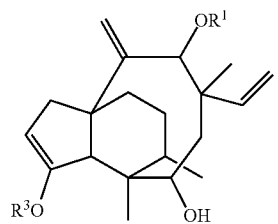

(VA)

wherein, R³ is a silyl protecting group.

21. The process of claim 20, further comprising:

subjecting a compound of Formula V or VA to conditions sufficient to provide a compound of Formula VI:

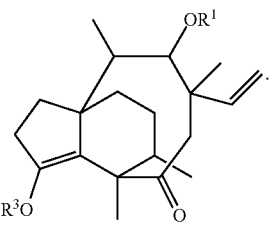

(VI)

22. The process of claim 21, wherein the conditions sufficient to provide the compound of Formula VI comprise tris(2,2,6,6-tetramethyl-3,5-heptanedionato)manganese (III), phenylsilane and tert-butyl hydroperoxide.

23. The process of claim 21, further comprising:

subjecting the compound of Formula VI to conditions sufficient to produce a compound of Formula VII:

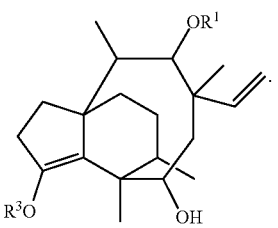

(VII)

24. The process of claim 23, further comprising subjecting the compound of Formula VII to conditions sufficient to provide pleuromutilin.

25. The process of claim 24, wherein the pleuromutilin is (+)-pleuromutilin.

* * * * *